(12) United States Patent
Tracey

(10) Patent No.: US 7,004,899 B2
(45) Date of Patent: Feb. 28, 2006

(54) SYSTEM AND METHOD FOR ASSESSING URINARY FUNCTION

(75) Inventor: Michael R. Tracey, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 156 days.

(21) Appl. No.: 10/183,298

(22) Filed: Jun. 27, 2002

(65) Prior Publication Data
US 2003/0023134 A1    Jan. 30, 2003

Related U.S. Application Data

(60) Provisional application No. 60/372,579, filed on Apr. 12, 2002, provisional application No. 60/302,069, filed on Jun. 29, 2001.

(51) Int. Cl.
*A61F 2/00*    (2006.01)

(52) U.S. Cl. ..................................................... 600/29

(58) Field of Classification Search ........ 600/591–592, 600/593, 561, 588, 434, 433, 435, 568–587, 600/589, 573, 300, 29, 30, 33–35; 604/264, 604/284, 915, 919, 920, 100.03, 121, 97.02; 606/192, 193
See application file for complete search history.

(56) References Cited

U.S. PATENT DOCUMENTS

| 926,197 | A | 6/1909 | Kim |
| 1,688,795 | A | 10/1928 | Nils |
| 3,685,787 | A | 8/1972 | Adelberg |
| 3,699,964 | A | 10/1972 | Ericson |
| 3,789,835 | A | 2/1974 | Whitman |
| 3,812,841 | A | 5/1974 | Isaacson |
| 3,900,184 | A | 8/1975 | Burke et al. |
| 3,970,090 | A | 7/1976 | Loiacono |
| 4,022,209 | A | 5/1977 | Nehring |
| 4,063,548 | A | * 12/1977 | Klatt et al. ................. 600/546 |
| 4,216,907 | A | 8/1980 | Fuller |
| 4,217,911 | A | * 8/1980 | Layton ....................... 600/561 |

(Continued)

FOREIGN PATENT DOCUMENTS

EP    0 608 593    8/1994

(Continued)

OTHER PUBLICATIONS

Petros, P.E.P. et al., An Integral Theory And Its Method For The Diagnosis And Management Of Female Urinary Incontinence, Scandinavian Journal of Urology and Nephorology, 1993, Supplement 153.

(Continued)

*Primary Examiner*—Max F. Hindenburg
*Assistant Examiner*—Nikita R. Veniaminov

(57) ABSTRACT

A portable, self-contained medical diagnostic system is provided for assessing urinary function. The system includes a control device including a processor, a pump device, and a pressure sensor, and a test module removably coupled to the control device, and further including a pressure interface and a tubing assembly defining a first fluid conduit between a first fluid inlet and a first fluid outlet. The pump device is coupled to the first fluid conduit for pumping fluid therethrough. The system also includes an insert member having a first channel therethrough and coupled to the first fluid outlet so that fluid flowing through the first fluid conduit may flow through the first channel. The insert member is dimensioned for insertion into a patient's bladder through the urethral canal. When so inserted, the pressure interface transmits bladder pressure information to the pressure sensor.

23 Claims, 41 Drawing Sheets

U.S. PATENT DOCUMENTS

| | | | | |
|---|---|---|---|---|
| 4,236,520 | A | 12/1980 | Anderson | |
| 4,248,214 | A | 2/1981 | Hannah et al. | |
| 4,367,740 | A | 1/1983 | Evanoski | |
| 4,407,301 | A * | 10/1983 | Streisinger | 600/587 |
| 4,432,352 | A | 2/1984 | Wineland | |
| 4,432,757 | A | 2/1984 | Davis, Jr. | |
| 4,484,585 | A | 11/1984 | Baier | |
| 4,557,255 | A | 12/1985 | Goodman | |
| 4,567,880 | A | 2/1986 | Goodman | |
| 4,632,684 | A * | 12/1986 | Karbassiyoon et al. | 65/379 |
| 4,704,102 | A | 11/1987 | Guthery | |
| 4,731,060 | A | 3/1988 | Catalano | |
| 4,738,659 | A | 4/1988 | Sleiman | |
| 4,750,488 | A | 6/1988 | Wuchinich et al. | |
| 4,813,935 | A | 3/1989 | Haber et al. | |
| 4,816,020 | A | 3/1989 | Brownell | |
| 4,872,483 | A * | 10/1989 | Shah | 137/757 |
| 4,998,527 | A | 3/1991 | Meyer | |
| 5,176,148 | A | 1/1993 | Wiest et al. | |
| 5,176,664 | A | 1/1993 | Weisman | |
| 5,331,548 | A * | 7/1994 | Rollema et al. | 600/561 |
| 5,342,298 | A * | 8/1994 | Michaels et al. | 604/85 |
| 5,385,563 | A * | 1/1995 | Gross | 604/284 |
| 5,433,216 | A * | 7/1995 | Sugrue et al. | 600/591 |
| 5,449,345 | A | 9/1995 | Taylor et al. | |
| 5,480,417 | A | 1/1996 | Hascoet et al. | |
| 5,520,636 | A * | 5/1996 | Korth et al. | 604/30 |
| 5,566,680 | A | 10/1996 | Urion et al. | |
| 5,623,925 | A * | 4/1997 | Swenson et al. | 600/301 |
| 5,624,395 | A | 4/1997 | Mikhail et al. | |
| 5,674,238 | A | 10/1997 | Sample et al. | |
| 5,688,239 | A | 11/1997 | Walker | |
| 5,722,931 | A | 3/1998 | Heaven | |
| 5,733,230 | A | 3/1998 | Sawchuck et al. | |
| 5,772,628 | A | 6/1998 | Bacich et al. | |
| 5,788,631 | A | 8/1998 | Fiddian-Green | |
| 5,792,042 | A | 8/1998 | Cohen et al. | |
| 5,800,407 | A | 9/1998 | Eldor | |
| 5,855,549 | A | 1/1999 | Newman | |
| 5,858,003 | A * | 1/1999 | Atala | 604/175 |
| 5,865,815 | A | 2/1999 | Tihon | |
| 5,868,135 | A | 2/1999 | Kaufman | |
| 5,868,680 | A | 2/1999 | Kaufman | |
| 5,887,593 | A | 3/1999 | Levius | |
| 6,001,060 | A * | 12/1999 | Churchill et al. | 600/300 |
| 6,004,305 | A | 12/1999 | Hursman et al. | |
| 6,021,781 | A * | 2/2000 | Thompson et al. | 128/898 |
| 6,022,955 | A | 2/2000 | Sarin et al. | |
| 6,056,699 | A | 5/2000 | Sohn et al. | |
| 6,063,045 | A * | 5/2000 | Wax et al. | 600/591 |
| 6,071,230 | A | 6/2000 | Henalla | |
| 6,086,549 | A | 7/2000 | Nelse et al. | |
| 6,110,099 | A | 8/2000 | Benderev | |
| 6,119,697 | A | 9/2000 | Engel et al. | |
| 6,129,330 | A | 10/2000 | Guala | |
| 6,162,201 | A | 12/2000 | Cohen et al. | |
| 6,258,060 | B1 | 7/2001 | Willard | |
| 6,258,087 | B1 | 7/2001 | Edwards | |
| 6,283,987 | B1 | 9/2001 | Laird | |
| 6,315,711 | B1 | 11/2001 | Conway et al. | |
| 6,358,229 | B1 | 3/2002 | Tihon | |
| 6,396,416 | B1 | 5/2002 | Kuusela et al. | |
| 6,434,418 | B1 * | 8/2002 | Neal et al. | 600/511 |
| 6,447,462 | B1 | 9/2002 | Wallace et al. | |
| 6,461,332 | B1 | 10/2002 | Mosel et al. | |
| 6,579,266 | B1 * | 6/2003 | Mosel et al. | 604/174 |
| 6,666,828 | B1 * | 12/2003 | Greco et al. | 600/561 |
| 6,699,175 | B1 | 3/2004 | Miller | |
| 6,719,709 | B1 * | 4/2004 | Whalen et al. | 600/587 |
| 6,720,887 | B1 * | 4/2004 | Zunti | 340/870.28 |
| 2001/0045355 | A1 | 11/2001 | Gephart et al. | |
| 2002/0111586 | A1 | 8/2002 | Mosel | |
| 2002/0115908 | A1 | 8/2002 | Miller | |
| 2002/0147423 | A1 | 10/2002 | Burbank et al. | |
| 2002/0165521 | A1 | 11/2002 | Cioanta et al. | |
| 2002/0198506 | A1 * | 12/2002 | Whalen et al. | 604/328 |
| 2003/0163086 | A1 | 8/2003 | Denyer et al. | |
| 2003/0181897 | A1 | 9/2003 | Thomas et al. | |
| 2003/0208183 | A1 | 11/2003 | Whalem et al. | |
| 2004/0176747 | A1 | 9/2004 | Feneley | |

FOREIGN PATENT DOCUMENTS

| | | |
|---|---|---|
| EP | 0 878 166 A1 | 11/1998 |
| GB | 2261169 A * | 5/1993 |
| WO | WO 00/23127 | 4/2000 |

OTHER PUBLICATIONS

Lane, T.M. et al., Leak-point pressures, BJU International 2000, vol. 86, pp. 942-949.

McLennan, M.T. et al., Leak-Point Pressure: Clinical Application of Values at Two Different Volumes, International Urogynecology Journal, 2000, vol. 11, pp. 136-141.

Petros, P.E.P. et al., An Anatomical Classification—a New Paradigm for Management of Urinary Dysfunction in the Female, International Urogynecology Journal, 1999, vol. 10, pp. 29-35.

Petros, P.E.P. et al., An anatomical classification—a new paradigm for management of female lower urinary tract dysfunction, European Journal of Obstetrics & Gynecology and Reproductive Biology, 1998, vol. 80, pp. 87-94.

Kim, K.J. et al., The Vesico-Urethral Pressuregram analysis Of Urethral Function Under Stress, 1997, vol. 30, No. 1, pp. 19-25.

Sanchez-Doblado, F. et al., Computerized analysis of urological parameters, Medical & Biological Engineering & Computing, 1988, vol. 26, pp. 325-327.

Kim, K-J, et al., Principles of urodynamics pressure measurement and its implication to female continence function, Journal of Biomechanics, 1998, vol. 31, pp. 861-865.

Lumaxpro Fiberoptic Cystometry System, Cooper Surgical, Shelton, CT.

Andromeda, Ellipse, The modular concept for precise urodynamics, Timm Medical Technologies, Inc. Eden Prairie, MN.

Bonney et al., Historical Presentation, Berlin-Brandenburgische 2002.

English Abstract for EP0878166.

*See face of article for English abstract.

* cited by examiner

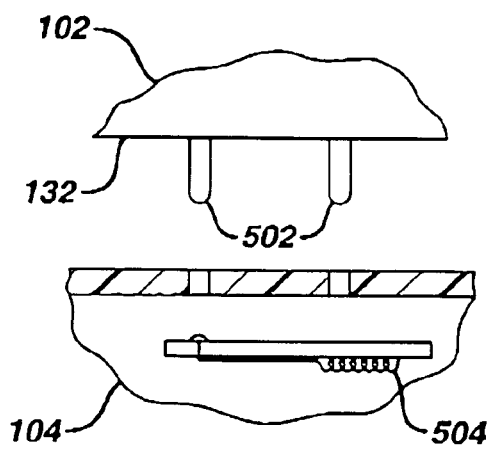
FIG. 5a
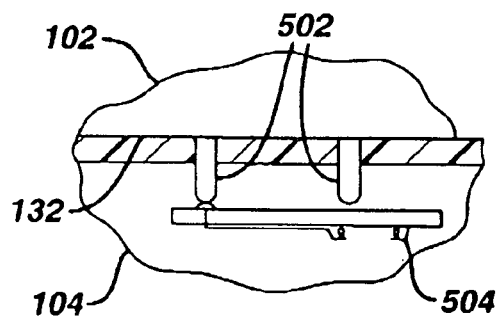
FIG. 5b
FIG. 6
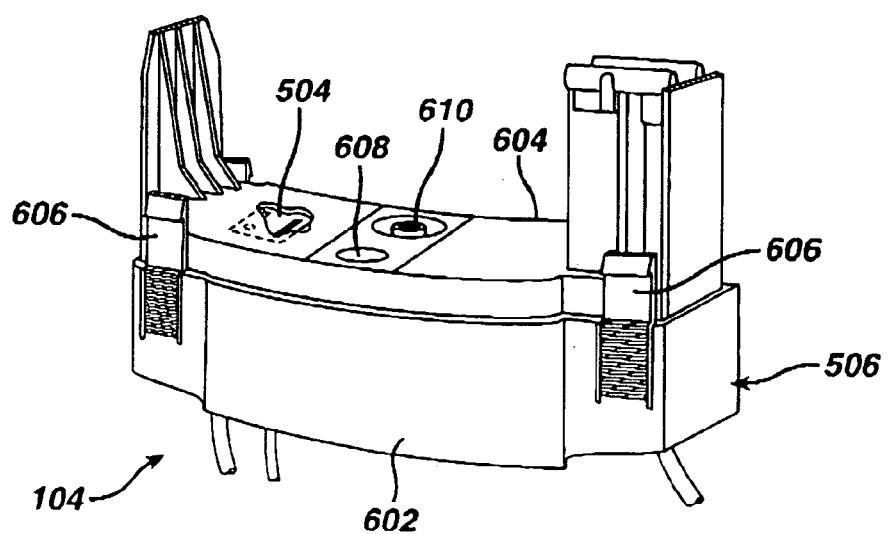

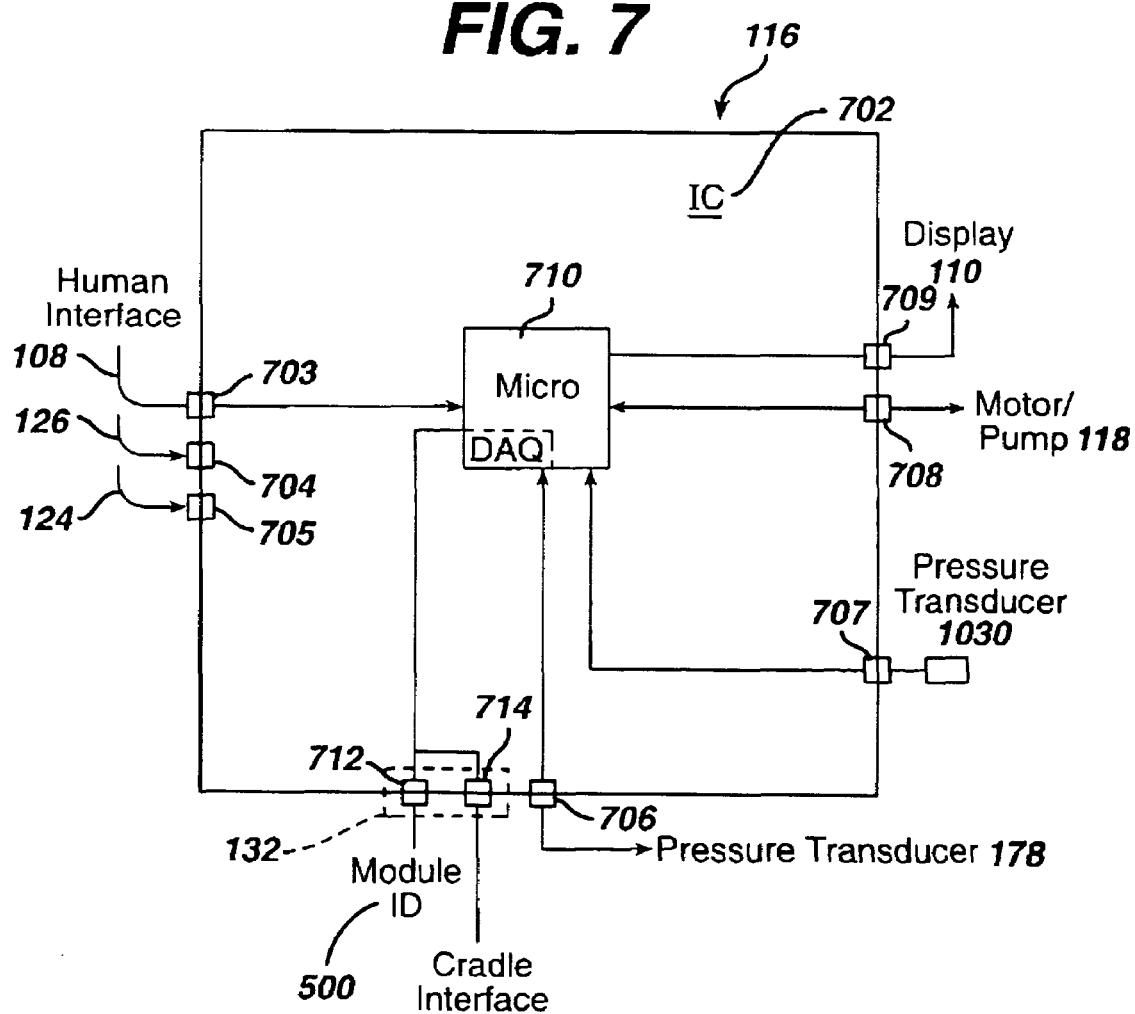

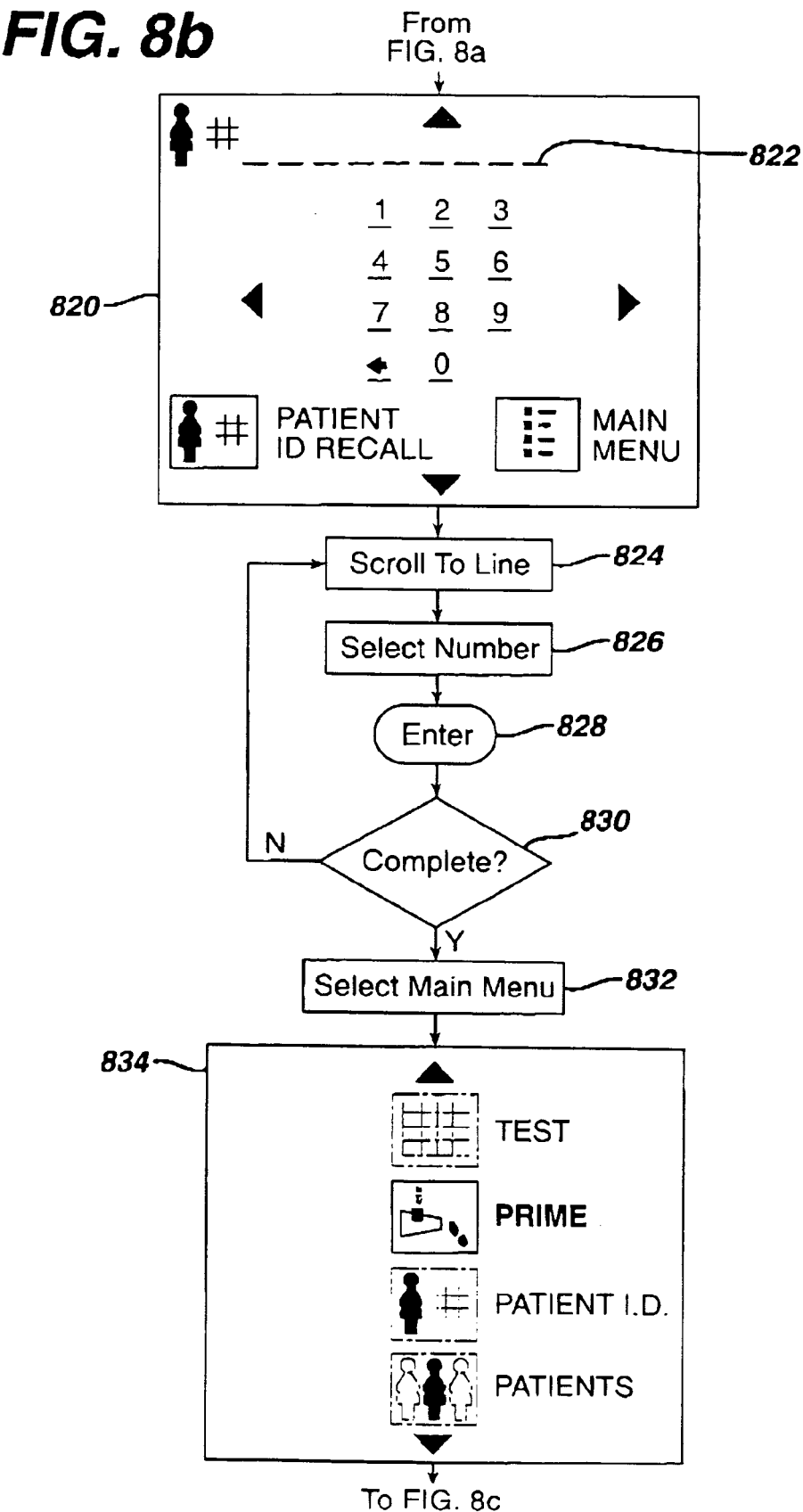

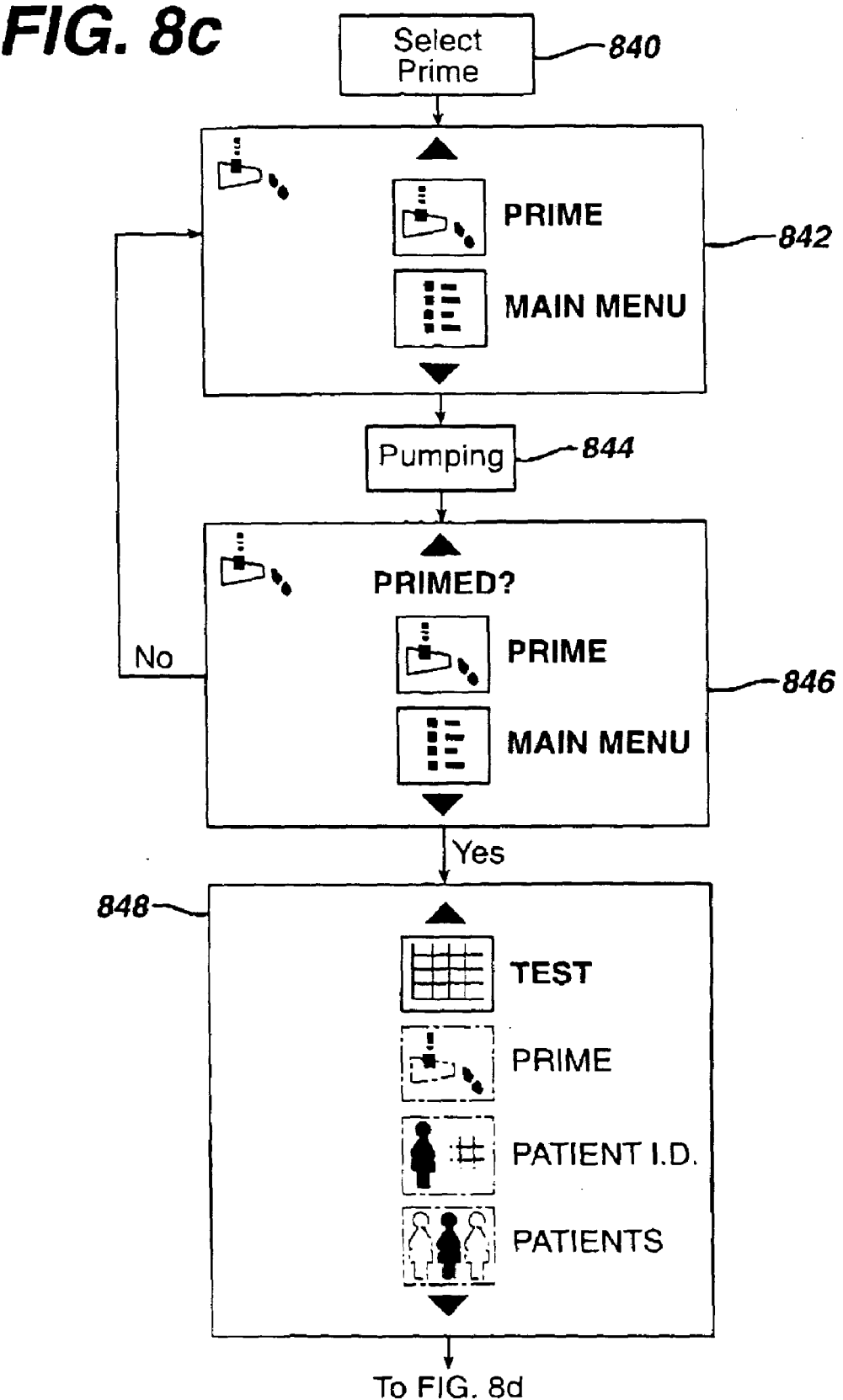

SYSTEM AND METHOD FOR ASSESSING URINARY FUNCTION

CROSS REFERENCE TO RELATED APPLICATIONS

The present invention claims the benefit of earlier filed U.S. provisional patent applications, Ser. Nos. 60/302,069, filed on Jun. 29, 2001 and 60/372,579, filed on Apr. 12, 2002, which are both incorporated by reference in their entirety herein.

FIELD OF THE INVENTION

The present invention relates generally to a system and a method for assessing urinary function. More particularly, the system and method is used for testing the integrity of the urinary system for diagnostic purposes and for use with therapies to correct urinary incontinence.

BACKGROUND OF THE INVENTION

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle, shying away from social situations.

SUI is categorized into three types. Type I and Type II are directed to urethral hypermobility. Type III is directed to intrinsic sphincter deficiency (ISD). Diagnosis of ISD requires urodynamic evaluation. Urodynamic evaluation involves complex and invasive equipment and often requires referral to a specialist trained in urodynamic evaluation.

Existing diagnostic systems all require a catheter be passed trans-urethraly to measure pressure, such as Leak Point Pressure (LPP)—or Urethral Pressure Profile (UPP). An exemplary system is disclosed in publication (WO 0023127). Detection of LPP requires that a pressure sensor and catheter be passed trans-urethrally. The bladder is filled, and pressure is recorded. Fluid leakage from the urethral opening (meatus) corresponds to the maximum pressure the urethral sphincter can resist, or LPP. During the UPP measurement procedure a pressure sensor tipped catheter is placed trans-urethral into the bladder and then withdrawn at a constant velocity. The pressure profile along the urethra, from bladder neck to meatus is recorded.

Other parameters may also be measured, such as abdominal pressure and urinary flow. A cystometrogram (CMG) is a pressure study that simultaneously measures intra-abdominal, total bladder, and true detrusor pressures. Uroflometry measures urine flow rate visually, electronically, or via a disposable system. Video Urodynamic Systems also exist that simultaneously measure parameters, as described above, with radiographic visualization of the lower urinary-tract.

Existing urodynamic evaluation systems are complex, expensive, and require extensive training. Furthermore, existing urodynamic systems often require at least 30 minutes to complete a test. This exceeds the time available for most standard physician office visits and results in referral to a specialist. No urodynamic system exists that can quickly and inexpensively record useful urodynamic measures, without passing a catheter or instrument trans-urethraly.

There remains a need for an improved system and method for assessing urinary function.

SUMMARY OF THE INVENTION

A portable, self-contained medical diagnostic system for assessing urinary function is provided including a control device including a processor, a pump device, and a pressure sensor, and a test module removably coupled to the control device. The test module includes a pressure interface and a tubing assembly defining a first fluid conduit between a first fluid inlet and a first fluid outlet, wherein the pump device is coupled with the first fluid conduit for pumping fluid therethrough. The system further includes an insert member having a first channel therethrough and coupled to the first fluid outlet so that fluid flowing through the first fluid conduit may flow through the first channel, the insert member being dimensioned for insertion into a patient's bladder through the patient's urethral canal, such that, when the insert member is inserted into the patient's bladder, the pressure interface is in fluid communication with the bladder such that a pressure at the pressure interface substantially corresponds to a pressure within the bladder. The pressure interface is further positioned relative to the pressure sensor so as to transmit bladder pressure information thereto.

Also provided is a medical diagnostic system including a control device including a processor and pump device electrically coupled to and controlled by the processor, a test module removably coupled to the control device and including a tubing assembly having a first fluid inlet, a first fluid outlet, and a first fluid conduit extending therebetween, and an insert member coupled to the tubing assembly fluid outlet and having a channel therethrough in fluid communication with the first fluid conduit. The insert member is dimensioned for insertion into a patient's bladder through the patient's urethral canal. The system also includes a pressure detection system for detecting pressure correlating to a pressure within the bladder. The pump device is coupled to the first fluid conduit to thereby be capable of pumping fluid through the first fluid conduit and insert member channel and into the bladder, and the pressure detection system is capable of detecting the pressure within the bladder as fluid is pumped therein.

A method is also provided for assessing urinary function including the steps of removably coupling a test module to a control device to form a portable, self-contained diagnostic system, wherein the control device includes a processor, a pump device and a pressure sensor, and the testing module includes a fluid tubing assembly having a first fluid inlet, a first fluid outlet and a first fluid conduit extending therebetween. The method further includes the steps of coupling to the first fluid outlet an insert member having a channel therethrough in fluid communication with the first fluid conduit, coupling the first fluid inlet to a fluid source, inserting the insert member into a patient's bladder through the patient's urethral canal, activating the pump device to thereby infuse fluid from the fluid source through the first fluid conduit and insert member channel and into the bladder; and measuring pressure within the bladder as fluid is infused therein.

The present invention also provides a self-contained medical diagnostic system for assessing urinary function including a control device including a processor, a pump device electrically coupled to and controlled by the processor, and a first pressure sensor, and a testing module removably coupled to the control device. The testing module further includes a first fluid conduit extending between a first fluid inlet and a first fluid outlet, and a second conduit having a first open end and a first pressure interface in fluid communication therewith. The system also includes a first insert member having first and second channels therethrough, the first channel being in fluid communication with the first fluid conduit and the second channel being in communication with the second conduit. The insert member is dimensioned for insertion into a patient's bladder through the patient's urethral canal. The pump device is coupled to the first fluid conduit for infusing fluid through the first fluid conduit, the first insert member channel and into the bladder, and the first pressure interface and first pressure sensor are positioned relative to one another so that the first pressure interface transmits pressure information to the first pressure sensor.

BRIEF DESCRIPTION OF THE DRAWINGS

FIG. 4b is a rear perspective view of the pole attachment mechanism of FIG. 4a;

FIG. 5a is a schematic cross-sectional view taken across line 5a—5a of FIG. 5 prior to engagement of the control device with the test module;

FIG. 5b is a schematic cross-sectional view similar to FIG. 5a showing engagement of the control device with the test module;

FIG. 6 is a front perspective view of a module according to the present invention;

FIG. 7 is a schematic illustration of one embodiment of control device electronics assembly;

FIGS. 8a–8i are flow diagrams illustrating operation of control device software and graphical user interface components;

DETAILED DESCRIPTION OF THE EMBODIMENTS

FIGS. 1 through 26 illustrate generally various systems and methods for assessing urinary function and/or components of such systems and methods. Although the systems and methods disclosed herein are described in detail in relation to the female urinary system, it is to be understood that the present invention can readily be adapted for use in assessing male urinary function as well. Further, those skilled in the art will recognize that inventive principles, apparatus and methods disclosed herein may also have application to assessing function in other areas, such as coronary function or pulmonary function. The present invention is to be limited only by the claims set forth herein.

Figure 1:
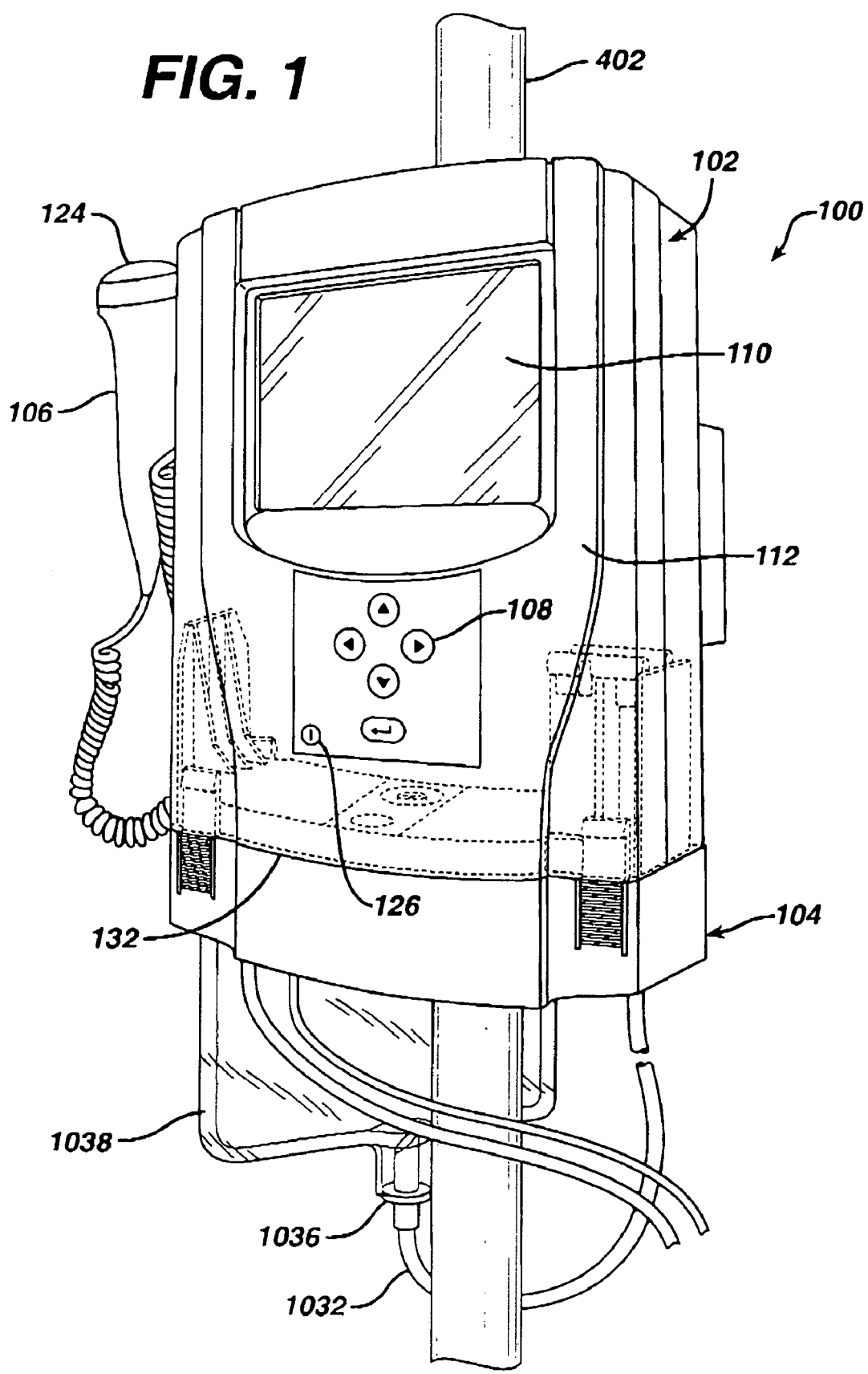
FIG. 1 is a perspective view of a one embodiment of a portable medical system according to the present invention.
Figure 1A:
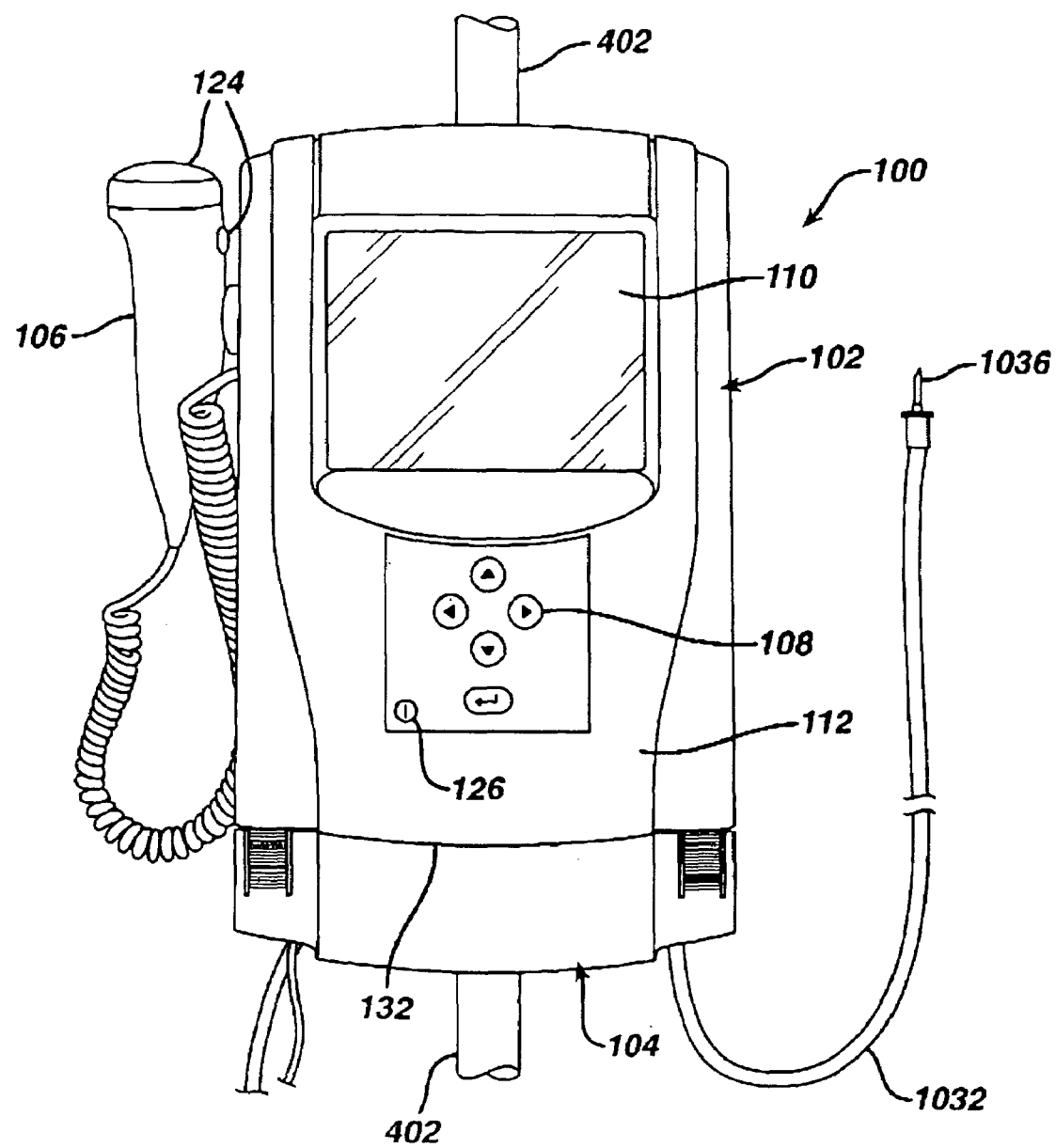
FIG. 1a is a front view of one embodiment of a portable medical system according to the present invention.
Figure 2:
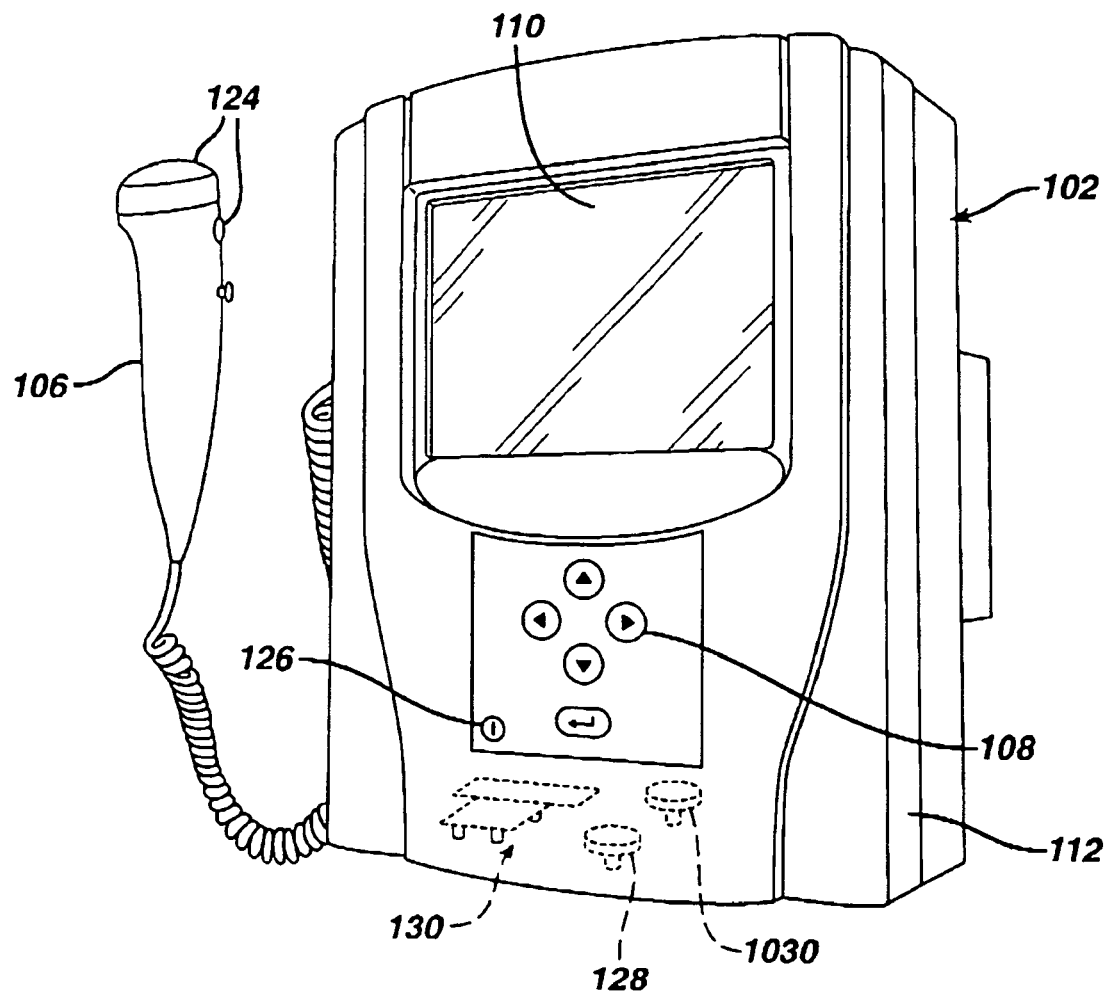
FIG. 2 is a front perspective view of a control device according to the present invention.
Figure 3:
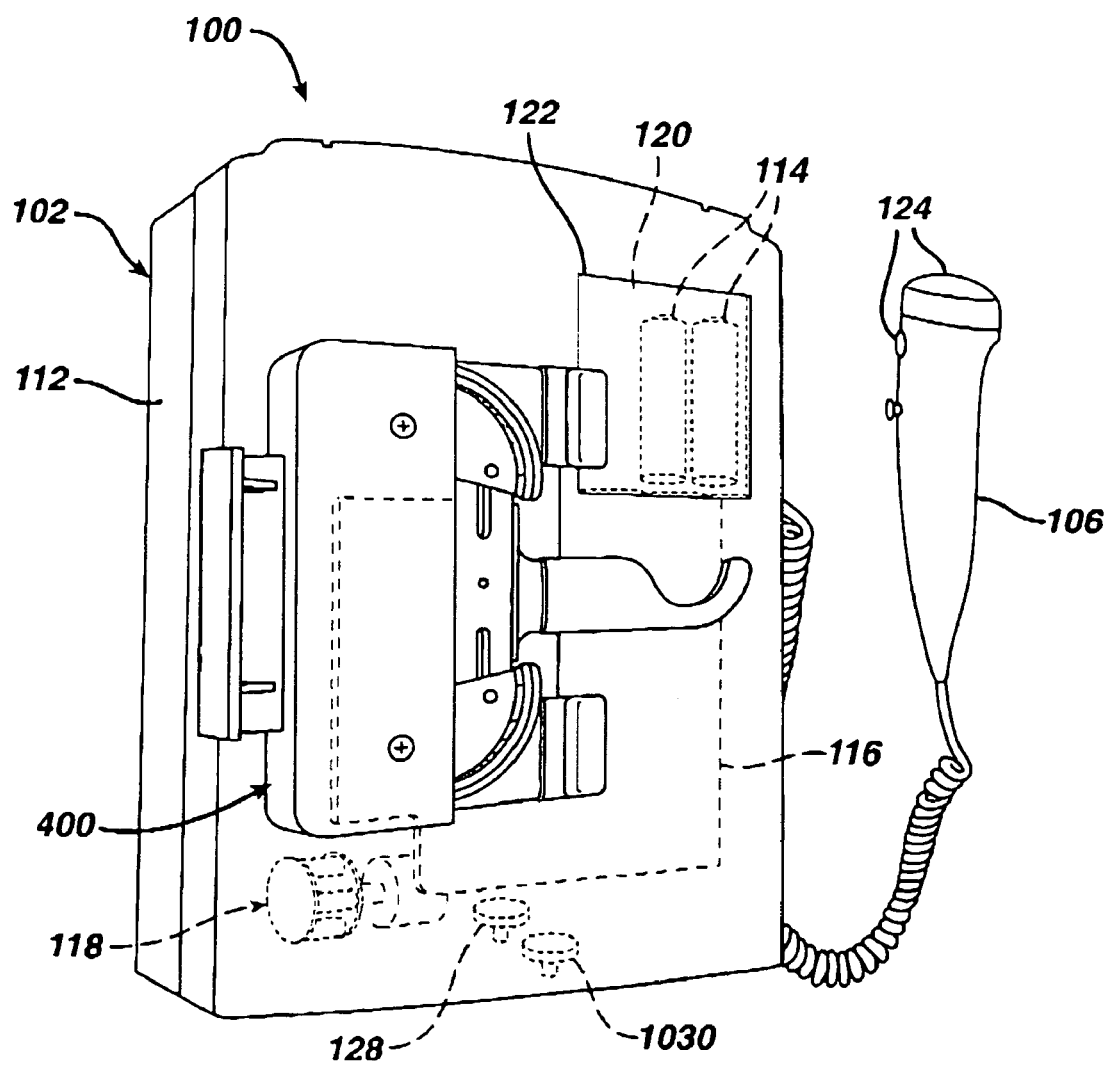
FIG. 3 is a rear perspective view of the control device of FIG. 2.

Referring now to FIGS. 1 and 2, one embodiment of a portable medical system 100 is illustrated having particular application for assessing urinary function. The system 100 includes a control device 102 that controls operation of the system, at least one module 104 that can be removably coupled to the control device, at least one input device, such as the illustrated input pendant 106 and/or keypad 108, and at least one output device, such as the illustrated display screen 110. As will be described in more detail below, the control device 102 is designed to be removably coupled to any one of a plurality of testing modules 104 at any given time. As each module is uniquely suited to support a different type of diagnostic test or medical procedure, the resulting diagnostic system is not only readily portable, but is also extremely versatile in that the single control device, in conjunction with a plurality of small test modules, is capable of performing an array of diagnostic tests or other procedures. The system has particular application useful for assessing urinary function in that it provides a portable, modular system in contrast to the non-portable, expensive, and cumbersome equipment that is currently used for assessing urinary function. In addition, as will also be described in greater detail below, the present invention can perform tests quicker, and in a manner that is less uncomfortable and less invasive for a patient.

Figure 4:
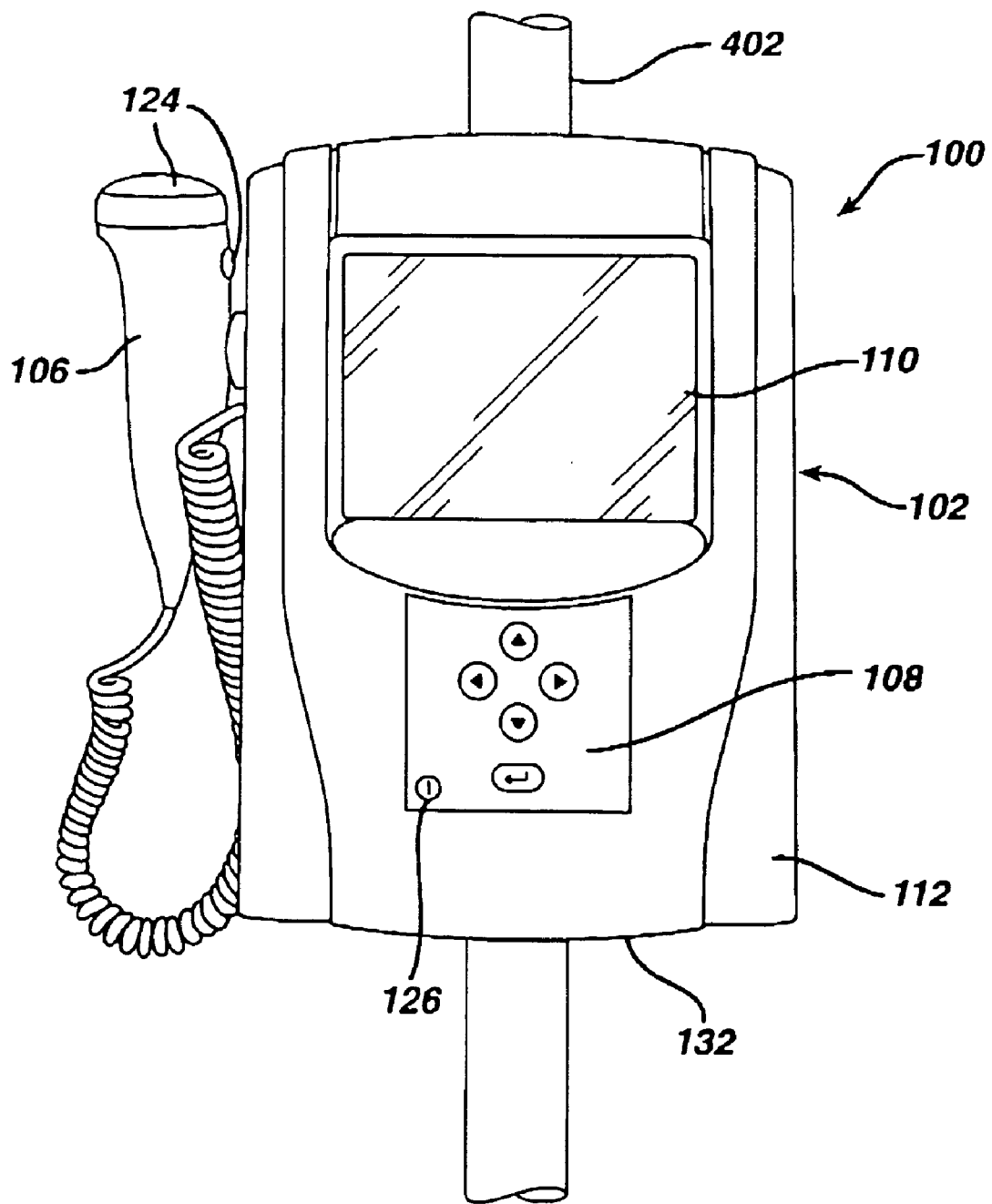
FIG. 4 is a front elevational view of a control device in accordance with the present invention attached to a pole.
Figure 4A:
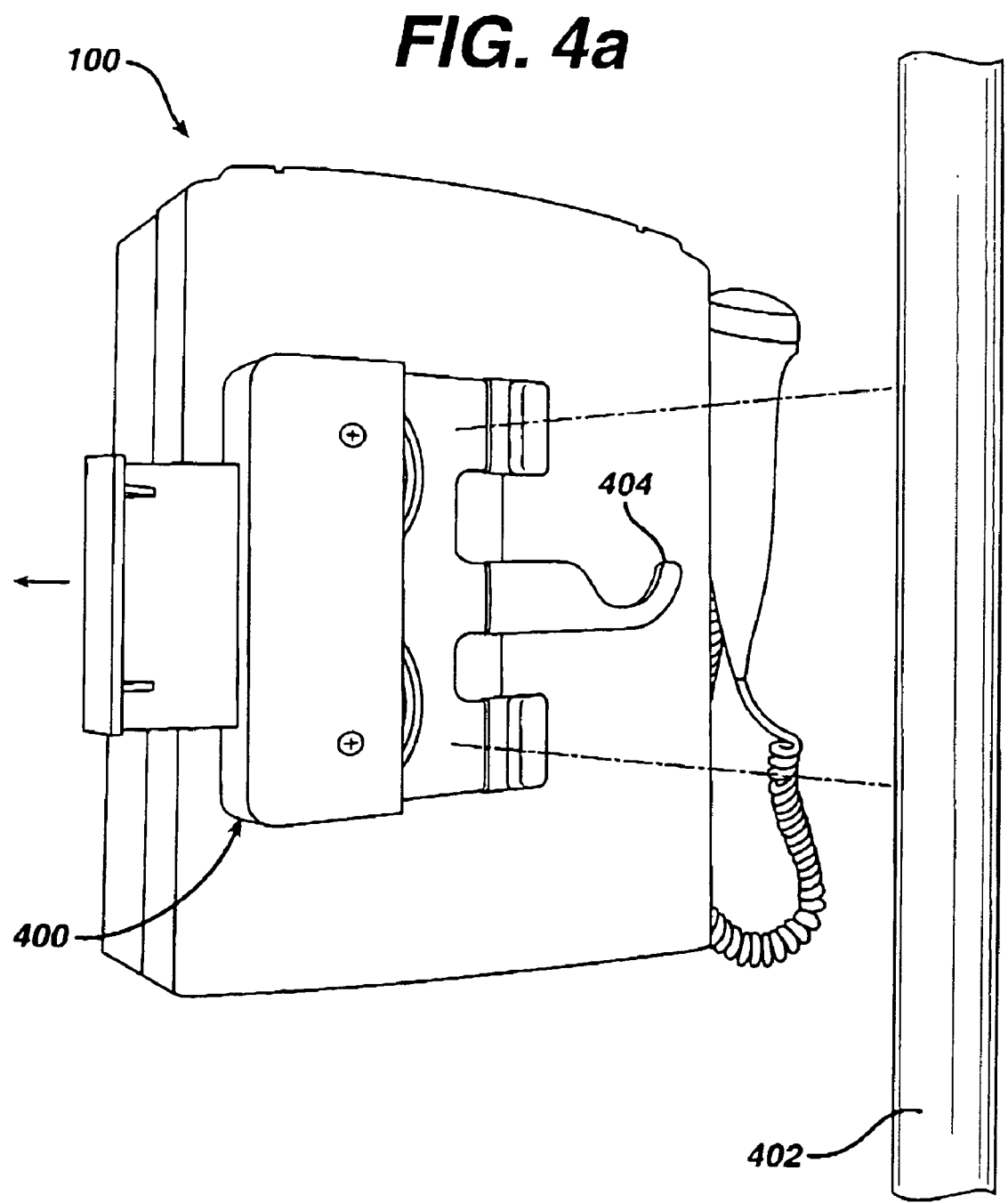
FIG. 4a is an exploded perspective view of one embodiment of a pole attachment mechanism.
Figure 4B:
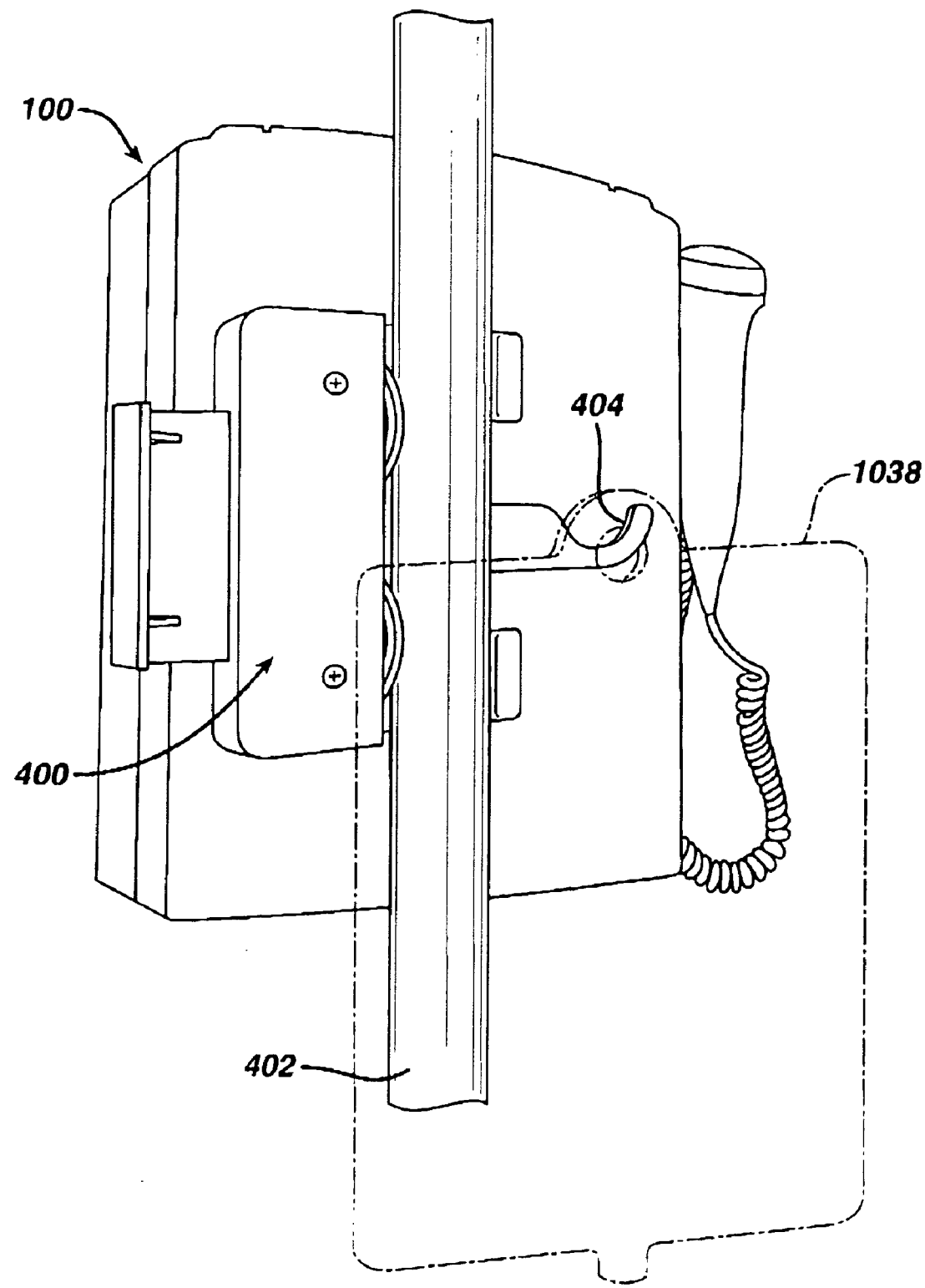
Figure 4C:
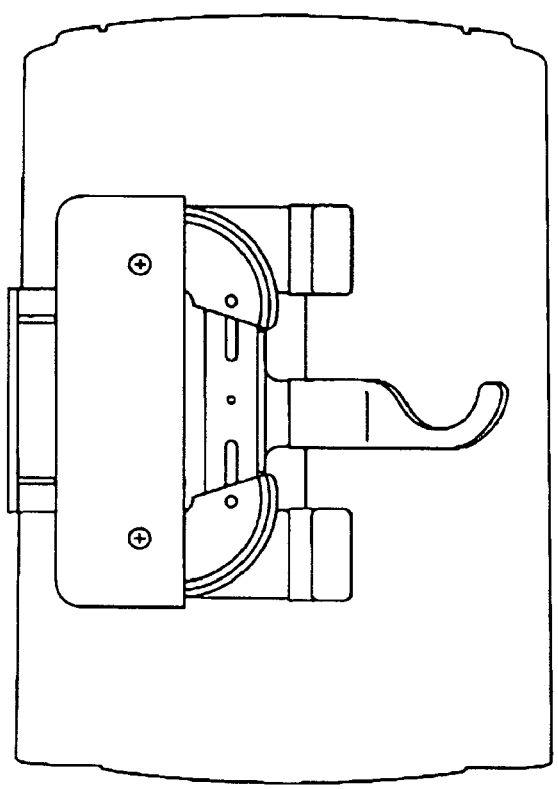
FIG. 4c is a rear view of the pole attachment mechanism of FIG. 4a when not secured to a pole.
Figure 4D:
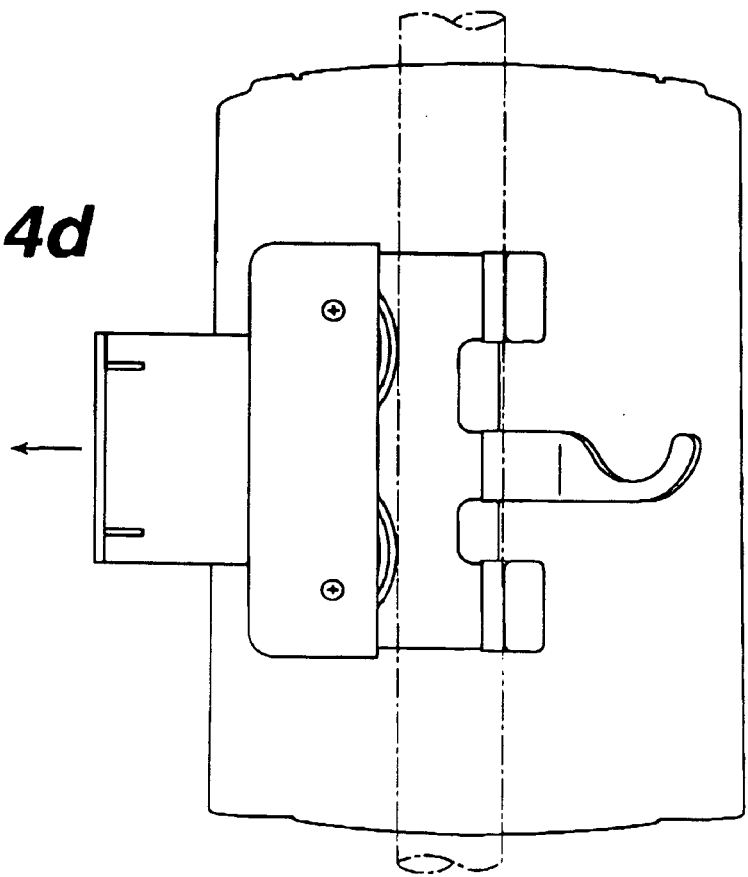
FIG. 4d is a rear view of the pole attachment mechanism of FIG. 4a when secured to a pole.
Figure 5:
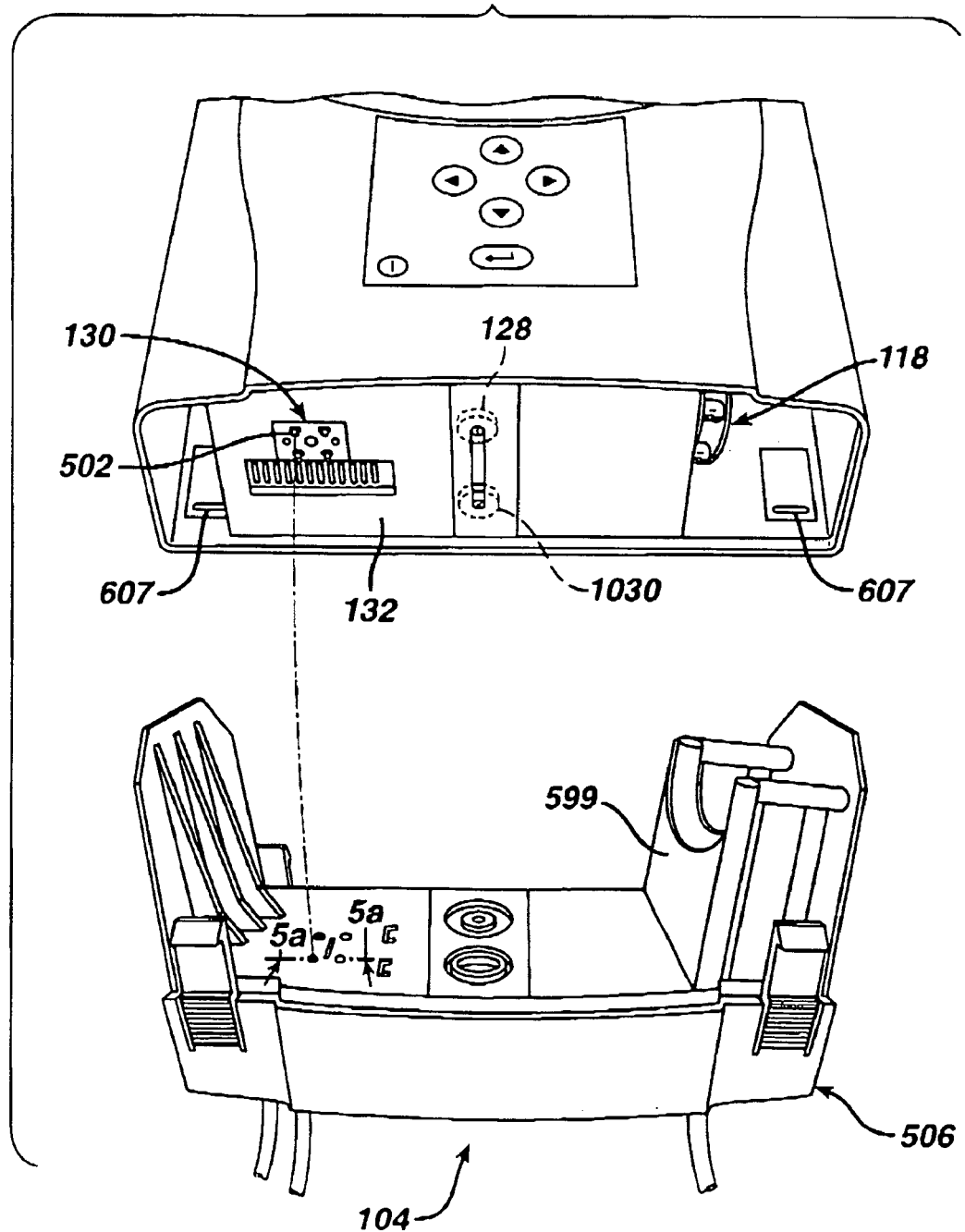
FIG. 5 is an exploded perspective view illustrating interaction of a control device identification mechanism and module identification components.

The control device 102 includes a housing 112 for housing various components, including one or more batteries 114, an electronics assembly 116, a pump device 118 including a motor, and various other circuitry. Batteries supply power to the control device 102, and are contained within a battery compartment 120 that is accessible by removing the battery cover 122 that forms part of the housing 112. The control device further includes an input keypad 108 for allowing a user to input data (such as patient name or other identifier, numeric identifiers, patient history, date etc.) and an input pendant 106 including one or more switches 124 that allow user input of additional information (i.e., event input based on patient feedback), and an activation switch 126 for turning the device on and off. The pump device 118 and at least one pressure transducer 128 are also contained within the housing. The pump device is electrically coupled to the battery and the electronics assembly, and the pressure transducer is electrically coupled to the electronics assembly. The control device 102 may also include a pole mounting mechanism 400 for mounting the control device on a pole such as the pole of an IV solution caddy 402 including a hook 404. One embodiment of a pole mounting mechanism is illustrated in FIGS. 4*a* and 4*b*. The device may also include an interface 130 including appropriate electrical pinouts to enable the control device to communicate for purposes of battery recharging or printing of patient test data.

As indicated above, any one of a plurality of modules 104, such as diagnostic test modules, can be removably coupled to the control device 102, and the control device is designed to uniquely identify the attached module, and perform routines specific to that module. Thus, the control device includes a module detection mechanism 500 capable of identifying the attached module that is electrically coupled to the electronics assembly (see FIG. 5). This module detection mechanism includes one or more identification probes 502 that project from the interface side 132 of the control device and are electrically coupled to the electronics assembly. The modules 104 may include one or more apertures in the module housing 506 that are designed to receive therein the identification probes when the module is removably coupled to the control device. When so coupled, the identification probes will bridge one or more module identification elements or components 504, such as resistors, capacitors, fuses or other suitable electronic components, present within the module. The identification probes are electrically coupled to the electronics assembly 116 (described more fully below), which determines a value, such as resistance, associated with the module identification element(s) that they bridge. Each module is designed to have a value so that identification of this value by the electronics control assembly enables the control device to uniquely identify the attached module. In a preferred embodiment, the control device may include one or more sets of identification probes 502 at different locations, and different modules have a module identification components 504 at different locations. The location, as detected by the control device, identifies the attached module. In yet another embodiment, the module identification component(s) may be coupled to an exterior side of the module housing so that apertures in the module housing are not required.

The module further includes at least one coupling element 600 for removably coupling the module to the control unit (see FIG. 6). In the illustrated embodiment, the module includes four coupling elements placed toward the ends of each of the front and rear faces 602, 604 of the test module. Each coupling element contains a tab element 606 that engages a corresponding ridge 607 (best seen in FIG. 5) on an interior surface of the control device when the module is removably coupled to the control device. To couple the module to the control unit, the coupling elements are depressed slightly in the direction indicated by the arrow in FIG. 6.

The module is then aligned with the control device as shown in FIG. 1, and the coupling elements released to allow engagement with the corresponding ridges described above. The module can subsequently be removed from the control unit by once again depressing the coupling elements and removing the module from the control device.

Finally, the module housing 506 includes first 608 and possibly second 610 ports therein as shown in FIG. 6. Each of the first and second ports are configured so as to define a recess capable of receiving a control device pressure sensor, such as a pressure transducer, therein when the module is coupled to the control device. For example, a first control device pressure transducer 128 is received within the first port recess 608 and comes in physical contact with a pressure interface 1024 (see FIG. 10) so that pressure changes at the pressure interface can be transmitted to and detected by pressure transducer 128 and converted to electrical signals that are sent to the electronics assembly for interpretation. Similarly, the second port 610 also defines a recess capable of receiving therein a second control device pressure transducer 1030. The first and second ports are further configured to form an airtight seal with the control device when coupled thereto, preferably by incorporating sealing elements such as gaskets or the like. Individual modules and their operation in conjunction with the control device will be described in greater detail below.

As indicated above, contained within the housing 112 of the control device 102 is an electronics assembly 116 (see FIG. 7) that is designed to control operation of the pump device 118, to acquire and format data from the pressure transducer(s), to drive a display 110 and/or other output device, and to accept and interpret input data, such as from switches 108, 126, and/or 124. The electronics assembly 116 consists of an integrated circuit board 702, hardware interfaces to the pump device 708, pressure transducer 706, 707, display 709 and switches 703, 704 and 705; and a microprocessor 710. The microprocessor 710 serves as the main controller for the diagnostic system and is supported by the custom integrated circuit 702 and powered by the batteries. Also included are interface connection elements including an electronic module identification connection 712 to the electronic detection mechanism 500, and electronic connections 714 that enable downloading of data to a printer or other external device.

The microprocessor 710 is programmed with a custom program file. In the illustrated embodiment, this software has multiple functions. First is the acquisition of input from the operator. This input data is captured from the input keypad 108, and/or switches 124, 126, pressure transducer(s) or other input device, depending upon which test module is in use. The software also controls operation of the pump device 118. Input data is interpreted and appropriate signals are sent to the pump device motor via the integrated circuit board 702. Yet another function is to acquire and condition data from the pressure transducer(s). This data is then sent in the appropriate format to the display 110, along with applicable pump device data in the form of volume or time information. Finally, as indicated above, the software receives input from the module detection mechanism 500 and interprets this input to determine which test module is coupled to the control device.

FIG. 8a–8i are flow diagrams illustrating operation of the diagnostic system software and features of the system graphical use interface for a preferred embodiment of the invention. When the system is powered on, the user is first presented with a welcome screen. While this screen is being displayed the system is undergoing a self-test routine 802 to test the integrity of system hardware and software components. Upon completion of this routine, the user is provided with information relating to the amount of available system memory 804. Following the pressing of any key 806 on input device 108 by the user, the system identifies the attached module 808 as described above, and following such identification, the processor executes a software subroutine specific to the identified module. For each software subroutine, however, a main menu is displayed next, such as that indicated by reference numeral 810. In the illustrated embodiment, the main menu includes six possible selections. "Utilities" enables the user to access various system features, such as setting the date, time etc, or adjusting the brightness or contrast of the screen; "Quit" terminates the session; "Patients" enables the user to access any previously stored data relating to other patients and tests already performed; "Prime" initiates the pump priming process; "Patient ID" enables the user to enter a patient identification number; and "Test" initiates a software subroutine specific to the attached module to carry out the desired test procedure. In the presently described embodiment, the software and user interface associated with the "Prime," "Utilities," "Quit," and "Patient ID" selections are substantially the same for each software subroutine. The "Test" and "Patients" selections, however, are different for each test module. Each of these selections will be described in greater detail below.

Figure 8A:
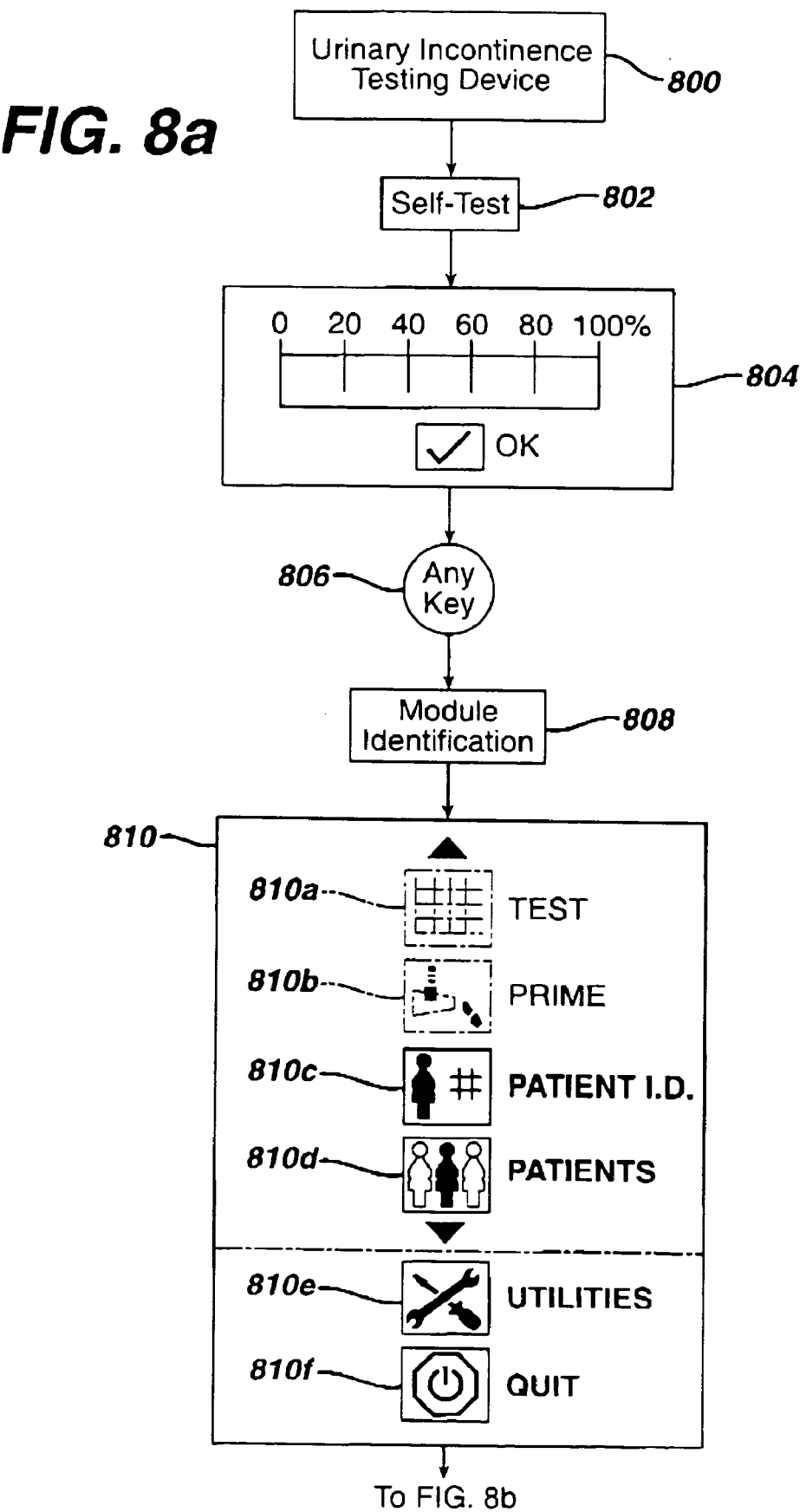

As is illustrated in FIG. 8a, the first time the main menu is displayed both "Test" and "Prime" appear in a different color or shade from the other options, indicating that they are not currently available. This is to ensure that patient identification information is entered before proceeding with any priming or testing procedures. The user may select the "Patient ID" option by scrolling using the appropriate arrows on the input keypad 108. Following this selection the Patient ID screens appears 820 (FIG. 8b). In the illustrated embodiment, the patient ID consists of a nine digit integer. To enter the patient ID, the user scrolls to a selected blank using the left and right arrows and/or left and right arrows on the input keypad 108 (824) to select desired numbers. Once the desired number is selected, the user presses ENTER; the selected number will then appear in the rightmost blank. Subsequent numbers are selected as described above, and will appear in the rightmost blank while previously selected numbers move to the left. This process is completed until all blanks are filled in. In one embodiment, there is a default value for each blank, such as 0, and the user may proceed with testing by accepting the default patient ID number consisting of all 0's. Once complete patient identification information is entered, the user selects the "Main Menu" option 832, which returns to the main menu screen. At this point, however, the "Prime" option become available 834 (and "Patient ID" is no longer available).

Before performing any test that requires fluid to be infused into the patient, priming operations must be performed to ensure that the fluid infusion lines (tubing) are filled with fluid and not air. Referring now to FIG. 8c, the user selects the "Prime" option 840 by using the arrow keys to select the option, and then pressing the enter key. The Prime screen then appears. According to one embodiment, the Prime screen includes two options as indicated at 842: "Prime" or "Main Menu." In another embodiment, the Prime screen is particular to each module, and may present only one option to initiate priming. Selecting the Prime option causes the pump to start and run for a predetermined amount of time, such as 20 seconds, and then automatically shuts off. The user is then presented with a screen 846 at which the user can accept the prime as complete (MAIN), or choose to reprime (PRIME). When priming is accepted as complete, the main menu once again appears, this time with "Test" as an option 848. In another embodiment, priming operations may be specifically tailored for different test modules. For example, as will be described in more detail below, the SUI test modules includes a hand actuator including an activation button 1118 or 1128. The system may be designed so that following display of the Prime screen, pump priming operations can be initiated by depressing the activation button.

With priming complete, testing can begin. As indicated above, testing procedures depend on the attached test module, and accordingly, the software and graphical user interfaces relating to each test module will be discussed in greater detail below in conjunction with the detailed description of each test module.

Figure 9:
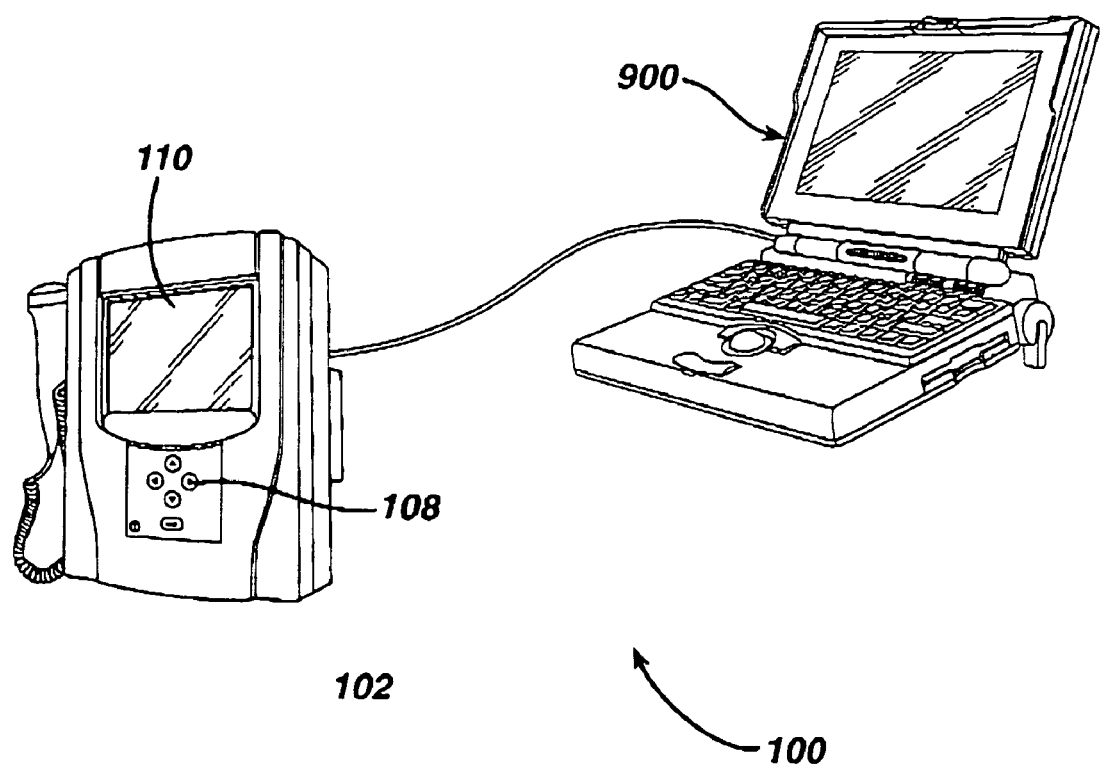
FIG. 9 is an alternate embodiment of a medical system according to the present disclosure;—

In an alternative embodiment of the invention illustrated in FIG. 9, the control device 102 is electrically coupled to a laptop/standard computer 900, and the microprocessor and associated software reside in the computer.

As indicated above, the diagnostic system described herein has particular application to urodynamics in that it enables clinicians to diagnose a plurality of urinary incontinence problems when used with specifically designed testing modules (to be discussed hereinafter). As a miniaturized urodynamic tool, the control device 102 in conjunction with modules 104 can measure urethral resistance pressure (URP), voiding flow (Uroflometry), and bladder dysfunction (Cystometrogram (CMG)). As will be described further below, URP is a new and unique approach to urodynamic measurement of stress incontinence that is less invasive for a patient, and faster than currently known and used diagnostic tests. Uroflometry is the study of micturation over time. CMG is the study of bladder or detrusor instability. A major advantage of the diagnostic system disclosed herein is that it can achieve all of the diagnostic tests described above with a portable unit that can be used in any office exam room, removing the need for the reservation or scheduling of a specialized urodynamic room, and the need for the complex equipment currently required for such tests. The urodynamic system is easy to use and does not require advance training. Use of the disclosed system makes testing more comfortable for patients by enabling faster set up, shorter test time, and less invasive procedures.

In actual use, different modules can be removably coupled to the control device 102 to conduct these different urodynamic tests. Each module performs a different and distinct test. These modules include, but are not limited to, a stress urinary incontinence (SUI) module for measurement of urethral resistance pressure (URP); a simple CMG module for measurement of bladder instability; a complex CMG module for measurement of bladder instability; and a uroflometry module for the study of micturation over time. Modules may be suitably adapted to either male or female incontinence diagnosis.

Figure 13:
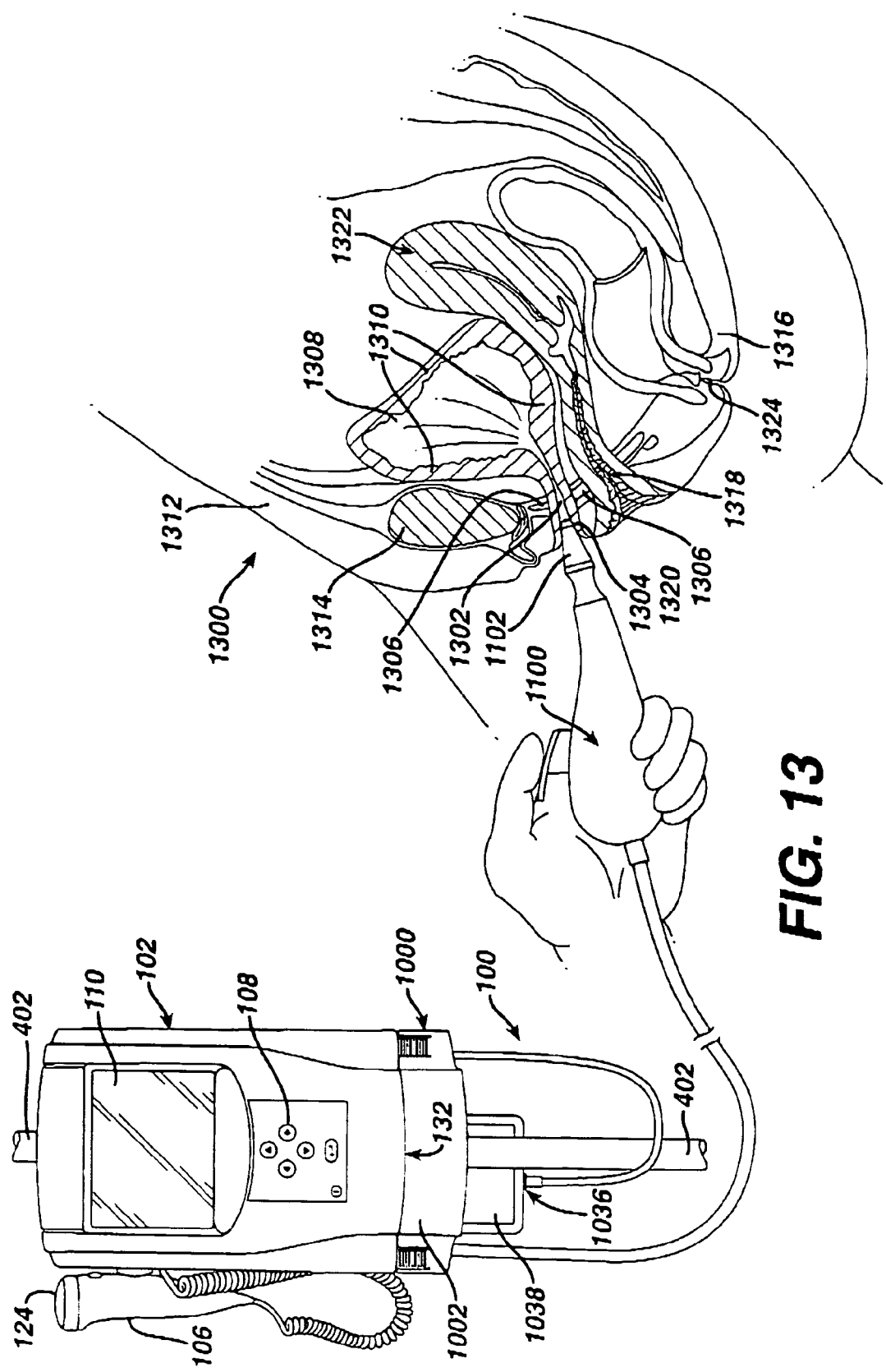
FIG. 13 is a schematic view of illustrating one embodiment of a urodynamic system in relation to a female urinary/reproductive system.

Before proceeding with a discussion of individual test modules, to assist the reader a brief overview of the female urinary system will be described with reference to FIG. 13. The female urinary system 1300 includes an elongated urethral canal 1302 having a urethral meatus (entrance) 1304 and having a substantially circular-shaped urethral sphincter muscle 1306 attached thereto, and a bladder cavity 1308 surrounded by a detrusor muscle 1310. The detrusor muscle 1310 also surrounds and supports the urethral canal 1302. The bladder cavity 1308 is in close proximity to the abdominal wall 1312, the pubis bone 1314, the pelvic floor 1316 (levator ani muscle), the vaginal canal 1318, the clitoris 1320, the uterus 1322 and the anal sphincter muscle 1324.

Individual testing modules will now be described in detail.

STRESS URINARY INCONTINENCE MODULE

FIGS. 10–13 illustrate one embodiment of a stress urinary incontinence testing module (SUI) 1000 for diagnosing the involuntary loss of urine during physical activities such as coughing, sneezing, laughing or lifting. The SUI testing module 1000 includes a SUI module housing 1002 that can be removably coupled with the control device 102 as described above The module housing may be in the form of a plastic disposable cartridge. Within the module housing is a tubing assembly 1004 including a fluid inlet 1006, a fluid outlet 1008, and a first fluid conduit 1010 extending therebetween. Tubing loop 1012 forms part of the tubing assembly and is positioned so that, when the SUI testing module is coupled to the control unit, the stator 1014 of the pump device 118 in the control unit 102 cooperates physically with the tubing loop 1012 so that the pump device operates as a peristaltic pump to pump fluid through the first fluid conduit 1010. To assist in this regard, a tubing guide 599 aids in positioning a portion of the tubing assembly so that it will properly and effectively engage the peristaltic pump. According to the illustrated embodiment, tubing guide 599 has a substantially U-shaped configuration, however, many other configurations are suitable, as the principles of operation of peristaltic pumps are well known in the art. Tubing member 1050 also forms part of the first fluid conduit. The module housing 1002 also includes a pressure chamber 1016 for dampening pressure fluctuations that may be caused by operation of the pump device. The pressure chamber 1016 is in fluid communication with the first fluid conduit 1010 via valve openings 1018a–c of three-way valve member 1020. The pressure chamber is filled primarily with air, but varying amounts of fluid may also be present. Positioned at a distal end of pressure chamber 1016 is a filter component 1022 designed to isolate fluid from electronic elements of the system 100. In this regard, filter 1022 may be a hydrophobic filter that allows air to pass into pressure interface 1024, but not liquid. When the testing module is coupled to the control device 102, pressure interface 1024 is in physical contact with pressure transducer 128 of the control device so that pressure fluctuations within the pressure chamber 1016 and pressure interface 1024 can be transmitted to and sensed by the pressure transducer, and subsequently transmitted to the electronics assembly as indicated above. In this manner, the control device measures pressure within the first fluid conduit of the tubing assembly of the SUI testing module, which substantially corresponds to the pressure within the urethral canal as described more fully below.

The SUI testing module 1000 tubing assembly also includes a second tubing member 1025 having a channel therethrough forming a second fluid conduit between a proximal end 1026 and a distal end 1028.

Figure 11A:
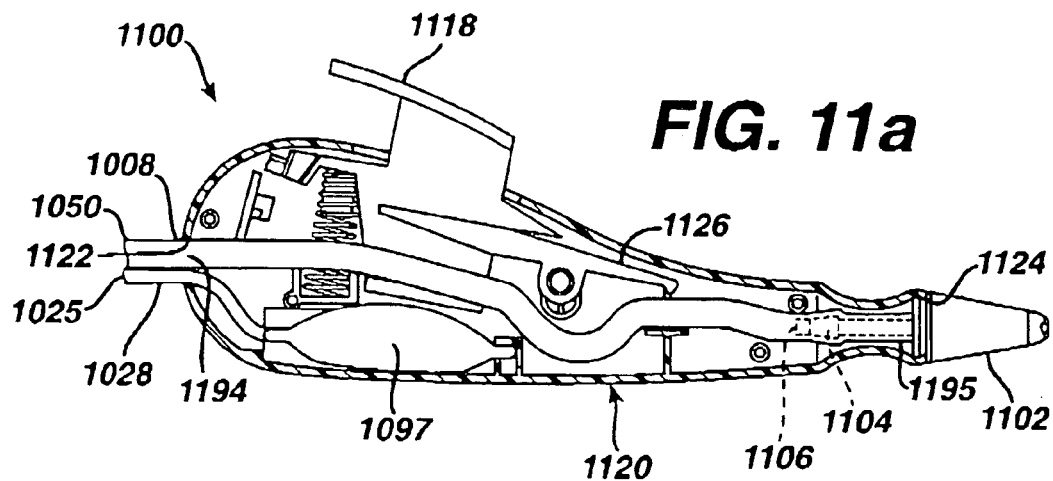
FIG. 11a is a side elevational view and partial cross-section of one embodiment of a hand actuator in an assembled configuration.
Figure 11B:
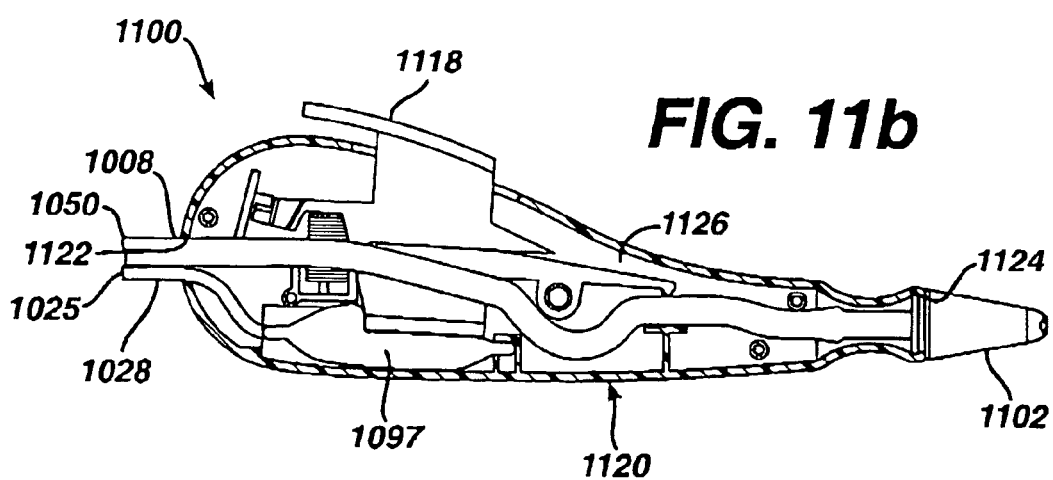
FIG. 11b is a side elevational view and partial cross-section of the hand actuator of FIG. 11a in an unassembled configuration.
Figure 11C:
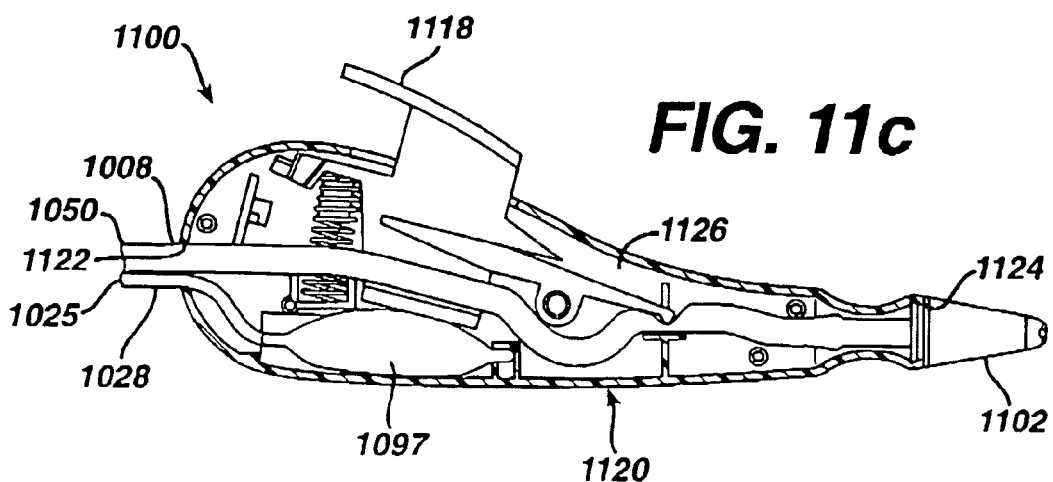
FIG. 11c is a side elevational view and partial cross-section of the hand actuator of FIG. 11a in an operational mode.
Figure 11D:
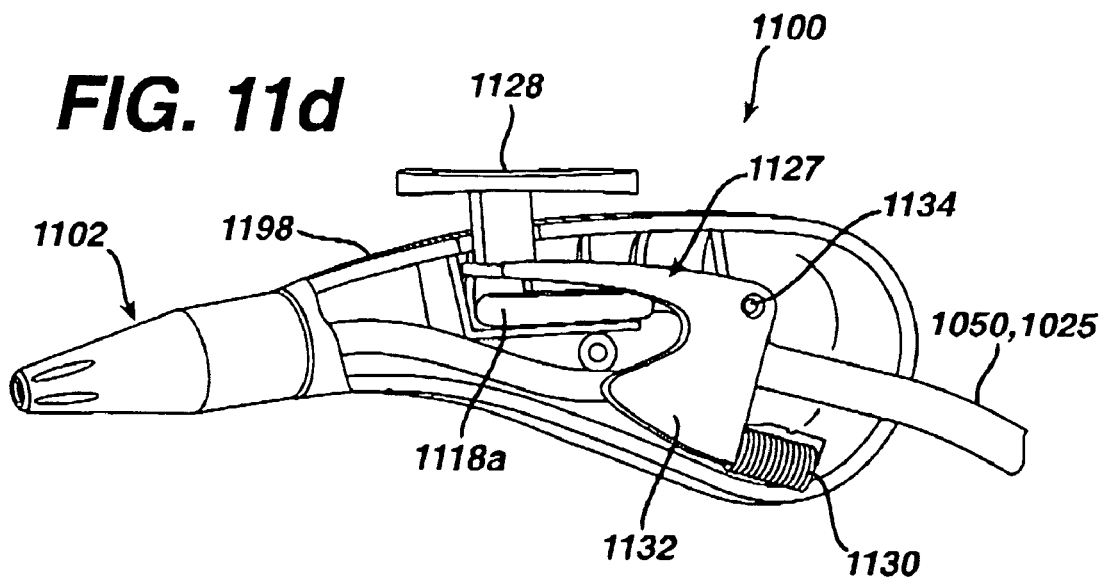
FIG. 11d is an alternative embodiment of a hand actuator according to the present invention.
Figure 12:
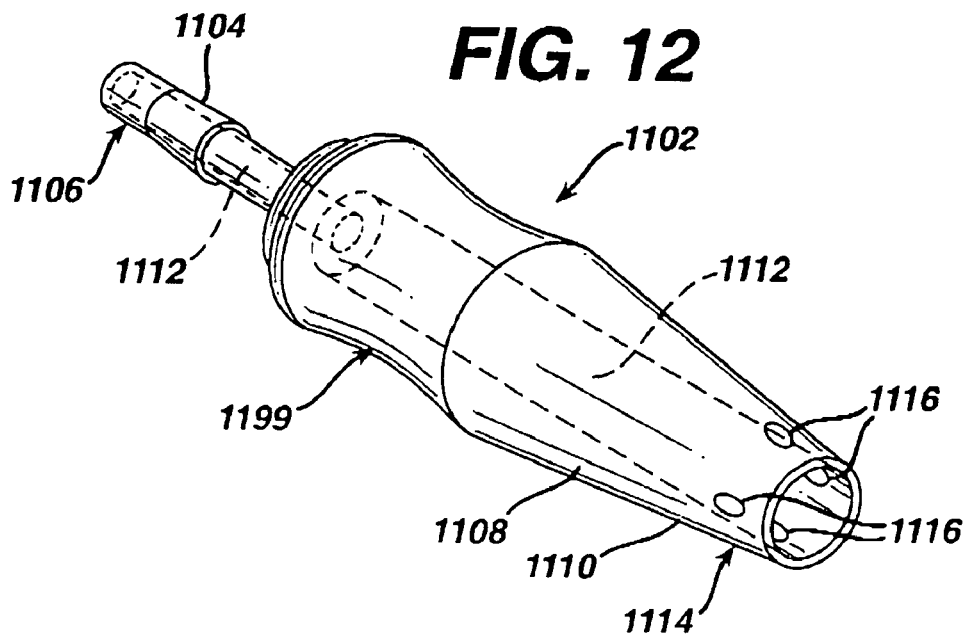
FIG. 12 is an enlarged perspective view of one embodiment of a meatus plug device.

Referring now to FIGS. 11a–c, the SUI testing module may also include a hand actuator 1100 having and insert device such as a meatus plug device 1102 attached thereto. The meatus plug device 1102 (see FIG. 12) includes an attachment member 1104 at a proximal end 1106 coupled to a plug or insert element or member 1108 at a distal end 1110, and a channel 1112 extending therethrough allowing fluid flowing through the first fluid conduit to flow through the meatus plug device. The distal end 1114 of the plug element may also include one or more transversely aligned apertures or openings 1116 therein approximately equally spaced apart from one another around the exterior surface of the distal end. As the outer diameter of the distal end at the location of the apertures is less than the diameter of the inner wall of the urethral canal at that location (described more fully below), one or more of the apertures 1116 can be used for assurance of fluid flow into the urethra during actual operation.

In one embodiment, the hand actuator further includes a hand-sized housing or casing 1102 including therein an initiator element 1118 (FIGS. 11a–c) that is in fluid communication with tubing member 1025. Preferably, initiator element is an air bladder 1097 coupled to a distal end 1028 of the tubing member 1025. The proximal end 1026 of tubing member 1025 coupled to a pressure interface 1026a that is positioned so that, when the SUI testing module is coupled to the control device, pressure within tubing member 1025 can be sensed by pressure transducer 1030. As a closed system, pressure on the activation button 1118 can be sensed at the pressure interface 1026a by pressure transducer 1030, and interpreted by control device 102 as a signal to initiate and/or deactivate the test.

The hand actuator 1100 further includes a fluid conduit 1050 extending between an outlet 1195 and an inlet 1194 that is coupled to (integrally or otherwise) an external tubing conduit leading to a fluid source, such as the first fluid conduit 1010 of the SUI test module. Alternatively, the hand actuator may be designed to include therein the fluid source.

The fluid outlet 1195 is in fluid communication with the insert member channel of the meatus plug device. An activation device 1127 including a trigger 1128 extends through an opening 1118*a* to an exterior of the casing. The activation device 1127 is movable between a first rest position (shown) and a second activated position. In the first position spring 1130 exerts force on coupling member 1132, causing it to pivot relative to pivot element 953 and pinch the distal ends of at least tubing member 1050 to prevent fluid flow therethrough. When in the second position, movement of the trigger causes the coupling member 1132 to pivot to a point at which it no longer pinches tubing member 1050. Further, trigger 1128 may also compresses air bladder 1097 to initiate testing as described above in connection with initiator element.

The plug element 1108 is configured so that, when inserted into the urethral meatus of a patient (see FIG. 13), it will substantially block or prevent fluid flow out of the urethra, as well as into the urethra other than through the meatus plug device channel 1112. Further, when inserted, the plug element is positioned distal of the urethral sphincter 1306 (toward the outside of the body) as shown in FIG. 13. In the embodiment shown in FIG. 12, the distal end or distal portion 1114 of the plug element is substantially conical in shape, and decreases in diameter toward its distal end 1114. A proximal portion 1199 is configured to engage the inner wall of the urethral canal to substantially prevent fluid flow therebetween. Other shapes, however, are also possible so long as fluid flow into or out of the urethral is substantially blocked (other than through the meatus plug device channel) and the plug element remains located distal of the urethral sphincter. The meatus plug device 1102 is made of a biocompatible material, such as stainless steel or polypropylene. The meatus plug device may be disposable, but may also be made of a sterilizable material so that it can be reused.

The first fluid conduit 1010 of the tubing assembly also includes an elongated single lumen tubing member 1032 having a first end 1006 and a second end 1034 and a fluid channel extending therethrough. A spike device 1036 is coupled to the first end 1006 of the single lumen tubing member for attachment to a fluid bag 1038 (having a fluid 1010 therein) in a manner well known in the art. As described above, the meatus plug device and first fluid conduit are coupled to one another such that fluid from the fluid source traveling through the first fluid conduit may pass through the insert member (via the channel therein) and into the urethral canal distal of the urethral sphincter. Further, as the first pressure interface 1024 is in fluid communication with the first fluid conduit and ultimately the urethral canal, pressure at the pressure interface substantially corresponds to the pressure within the urethral canal distal of the urethral sphincter.

Use of the system 100 including a SUI testing module 1000 is as follows. First, the SUI testing module is removably coupled to the control device 102 in the manner described above. The physical coupling causes the identification probes 502 of the control unit to engage the module identification element(s) 504 of the SUI testing module, enabling the control device to identify the SUI testing module. The physical coupling also brings pressure interface 1024 in physical contact with pressure transducer 128 as described above so that pressure changes at the pressure interface can be detected by the pressure transducer and transmitted to the electronics assembly for interpretation. The pressure interface 1026*a* at the proximal end of tubing member 1025 similarly comes in contact with pressure transducer 1030 so that pressure within tubing member 1025 can also be detected. Finally, the tubing loop 1012 is brought into physical contact with the pump device 118 so that the pump device can drive fluid through the first fluid conduit by peristaltic motion, as described above.

Figure 20:
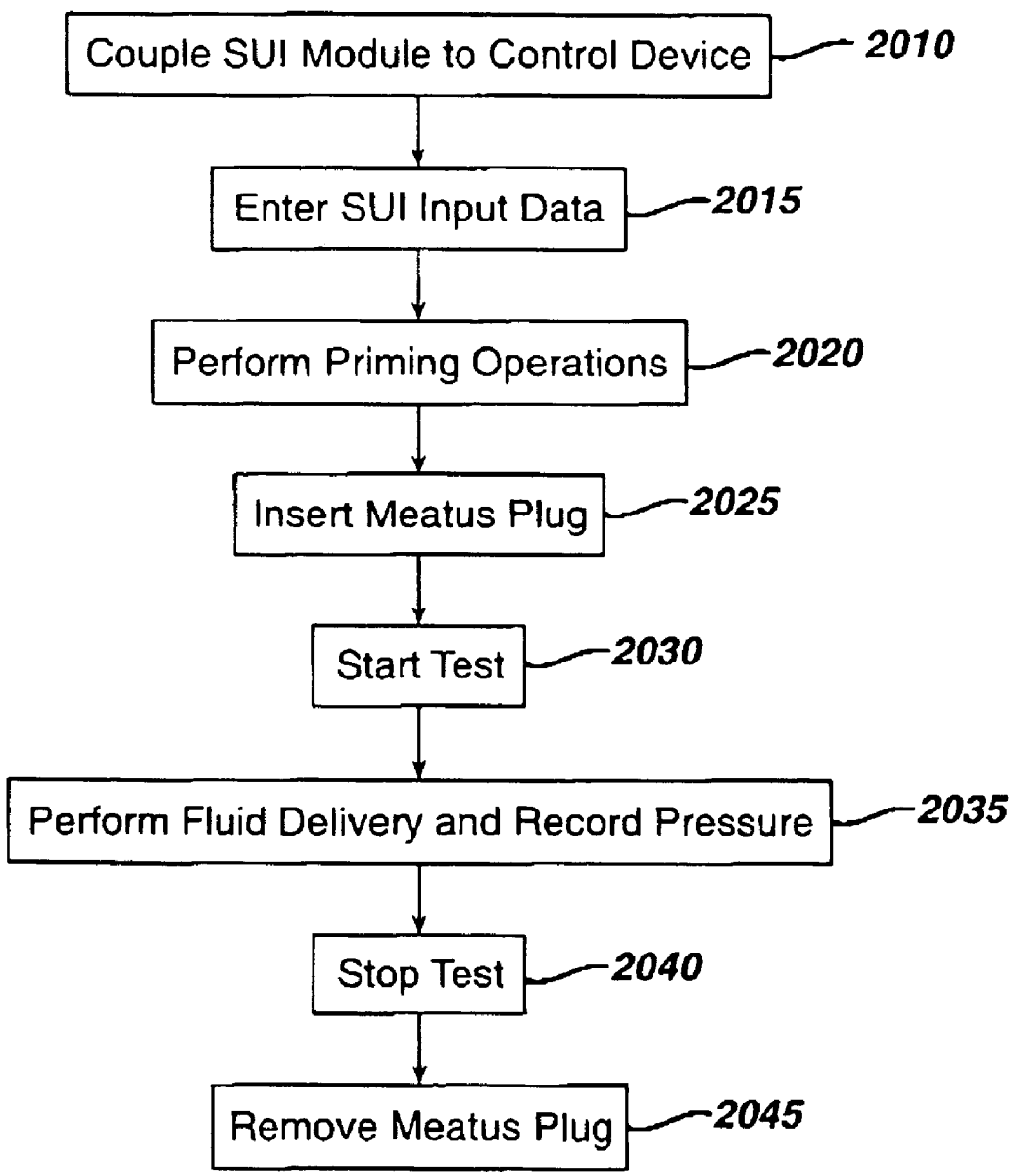
FIG. 20 is a flow diagram illustrating steps for using the system of FIG. 10.

As shown in FIG. 20, once the SUI testing module 1000 is coupled to the control device 102 (2010), the operator enters appropriate input data into the keypad 108 or other input device (2015) for the SUI test (described in more detail below). This data is received and interpreted by the microprocessor 710 and applicable information is sent by the microprocessor to the display 110. Priming operations are then performed (2020) to ensure that the first fluid conduit 1010 contains fluid. At this point, the microprocessor is ready to start the test routine.

The meatus plug 1102 is inserted into the meatus of the urethra (2025) and the test is started (2030) by pressing the activation button as described above. This in turn sends instructions to the pump device via the integrated circuit. The pump device then pumps fluid 1040 through the first fluid conduit 1010 and meatus plug device channel 1112 and into the urethral canal distal of the urethral sphincter (2035). As fluid pressure builds in the urethral canal 1302, pressure in the pressure chamber 1016 also builds. This pressure is transmitted through the filter component 1022 and pressure interface 1024 to the pressure transducer 128, which receives the pressure data and transcribes it into an electrical signal. The electrical signal from the pressure transducer is sent to the microprocessor 710 via the integrated circuit 702 where it is acquired and conditioned. The information is then sent to the display 110 via the integrated circuit. The microprocessor ends the test after a specified amount of time, or upon receipt of input from the user by sending an "off" signal to the pump motor drive. Once the test has been completed, the operator disengages the activation button 1118 (step 2040) and removes the meatus plug element from the meatus 1304 (2045).

Figure 8D:
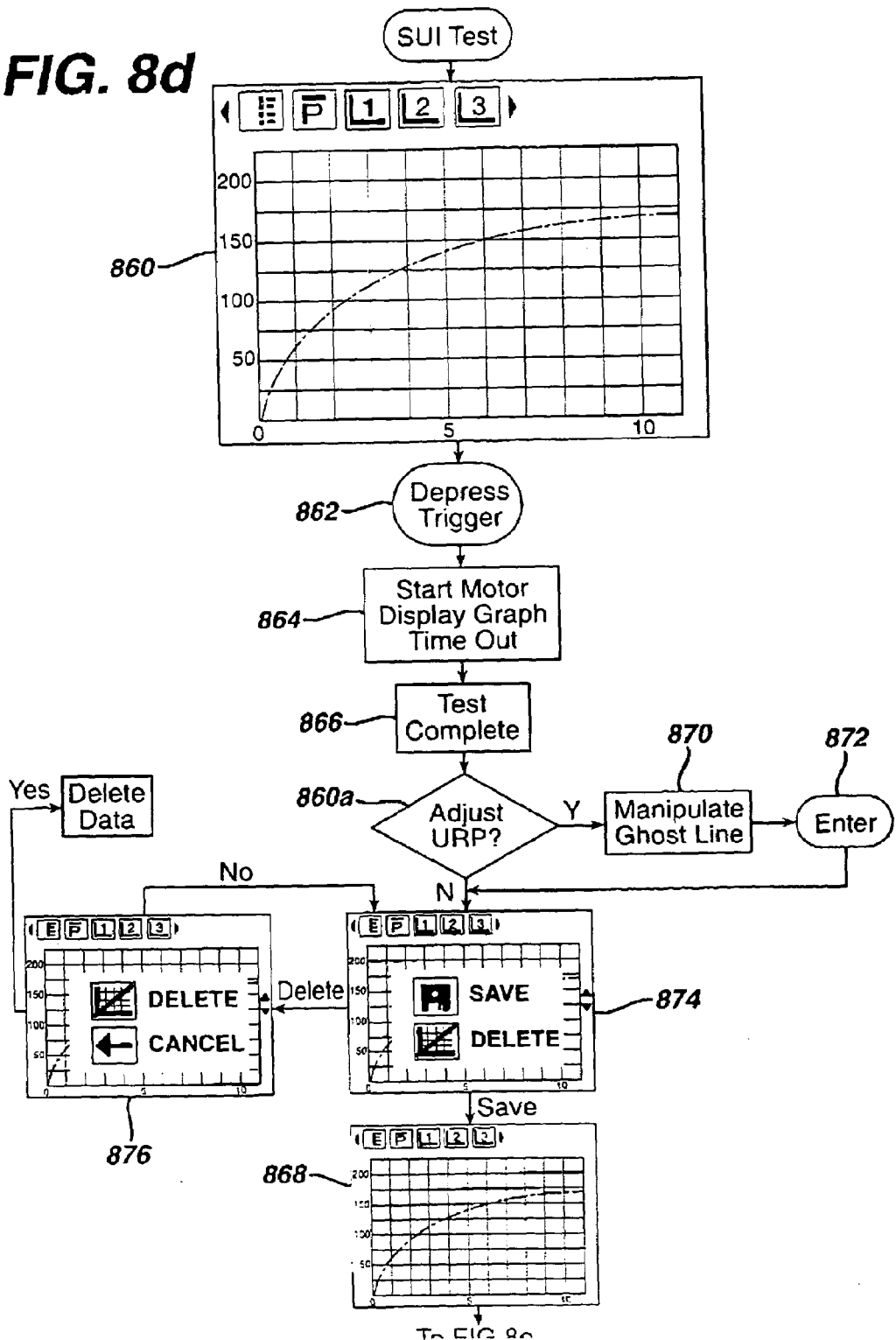
Figure 8E:
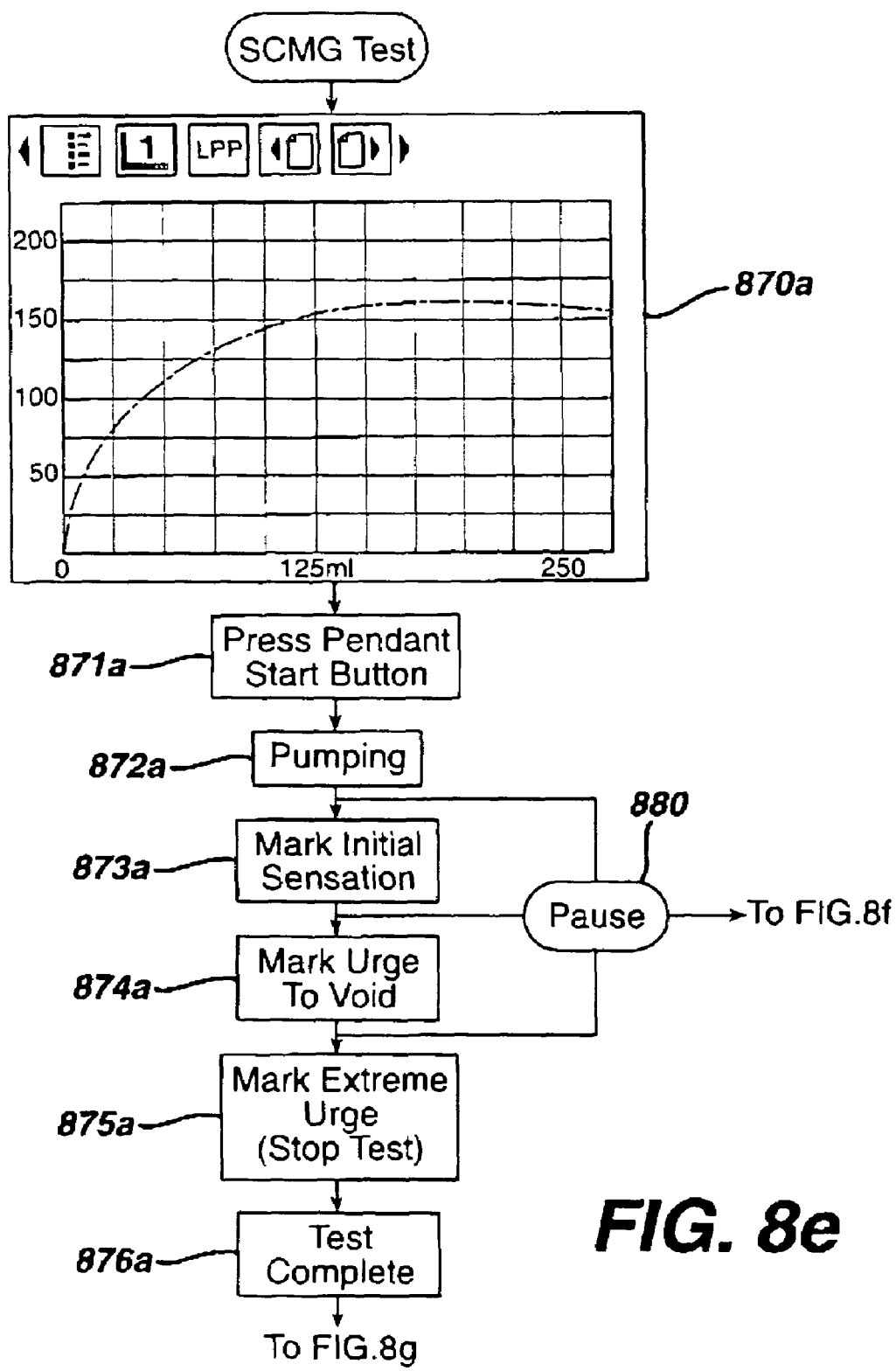
Figure 8F:
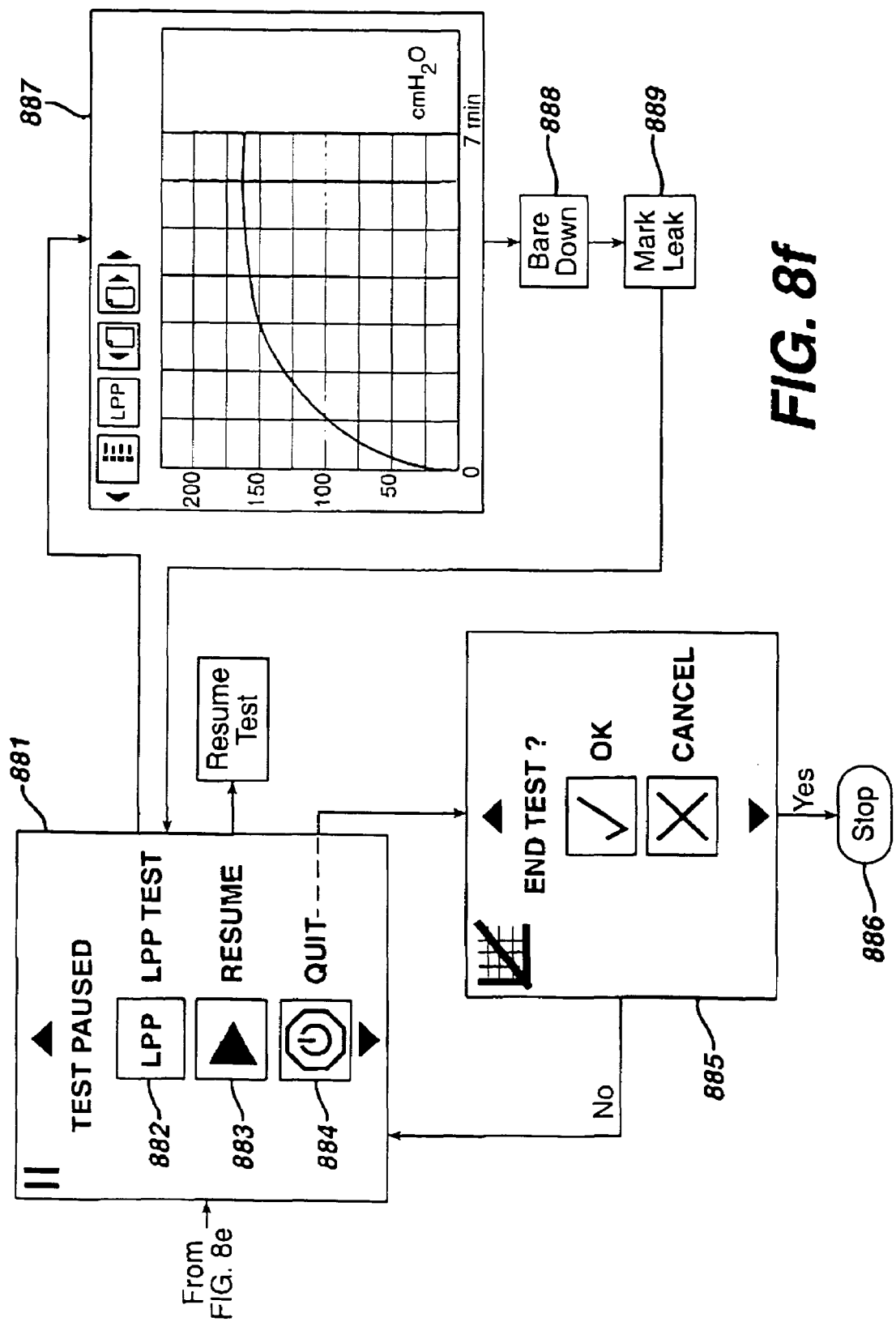
Figure 8G:
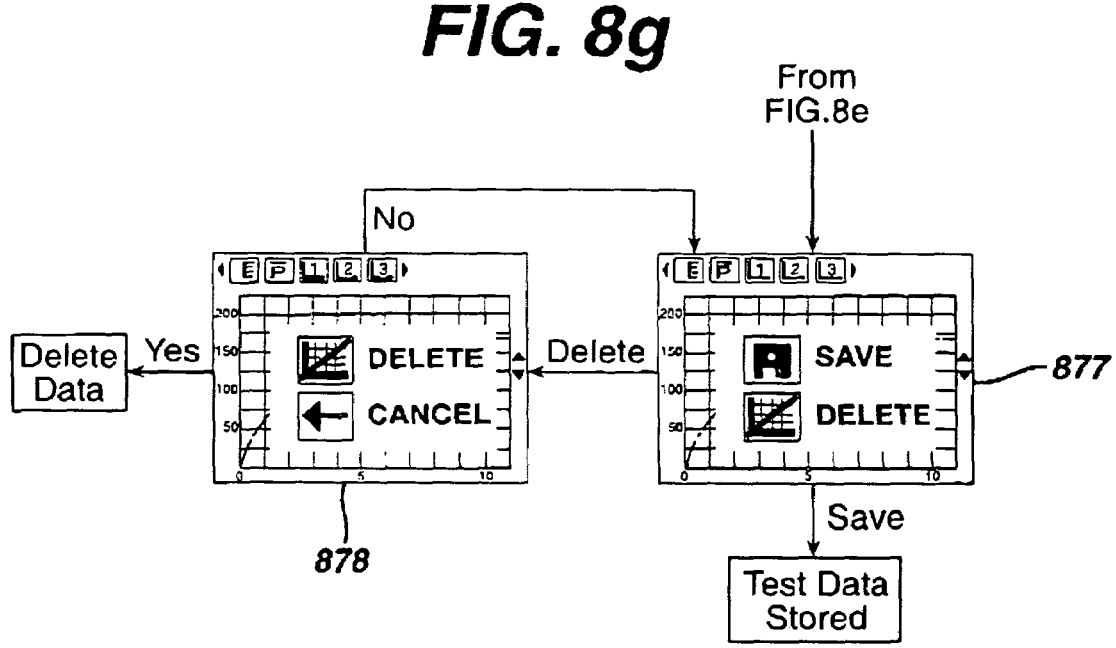
Figure 8H:
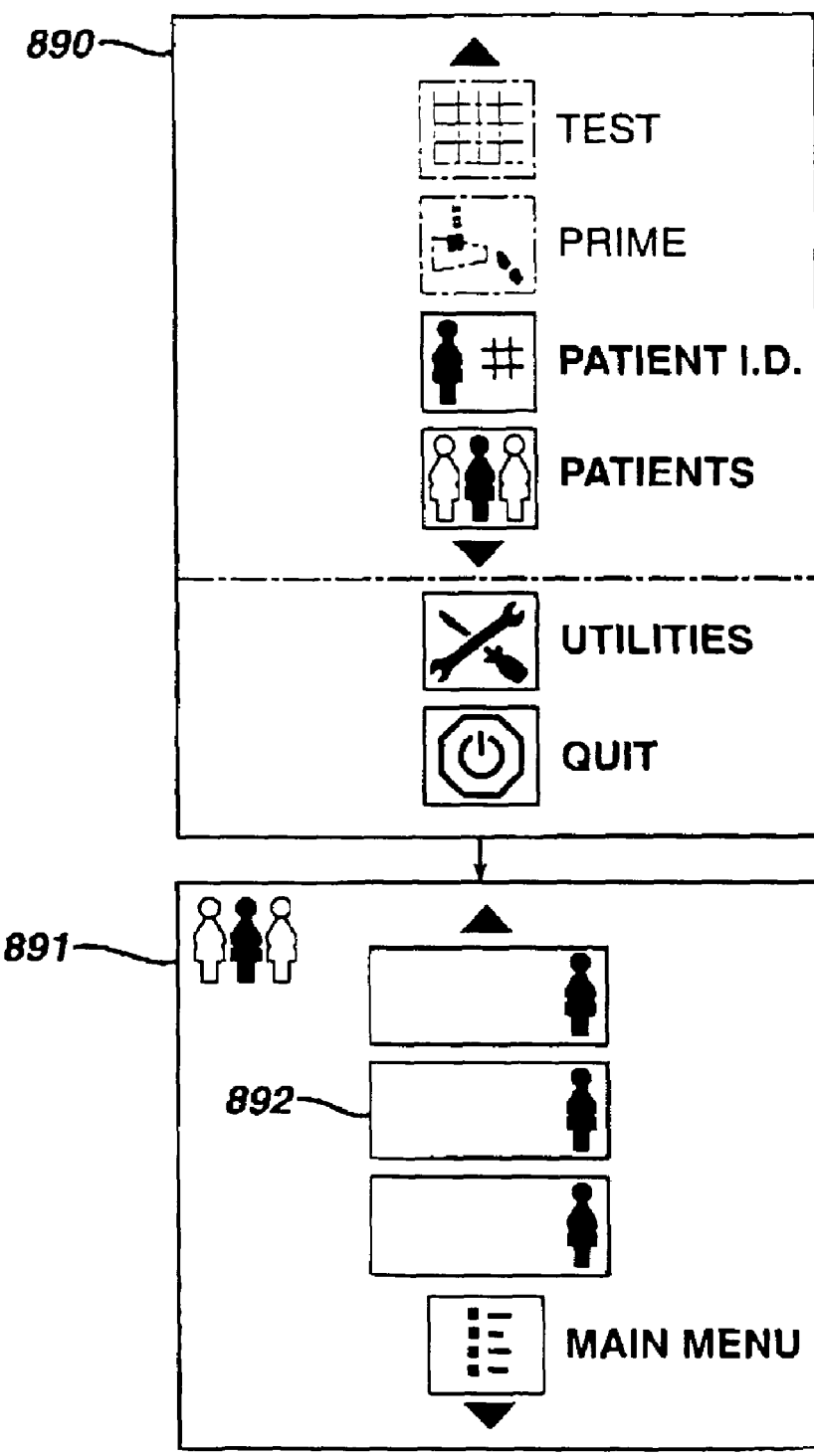

Referring once again to FIGS. 8*a–i*, and in particular FIG. 8*d*, when the "Test" option is selected the SUI test can be performed. The SUI Test screen appears 860, and the user initiates the test by depressing the trigger 1128 or movable shell 1126 (862) to allow fluid flow into the urethral canal as described above. The motor is then activated and the pump device pumps fluid into the urethral canal for a predetermined period of time, preferably 15 to 20 seconds. During this time a graph (see 860) is continuously displayed illustrating measured pressure on the vertical axis (preferably in cm of water) versus time on the horizontal axis. As fluid is pumped into the urethral canal, pressure within the urethral canal distal of the sphincter continues to increase until that point in time at which the urethral sphincter yields (open) under the force of the pressure within the urethral canal. At that point the pressure curve becomes substantially flat, as illustrated in FIG. 8*d*, since the sphincter is open and fluid is filling the bladder. The value of the flat portion of the curve is considered the "urethral resistance pressure (URP)," and can be obtained from the displayed graph. On completion of the test (after expiration of the predetermined time period the pump device stops), the graph remains, and the user is preferably provided with an option to adjust the software generated URP value (860*a*) before saving the test results. To adjust the URP value, the user uses the up and down arrows to manipulate a horizontal line which indicates the URP value that appears on the screen (870). When the ghost line is at the desired value, the user presses enter (872).

Once the final URP value is displayed, a Save/Delete screen 874 is overlayed on the screen. If the user selects the "Save" option, the test results are saved in memory. If the user selects "Delete" from the Save/Delete screen 874, the user is then presented with the Save Test screen 876. If "Delete" is chosen the test is deleted, but if "Cancel" is selected, the user is returned to the Save/Delete screen.

According to one embodiment, test results for up to three out of six possible tests may be stored. Once three tests have been stored or six tests have been run, whichever comes first, the control unit 102 will disable the module identification component 504 via the identification probes 502. After testing is complete, the user may return to the main menu by selecting the "Menu" option from the Test Complete screen.

Figure 8I:
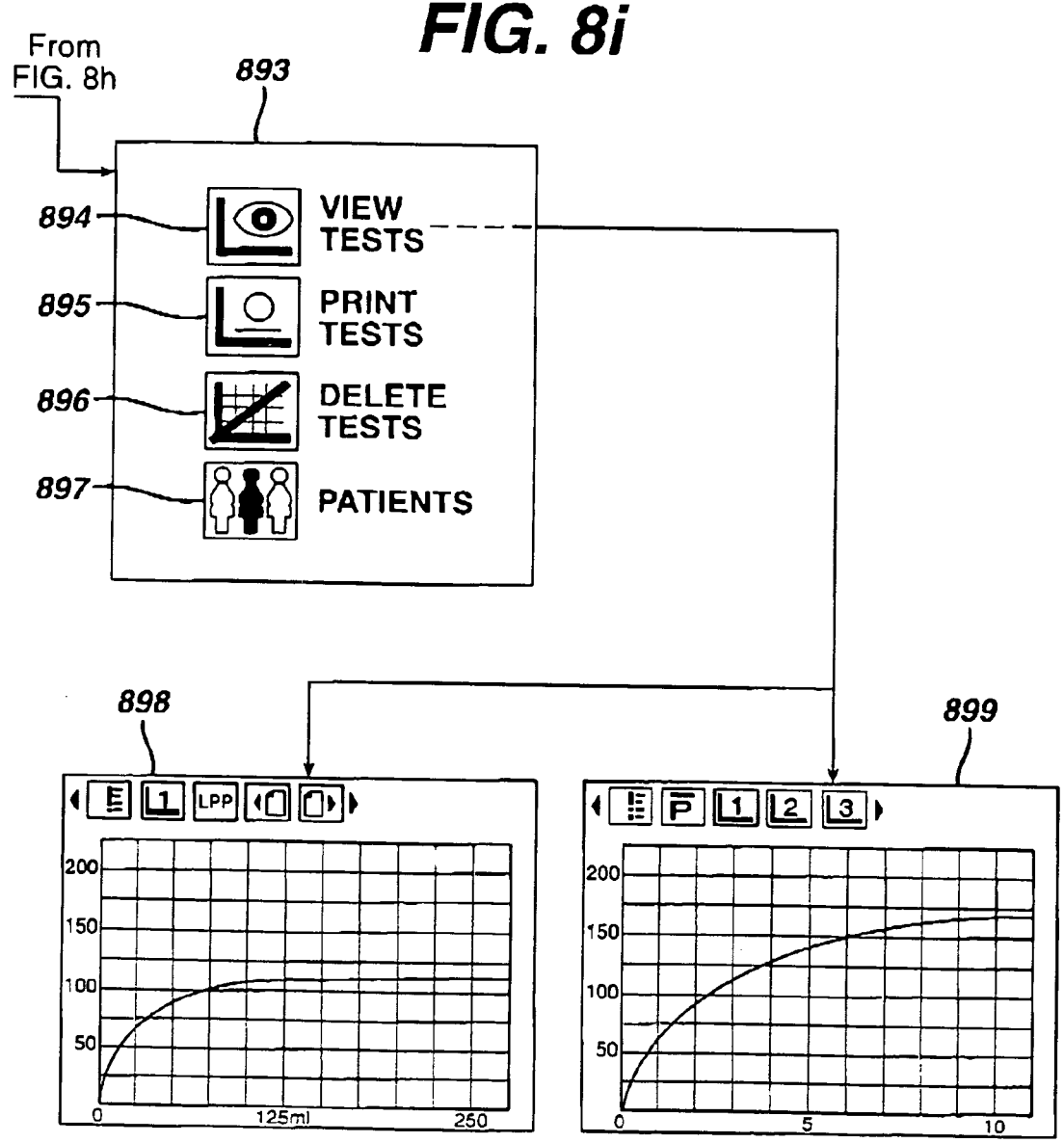

One option available from the Main Menu, as stated above, it "Patients," which allows the user to access patient and test data previously stored. According to one embodiment illustrated in FIG. 8h, when "Patients" is selected from the Main Menu, a Patients Screen 891 appears. On this screen, options for each patient and test for which data has been stored 892 are presented and selection of one of these options causes a Patient Test Menu 893 to be displayed (FIG. 8i). Selecting "Delete" 896 will present the user with the option to delete the stored data for that patient/test, and selecting "Print" 895 will enable the user to print the stored data. The Print option will only be available (will not be greyed out) when the control device is coupled to a cradle, or otherwise appropriately coupled to a printer. Selecting "View Test" will cause a Patients Test screen 898 or 899 to appear depending on whether stored data is a CMG (898) or a SUI (899) data set. The Patients Test screen may vary depending on the test module that is attached. For example, for the SUI stored data, the Patients Test screen is the screen illustrated by 899, whereas for the CMG data (discussed below), the Patients Test screen is the screen illustrated by 898. The Patients Test screens provide the user with the option to view data relevant to the particular form of test performed.

As indicated above, the results obtained from the SUI test is the urethral resistance pressure (URP), which is the back-pressure necessary to force open the urethral sphincter muscle 1306 from the reverse or opposite direction from which fluid normally flows. A major advantage of the SUI testing module 1000 is that the insert or plug element 1108 of the meatus plug device 1102 only enters the external urethral canal (meatus) and does not cause any discomfort associated with passing a catheter through the internal urethral sphincter. Thus, the diagnostic system disclosed herein having a SUI module 1000 is less invasive and more comfortable for patients. Further, the testing procedure for the SUI module 1000 is easy to implement, quick to perform, and does not require advance training by the clinician and/or physician.

SIMPLE CYSTOMETROGRAM (CMG)

The diagnostic system disclosed herein can also be used to perform both simple and complex cystometrograms. FIGS. 14–19 show both simple (SCMG) and complex cystometry (CCMG) systems for the testing of bladder function in which pressure and volume of fluid in the bladder cavity 1308 is measured during filling, storage and voiding. Urologists typically measure the static pressure relationship in the bladder of patients, this being termed as a cystometrogram (CMG), in order to determine the capacitance of the bladder as a function of pressure and volume.

Figure 14:
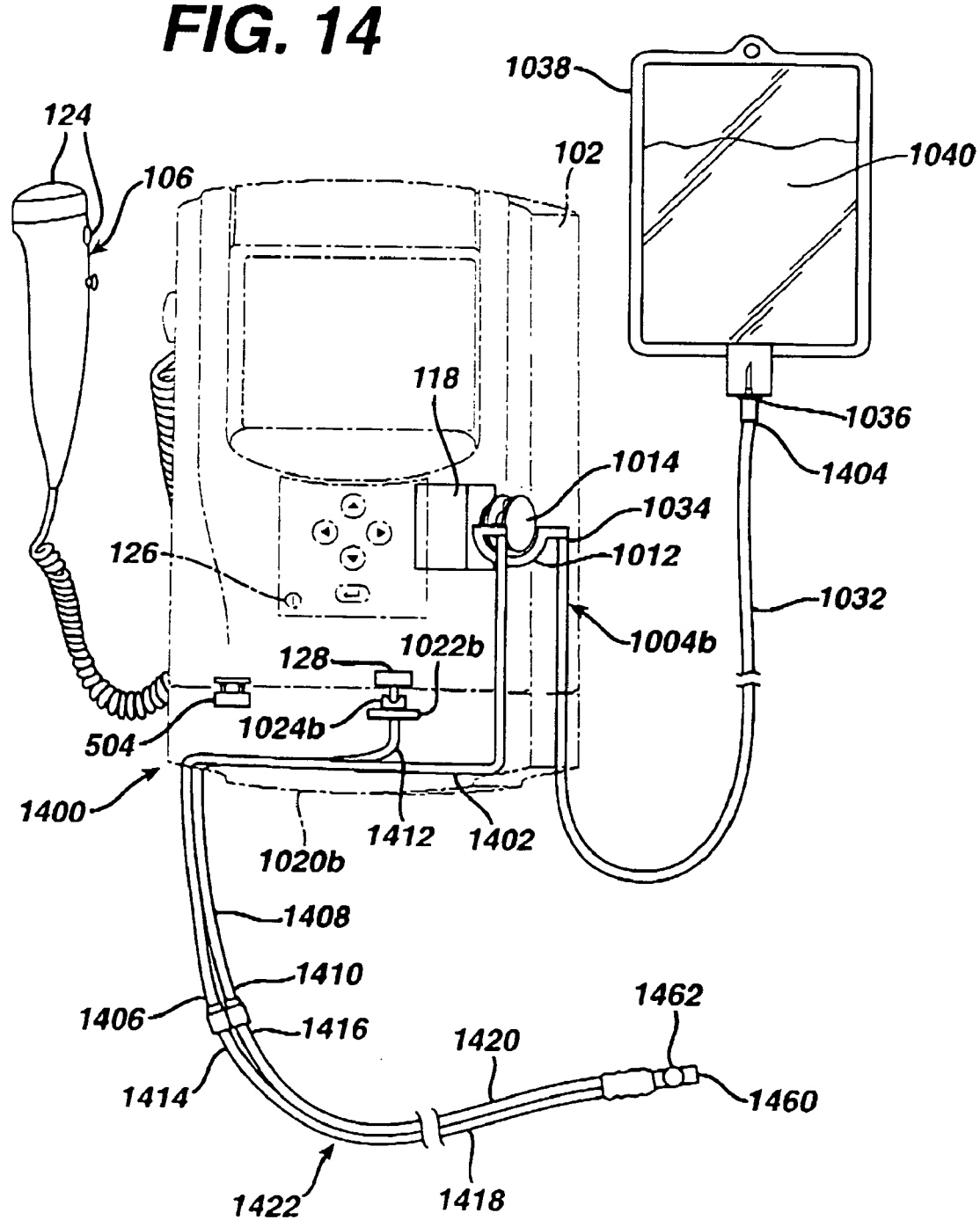
FIG. 14 is a schematic view illustrating internal components of one embodiment of a system including a SCMG module.

Referring now to FIG. 14, the SCMG testing module 1400 includes a module housing 1020b that can be removably coupled to the control device 102 in the manner described above. The module housing 1020b may be in the form of a plastic disposable cartridge. The SCMG testing module contains many elements that are similar to those described above in connection with the SUI testing module, and thus like numerals will be used for these elements. Contained within the module housing is tubing assembly 1004b including a first fluid conduit 1402 between fluid inlet 1404 and fluid outlet 1406. The tubing assembly also includes a second conduit 1408 between a distal end 1410 and a proximal end 1412. Coupled to the proximal end is a filter 1022b and pressure interface 1412 that contacts pressure transducer 128 to convey pressure information thereto when the SCMG testing module is coupled to the control device. Compliant tubing loop 1012 similarly forms part of the first fluid conduit, and couples with the pump device 118 in the same manner as described above in connection with the SUI module. The distal ends 1406, 1410 of the first and second conduits are each coupled to respective proximal ends 1414, 1416 of first and second tubing elements 1418, 1420 of a dual lumen catheter 1422 so that the first and second conduits 1402, 1408 between the proximal 1414, 1416, and distal 1460, 1462 end of the dual lumen catheter are in fluid communication with channels in the first and second tubing elements 1418, 1420 of the dual lumen catheter 1422. This attachment may be accomplished by an adhesive bond, a solvent bond, an ultrasonic weld, or any other suitable type of attachment that creates a fluid tight seal. In another embodiment, the dual lumen catheter is an inflatable balloon catheter such as a Foley-type catheter, that includes a pressure sensor 1424 positioned at the tip of the catheter (see FIG. 16). Any other suitable catheter may also be used, such as fiber optic or air charged catheters. The pressure sensor may be a micro tip transducer, an air charged sensor, a fluid charged sensor, a fiber optic sensor or any other pressure measuring sensor.

Figure 15:
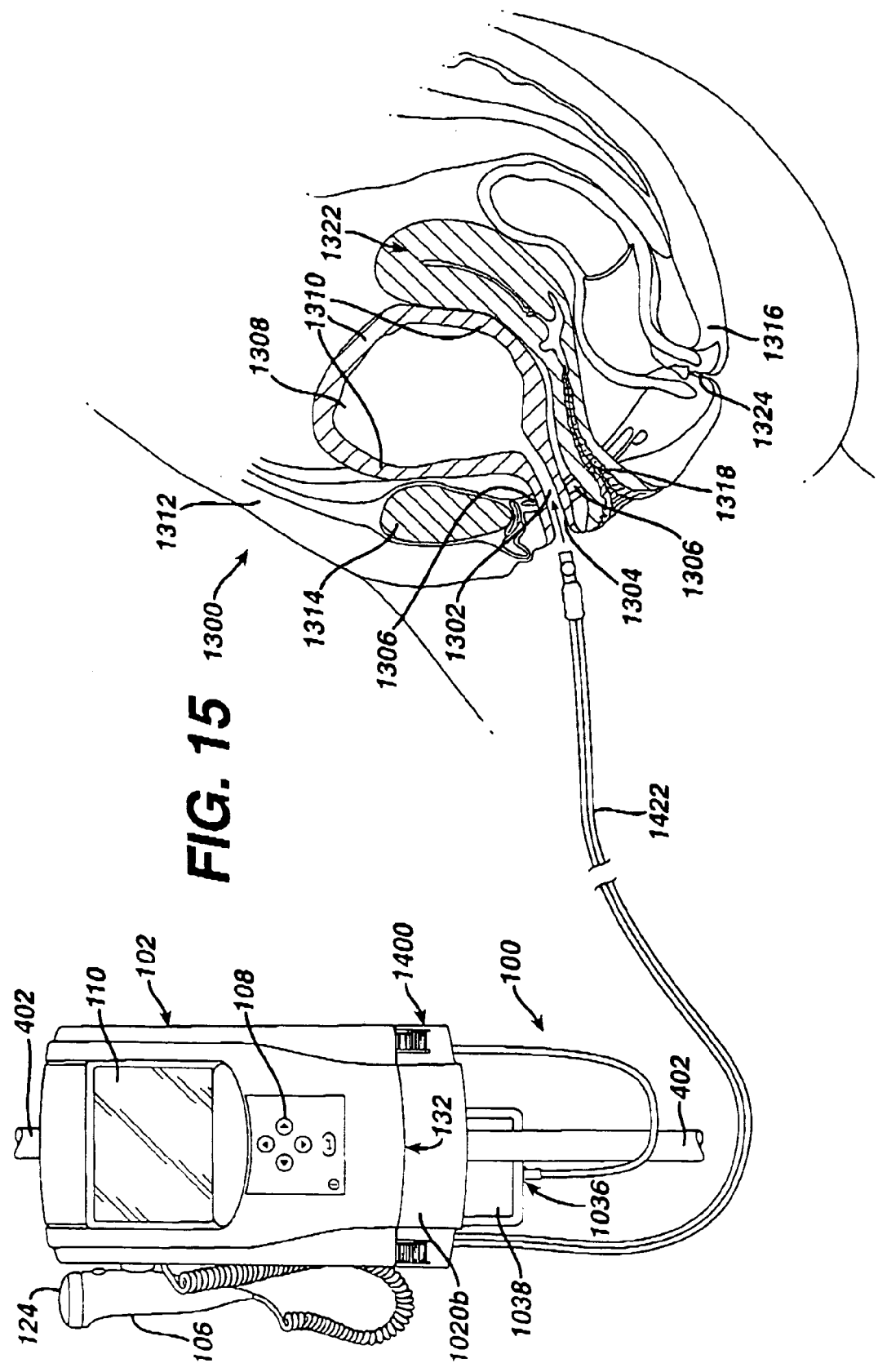
FIGS. 15–16 are schematic views of the system of FIG. 14 in relation to a female urinary/reproductive system.
Figure 16:
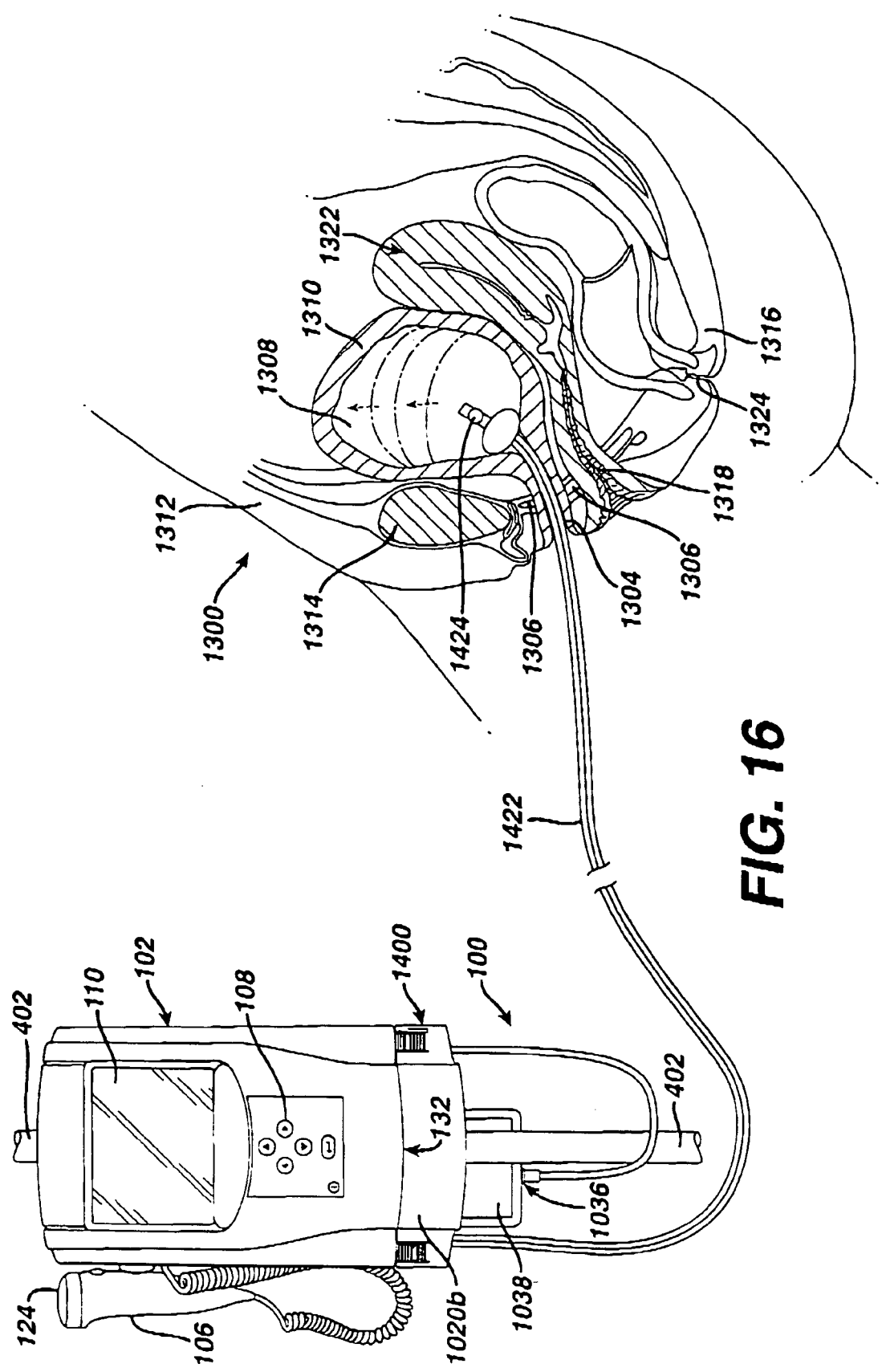
Figure 21:
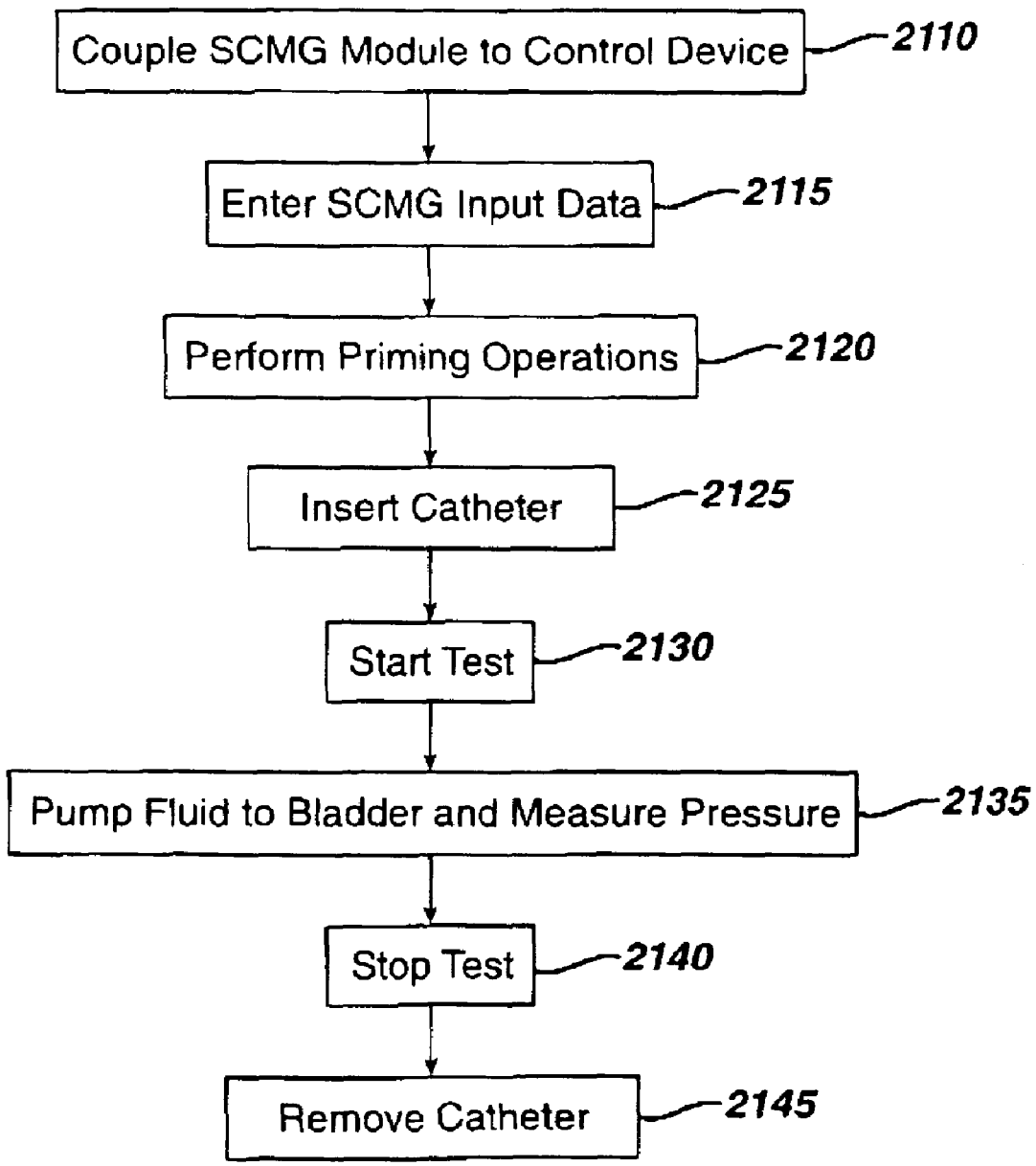
FIG. 21 is a flow diagram illustrating steps for using the system of FIG. 14.

Use of the diagnostic system to perform a SCMG will now be described in detail with reference to FIGS. 15, 16 and 21. First, the SCMG testing module is coupled to the control device in the manner described above (2110). The physical connection causes the identification probes 502 of the control unit to engage the module identification element(s) 504 of the SCMG testing module, enabling the control device to identify the SCMG testing module in the manner described above. The physical coupling also brings the pressure interface 1024b in contact with the pressure transducer 128 so that pressure changes in the second fluid conduit can be detected by the pressure transducer. This coupling also causes the tubing loop 1012 to engage the pump device so that the pump can drive fluid through the tubing loop by peristaltic motion, as is also described above.

Once the SCMG testing module 1400 is coupled to the control device 102, the operator enters input data appropriate for the SCMG test (2115). This data is received and interpreted by the microprocessor 710 and applicable information is sent by the microprocessor to the display 110. Priming operations are then performed (2120). At this point, the microprocessor is ready to start the test routine.

The dual lumen catheter 1422 is then inserted into the bladder 1308 (2125) via the urethra 1304 and the test is started by pressing the input pendant switches 124 (2130). The microprocessor 710 receives the signal from the input pendant switches. Instructions are then sent to the pump device 118 via the integrated circuit 702. The pump device then pumps fluid through the first fluid conduit 1402 and tubing element 1418 into the bladder (2135). As fluid volume builds in the bladder, pressure in the bladder also builds. This pressure is transmitted through tubing member 1420 and the second conduit 1408, filter component 1022b, and pressure interface 1024b. The pressure transducer 128 receives the pressure data and transcribes it into an electrical signal. The electrical signal from the pressure transducer 128 is sent to the microprocessor 710 via the integrated circuit board 702 where it is acquired and conditioned. During the course of a typical SCMG test, the patient provides event input, such as feeling the need to void and/or the intensity of that feeling, which is input to the control device via input pendant switches 124, as will be described more fully below. The microprocessor ends the test (2140) after a specified amount of time, or upon receipt of an "off" signal from input pendant switch 124. Once the test has been completed, the operator and removes the catheter 1422 from the bladder (2145). Following the test the software then exits the SCMG test subroutine, and the data storage routine is run to store and/or display results of the test.

Figure 10:
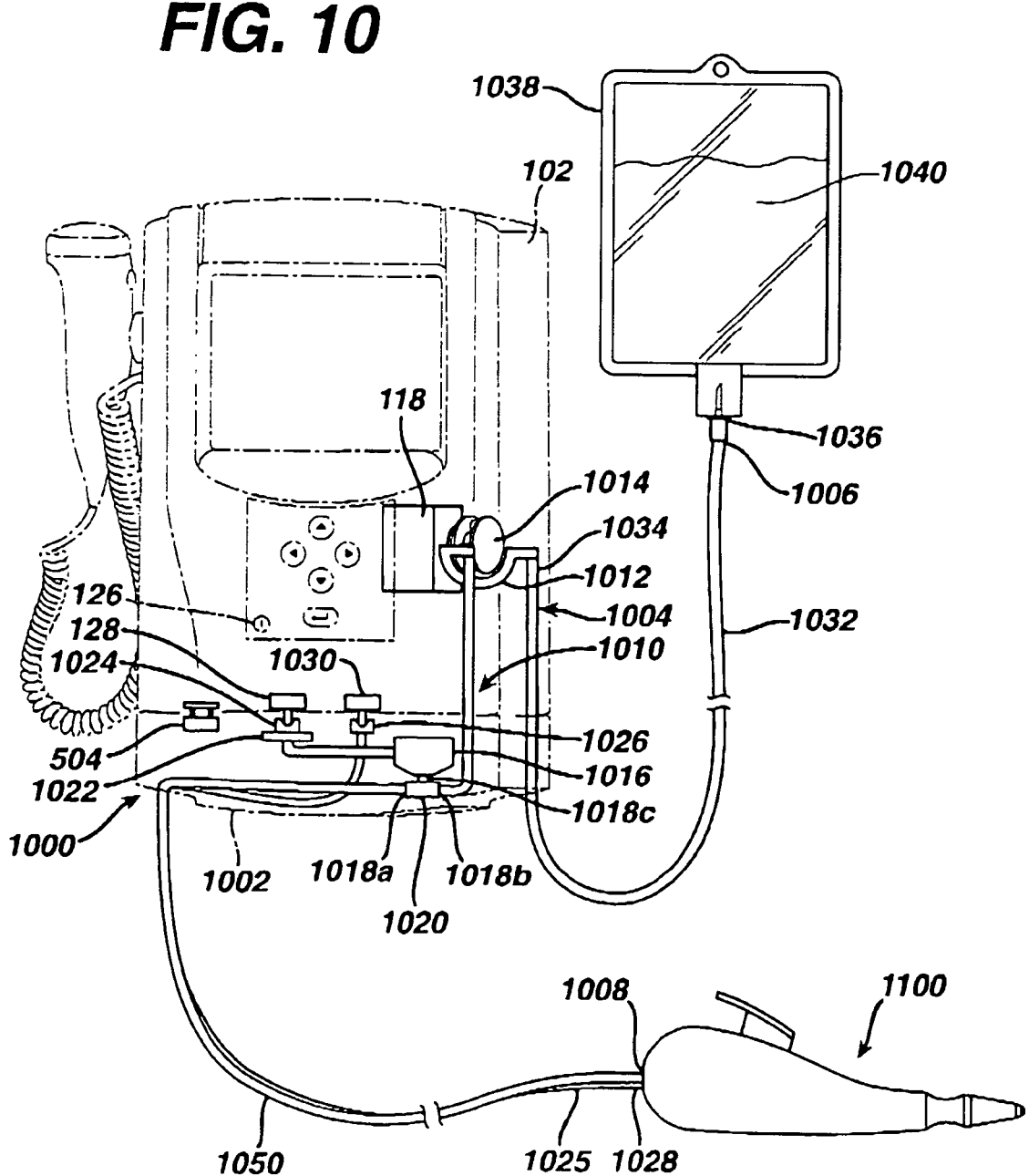
FIG. 10 is a schematic representation of a portable medical system including an SUI module.
Figure 10A:
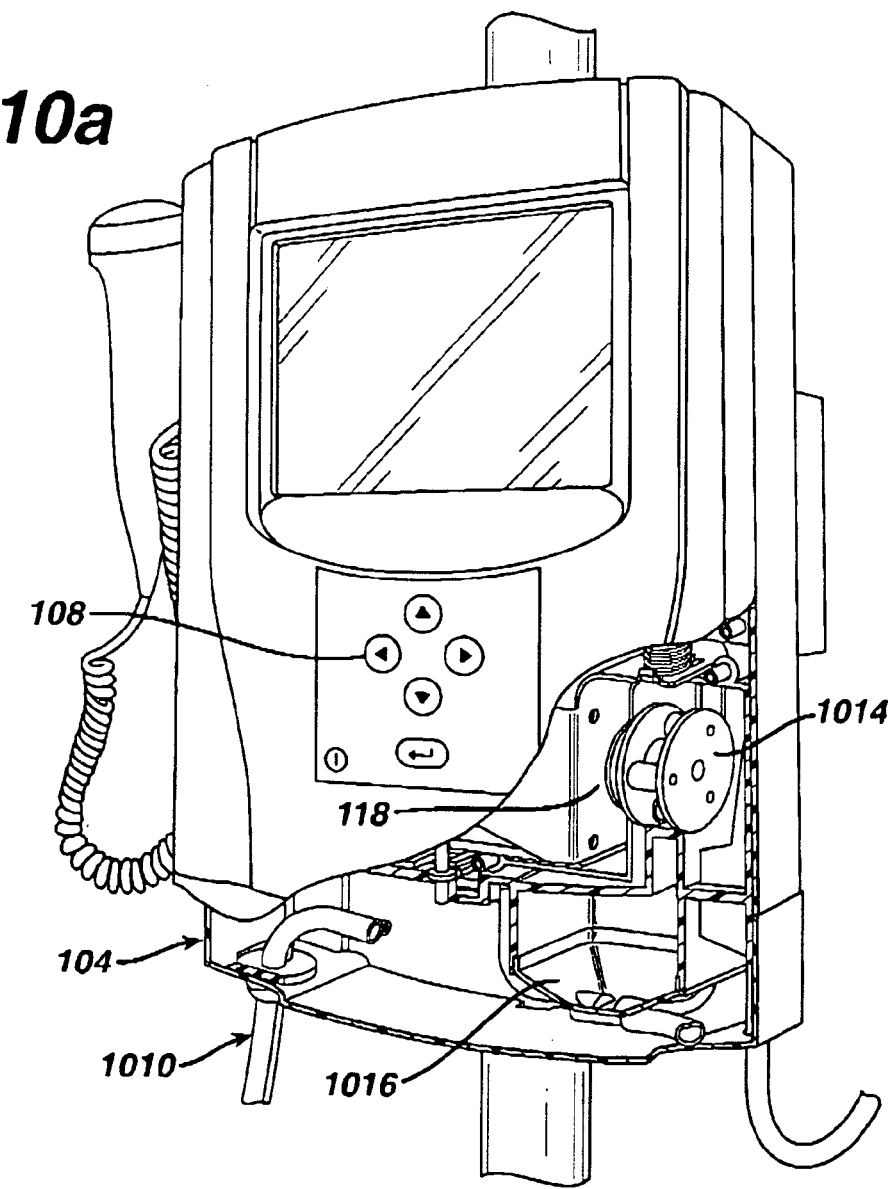
FIG. 10a is a partial cross-sectional view of one embodiment of a portable medical system including an SUI module.
Figure 10B:
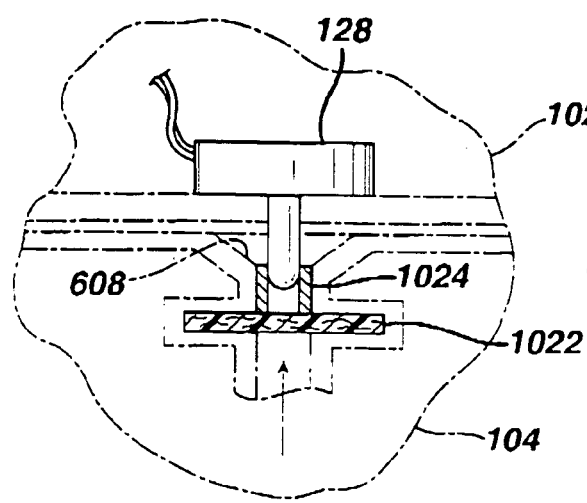
FIG. 10b is an enlarged view illustrating a pressure transducer and filter according to one embodiment of the present invention.

Referring again to FIGS. 8a–i, and in particular FIG. 8e, when the "Test" option is selected the SCMG test can be performed. The SCMG Test screen appears 870a, and the user initiates the test by depressing input pendant switch 124 (see FIG. 10a) quickly. The pump device is then activated and pumping begins 872a. In a preferred embodiment, fluid is infused into the patient's bladder at a rate of approximately 1 ml/sec. As such, this test may be approximately 16 minutes in duration, as opposed to approximately 15–20 seconds that may be required for the SUI test.

As the bladder is filling, the patient communicates the point in time at which he/she feels the initial sensation of needing to void, and the user presses the input pendant switch 124 to mark this point in time 873a. The fluid infusion continues, and the user then marks the point in time at which the patient feels the urge to void 874a, and the point at which the patient feels an extreme, almost unbearable urge to void 875a, or has voided. Upon this third marking, the fluid infusion ceases and the test is completed 876a. During fluid infusion and after the test is complete, a graph is displayed illustrating pressure versus volume infused. After completion of the test a Save/Delete overlay 877 appears. Selecting "Save" and pressing enter saves the test data. Selecting "Delete" causes a Save/Delete screen 878 overlay to appear. Selecting "Delete" from this screen deletes the data, where as selecting "Cancel" from this screen returns to the Save/Delete overlay.

At any point between initiating pumping and completing the SCMG test, the user may pause the test by depressing and holding, or pressing firmly on the input pendant switch 880, which causes the pump device to stop pumping fluid into the patient's bladder, and a Pause screen 881 (FIG. 8f) to appear on the display. Selecting "Quit" causes a End Test screen 885 to appear, and if "OK" is selected the test is stopped 886. If "Cancel" is selected the Pause screen reappears. If "Resume" 883 is selected from the Pause screen 881, the SCMG test resumes where it left off (pumping begins again). If, however, "LPP" 882 is selected from the Pause screen 881, assessment of the patient's leak point pressure (LPP) begins. No pumping of fluid occurs during this test. First, a LPP screen 887 appears and a blank graph is displayed. Pressure in centimeters of water is plotted on the vertical axis versus time on the horizontal axis. The patient then proceeds to exert pressure on the bladder as if attempting to void 888. The user marks the point at which a leak occurs 889, and the test is automatically completed after three minutes or three leaks, upon which the user is returned to the Pause screen 881. LPP results may then be stored or deleted, the CMG test may be resumed, or the test can be terminated altogether.

COMPLEX CYSTOMETROGRAM

Figure 17:
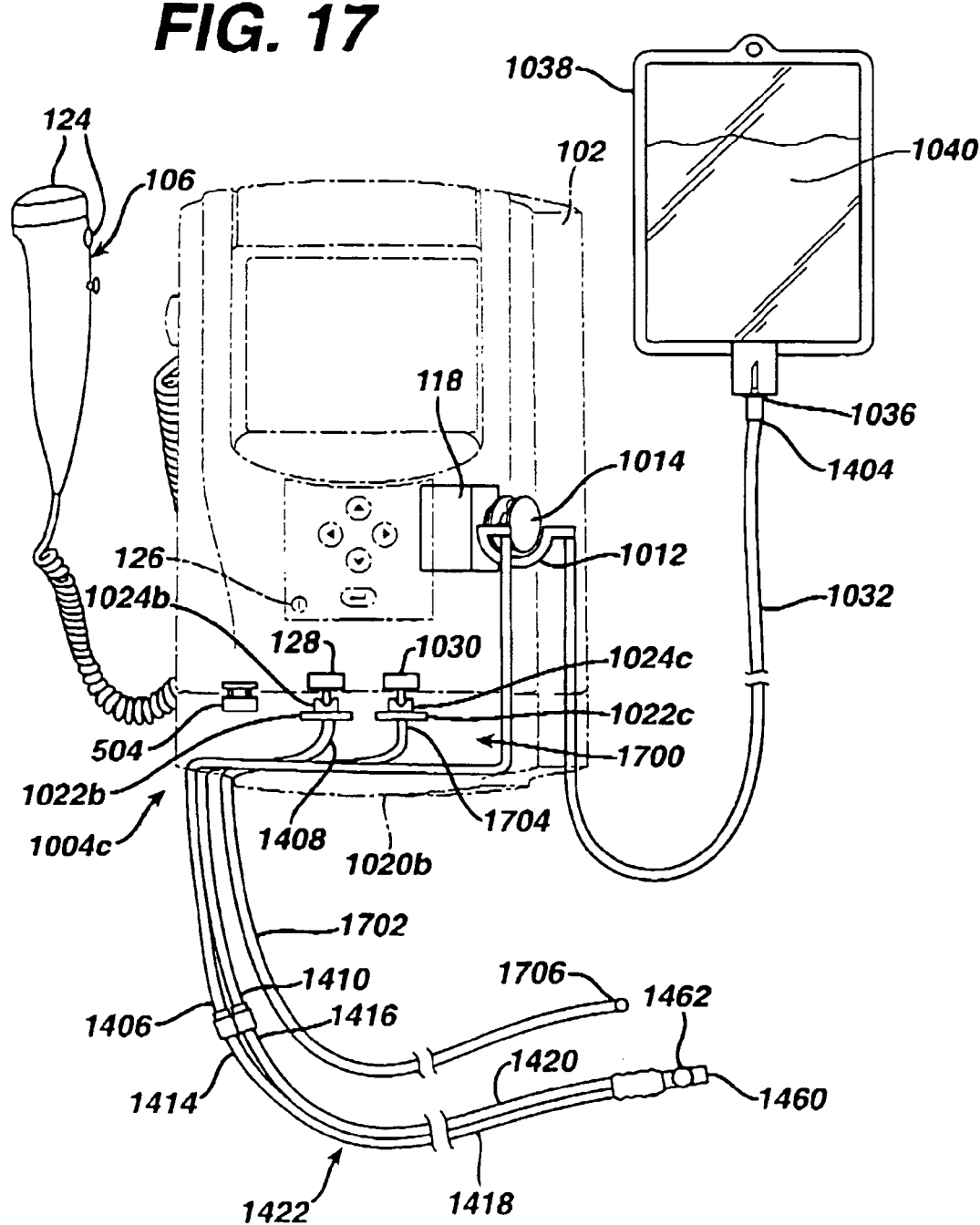
FIG. 17 is a schematic view illustrating one internal components of one embodiment of a system including a CCMG module.
Figure 18:
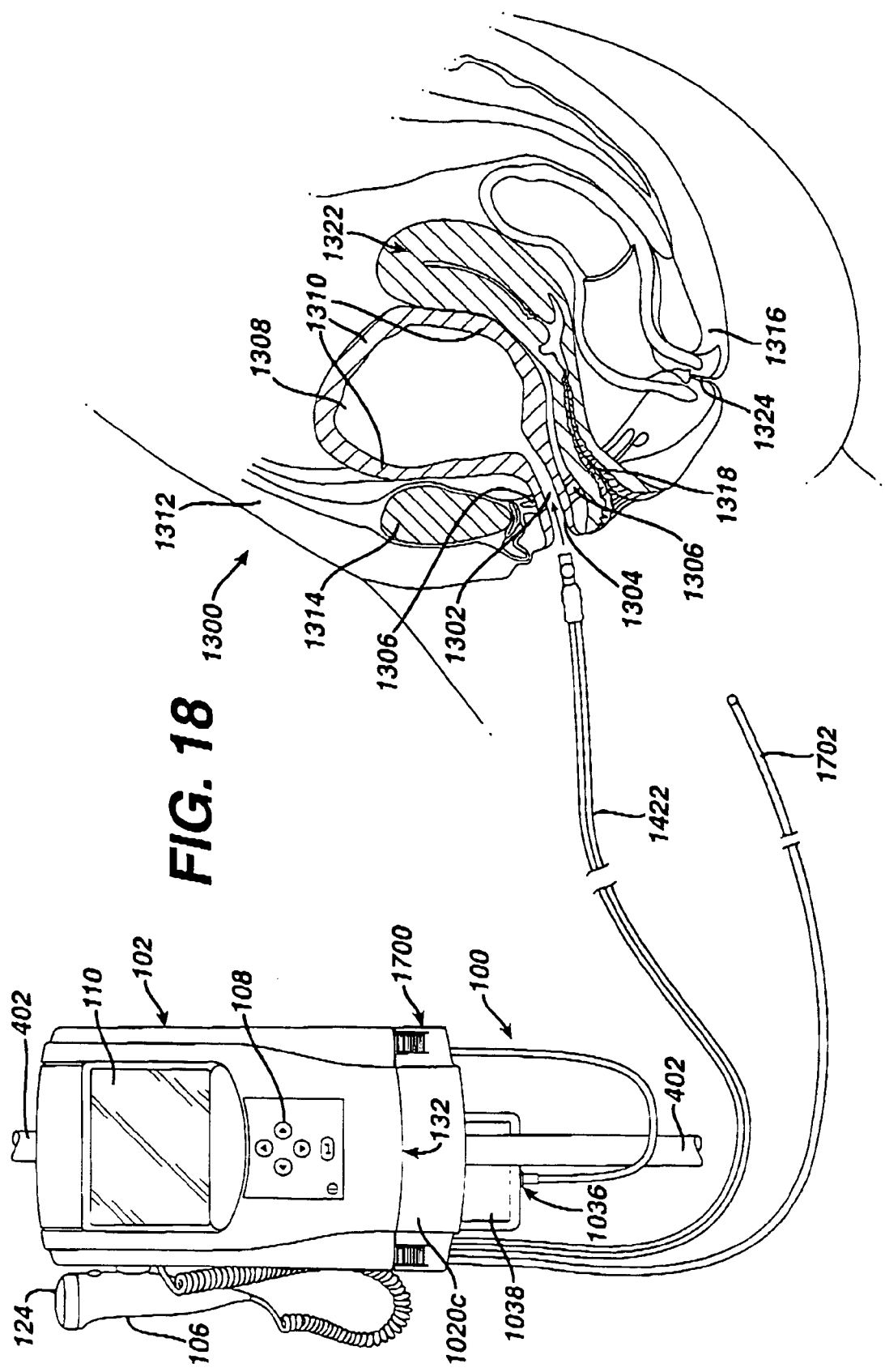
FIGS. 18–19 are schematic views of the system of FIG. 17 in relation to a female urinary/reproductive system.
Figure 19:
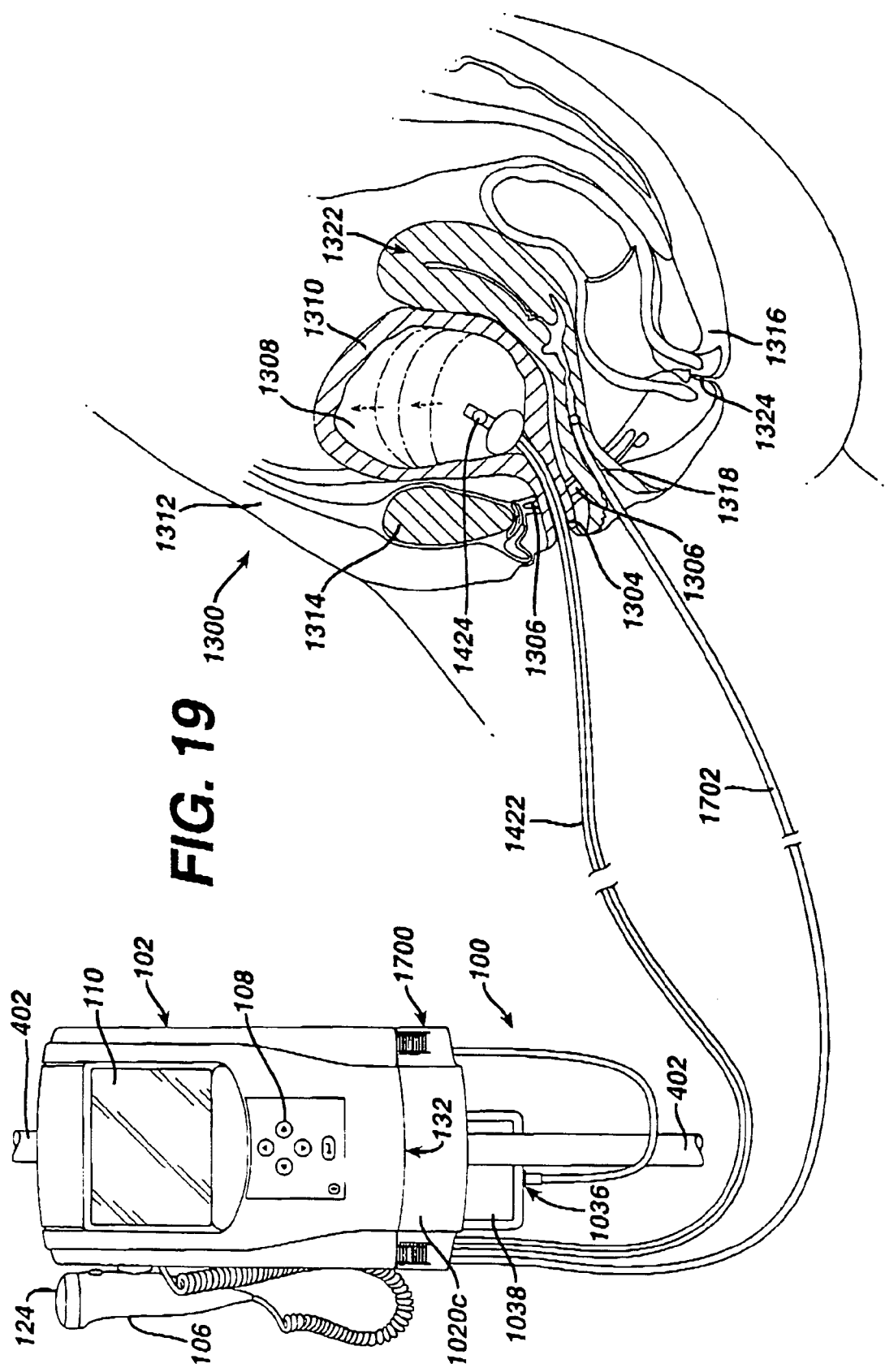

In reference to FIGS. 17–19, the complex CMG (CCMG) testing module 1700 is similar to the SCMG testing module, but the tubing assembly also includes an additional single lumen tubing member 1702 having a proximal end 1704 and a distal end 1706 and a third conduit extending therethrough. The proximal end 1704 of the single lumen tubing member is coupled to another filter component 1022c and pressure interface 1024c. Pressure interface 1024c contacts pressure transducer 1030 when the CCMG testing module is coupled to the control device, enabling pressure transducer 1030 to sense pressure within the third fluid conduit.

Figure 22:
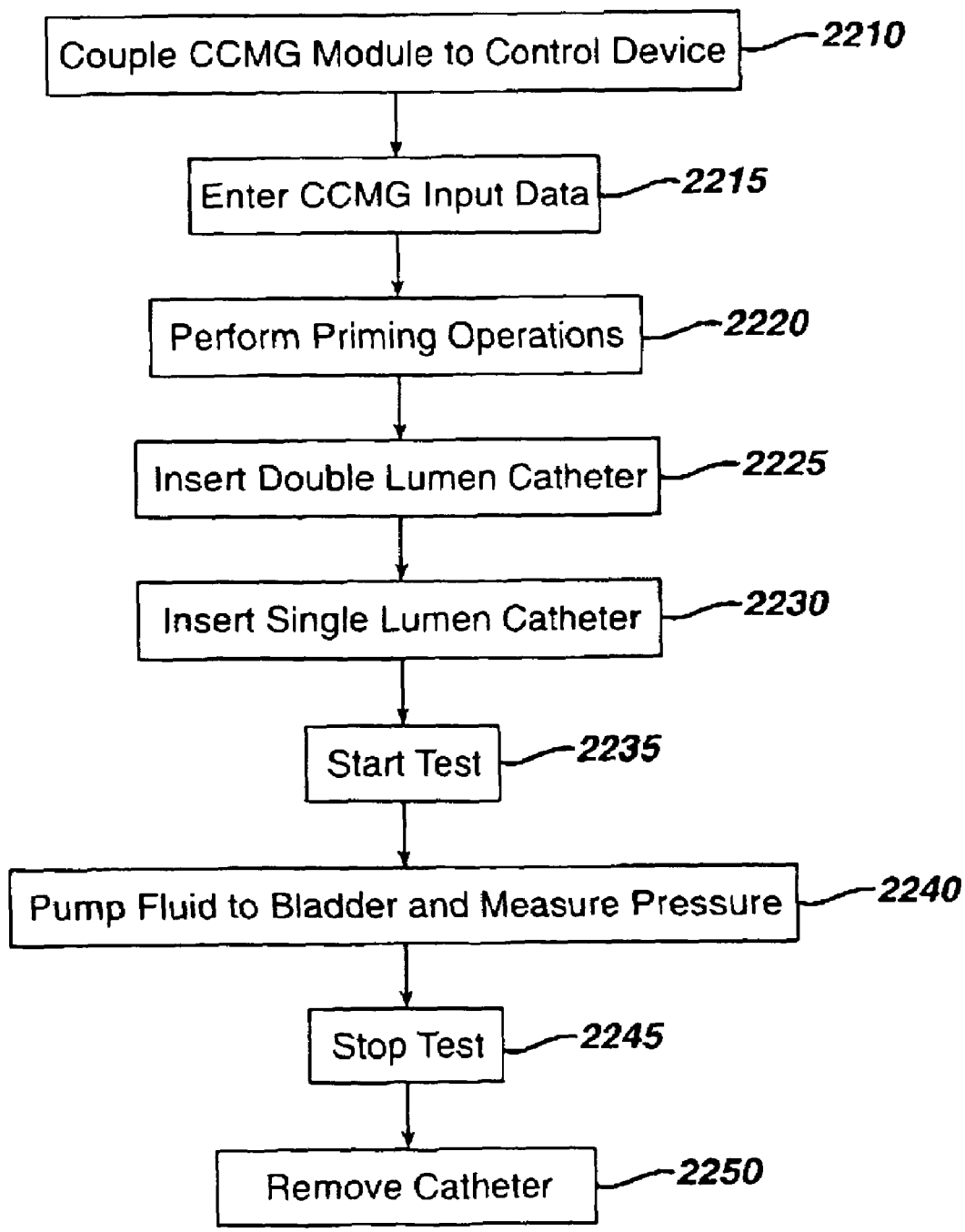
FIG. 22 is a flow diagram illustrating steps for using the system of FIG. 17.
Figure 23:
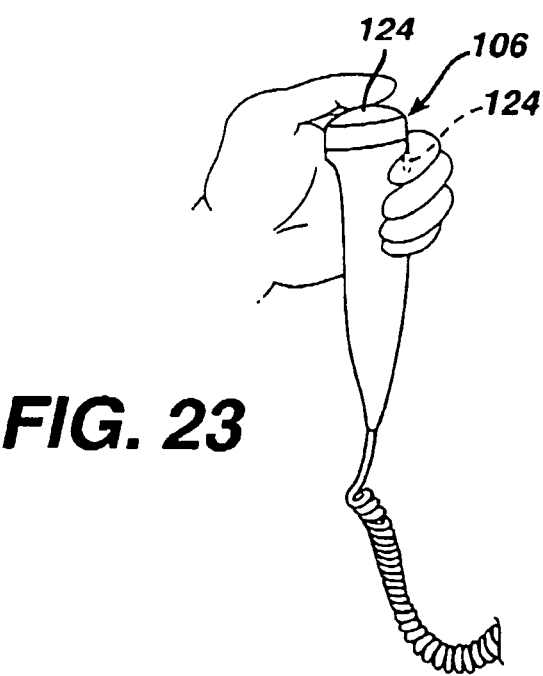
FIG. 23 is a perspective view of one embodiment of an input pendant according to the present invention.

Use of the diagnostic system to perform a CCMG will now be described in detail with reference to FIGS. 18, 19 and 22. First, the CCMG module is coupled to the control device (2210). The physical connection causes the identification probes 502 of the control device 102 to engage the identification elements 504 of the CCMG testing module, enabling the control device to identify the CCMG testing module. The physical coupling also brings pressure interfaces 1024b, 1024c in contact with the pressure transducers 128, 1030 so that pressure changes in the second and third conduits can be detected by the pressure transducers. This coupling also causes the tubing loop 1012 to engage the pump device 118 so that the pump can drive fluid through the tubing in the CCMG module.

Once the CCMG testing module 1700 is coupled to the control device 102, the operator enters input data appropriate for the CCMG test (2215). This data is received and interpreted by the microprocessor 710 and applicable information is sent by the microprocessor to the display 110. Priming operations are then performed (2220

The dual lumen catheter 1422 is inserted into the bladder via the urethra 1302 (2225). The single lumen catheter 1702 is inserted into either the vagina or the rectum (2230) and the test is started (2235) by pressing the input pendant switches 124. The microprocessor 710 receives the signal from the input pendant switches. This in turn sends instructions to the pump device 118 via the integrated circuit 702, and the pump device pumps fluid through the first tubing conduit 1042 and tubing element 1418 into the bladder (2240). As fluid volume builds in the bladder, pressure in the bladder also builds. This pressure is transmitted through pressure interface 1024b to pressure transducer 128. Similarly, abdominal pressure is transmitted through pressure interface 1024c to pressure transducer 1030. The pressure transducers receive the pressure data and transcribe it into electrical signals. The electrical signals are sent to the microprocessor 710 via the integrated circuit board 702 where it is acquired and conditioned. The microprocessor ends the test after a specified amount of time or upon receipt of an "off" signal from input pendant switches 124 (2245). Once the test has been completed, the operator disengages the input pendant switches and removes the catheters 1422 and 1702 from the bladder (2250). The stored information is then available for review on the display screen, or by a print out through a charging cradle (printer assembly), or downloaded to a PC via a software interface in the charging cradle.

Referring again to FIGS. 8a–i, the CCMG module software subroutine and graphical user interface is substantially as described in connection with the SCMG module. The system subtracts the abdominal pressure from the bladder pressure to calculate detrusor (bladder muscle) pressure. Detrusor pressure is then plotted against volume.

Both the SCMG and CCMG testing modules 1400 and 1700 provide a simple, relatively low cost procedure for recording a cystometrogram (CMG). The SCMG and CCMG testing modules are sterile, disposable assemblies that eliminate the need to disinfect equipment prior to use. This, together with a relatively simple set-up and operational procedure by the physician, greatly reduces the time required to obtain the urodynamic data. The SCMG and CCMG testing modules are more comfortable for the female patient and are more cost effective for the physician. The simplicity of the SCMG and CCMG testing modules, and the control device 102 allows operation with minimal training. Further, when combined in operational use with the SUI testing module 1000, these modules provide a near complete urodynamic diagnostic tool for the physician.

UROFLOMETRY

Figure 24:
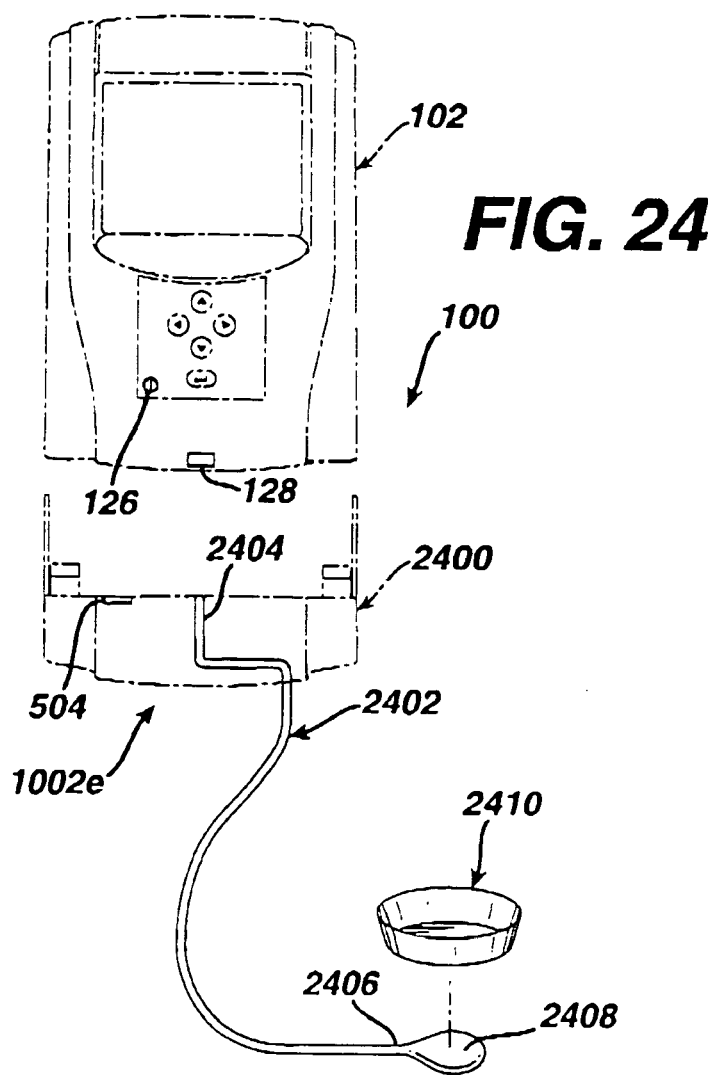
FIG. 24 is a schematic view illustrating internal components of one embodiment of a system including a Uroflowmetry module.
Figure 25:
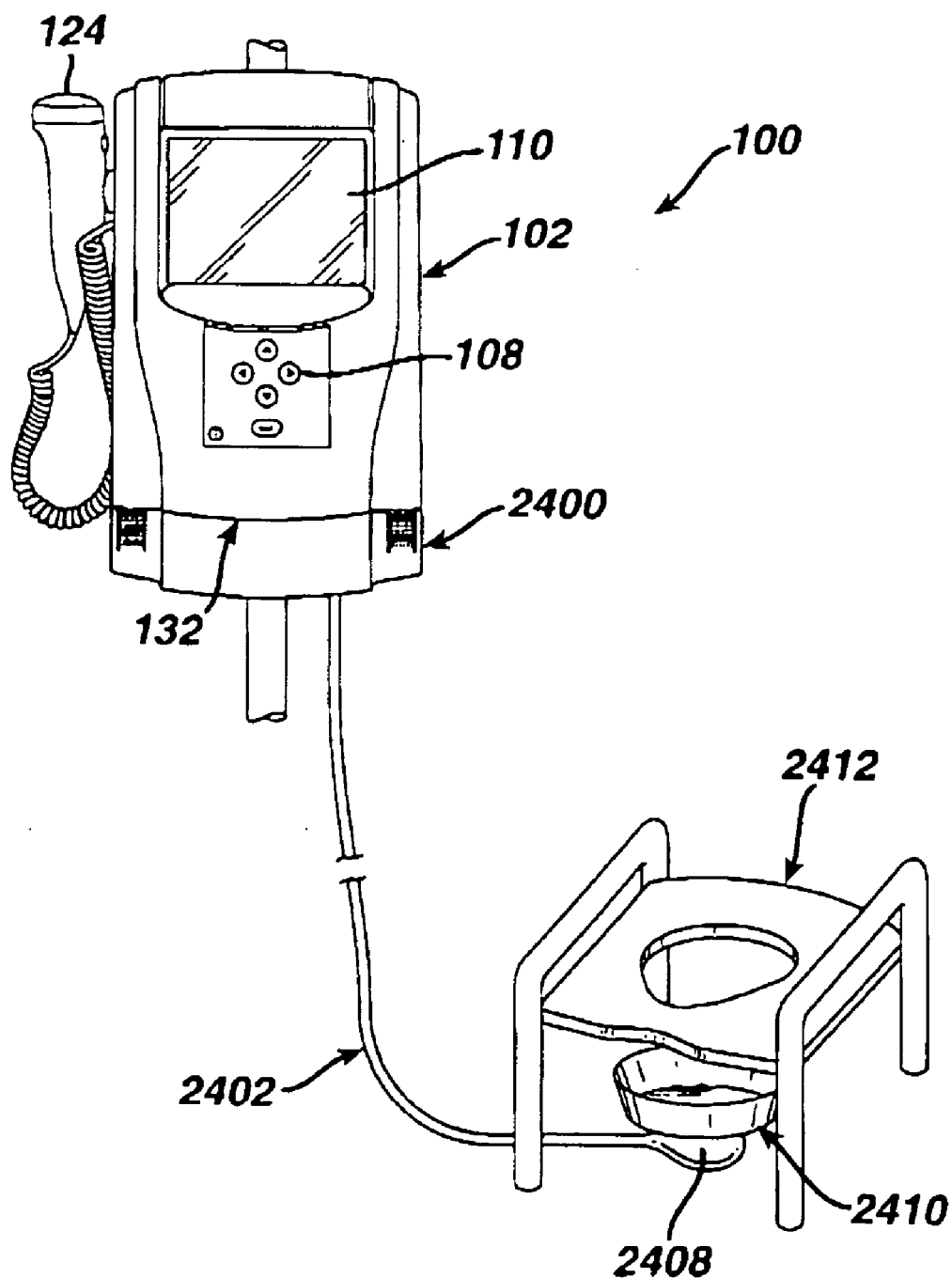
FIG. 25 is a schematic view illustrating use of the system of FIG. 24.

A uroflometry testing module 2400 can also be removably coupled to control device 102. The module housing of the uroflometry testing module 2400 may be in the form of a plastic disposable cartridge. As shown in FIGS. 24 and 25, the Uroflometry testing module 2400 includes a single lumen tubing member 2402 having a proximal end 2404 and a distal end 2406 and a channel extending substantially therethrough. A balloon 2408 or other suitable elastomeric element is coupled to the distal end 2406, however, so that the channel of the single lumen tubing member is not open at the distal end. A pressure cushion may also be used in place of the balloon. A collection bucket 2410 is positioned on top of the balloon. The inner surface of the collection bucket may also contain a urinalysis strip which, when wetted by the voided urine, allows for quantitative assessment of standard urinalysis parameters The diagnostic system including the Uroflometry testing module is operated as follows. The collection bucket is positioned under a commode 2412 to collect urine as the patient voids. Balloon is positioned relative to the bucket so that it substantially supports the bucket. As the bucket fills the pressure in the balloon rises proportionately to the weight of the fluid. When the testing module is coupled to the control device, the proximal end 2404 of the single lumen tubing member 2402 contacts the pressure transducer 128 of the control device 102 so that the pressure within the balloon can be captured and interpreted by the control device. The pressure data is used to calculate the weight and volume of the fluid (known fluid density). The stored information is then available for review on the display screen, or by a printout through a charging cradle (printer assembly), or downloaded to a PC via a software interface in the charging cradle. Once the test has been completed, the operator disengages the input pendant switches 124, and the urine and collection bucket are discarded.

Operation of the Uroflometry module software subroutine is illustrated in FIGS. 8a–b. Following module detection 802 and a command to execute the UroFlow Module Subroutine 804, the UroFlow module subroutine begins. The operator is prompted to Enter UroFlow Patient Data 840 necessary for the UroFlow test routine. Once the patient data is collected a UroFlow Scale Zeroing Procedure 841 runs. The operator then enters information necessary to initiate the UroFlow test (UroFlow Test I/O) and the test is started 842. Following the test the software then exits the UroFlow test subroutine and stores the data collected in the Data Storage routine.

VAGINAL SPECULUM

Figure 26:
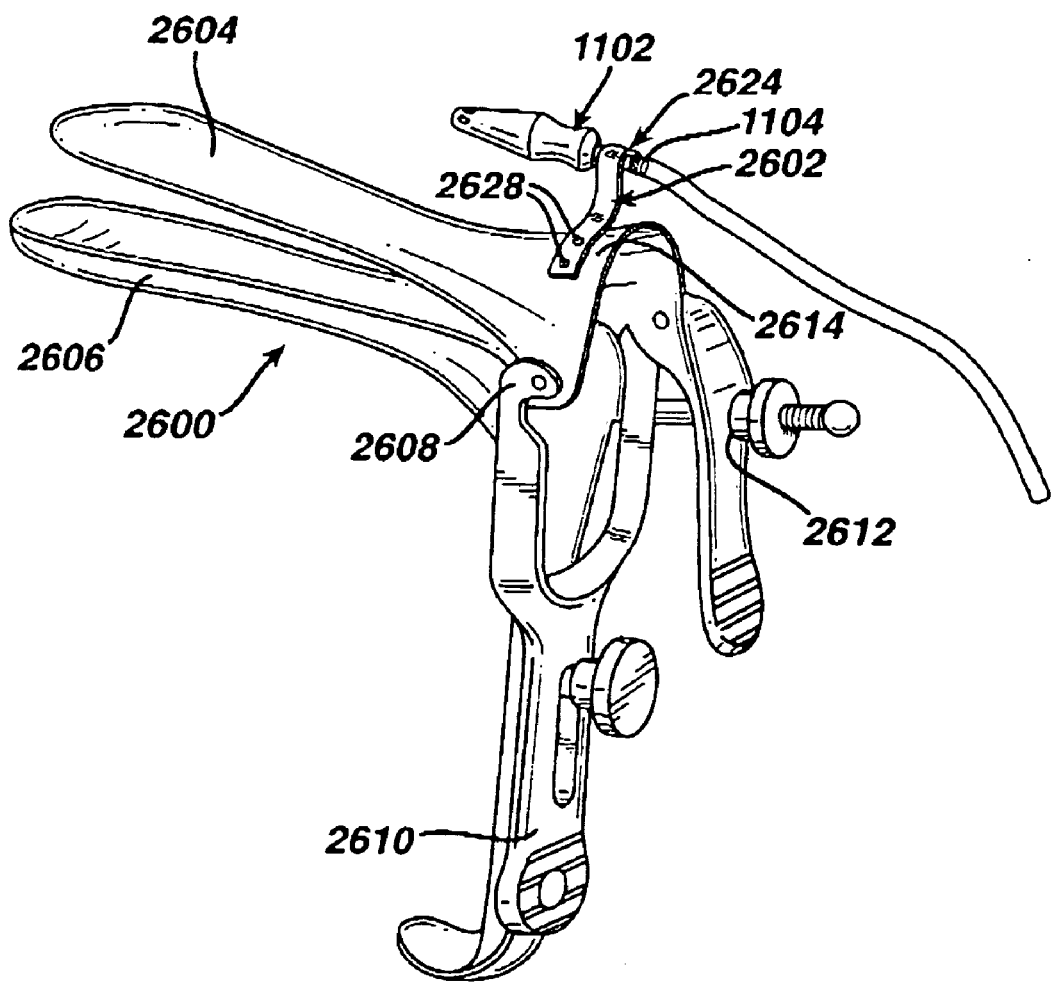
FIG. 26 is a perspective view of one embodiment of a vaginal speculum assembly in accordance the present invention.
Figure 27:
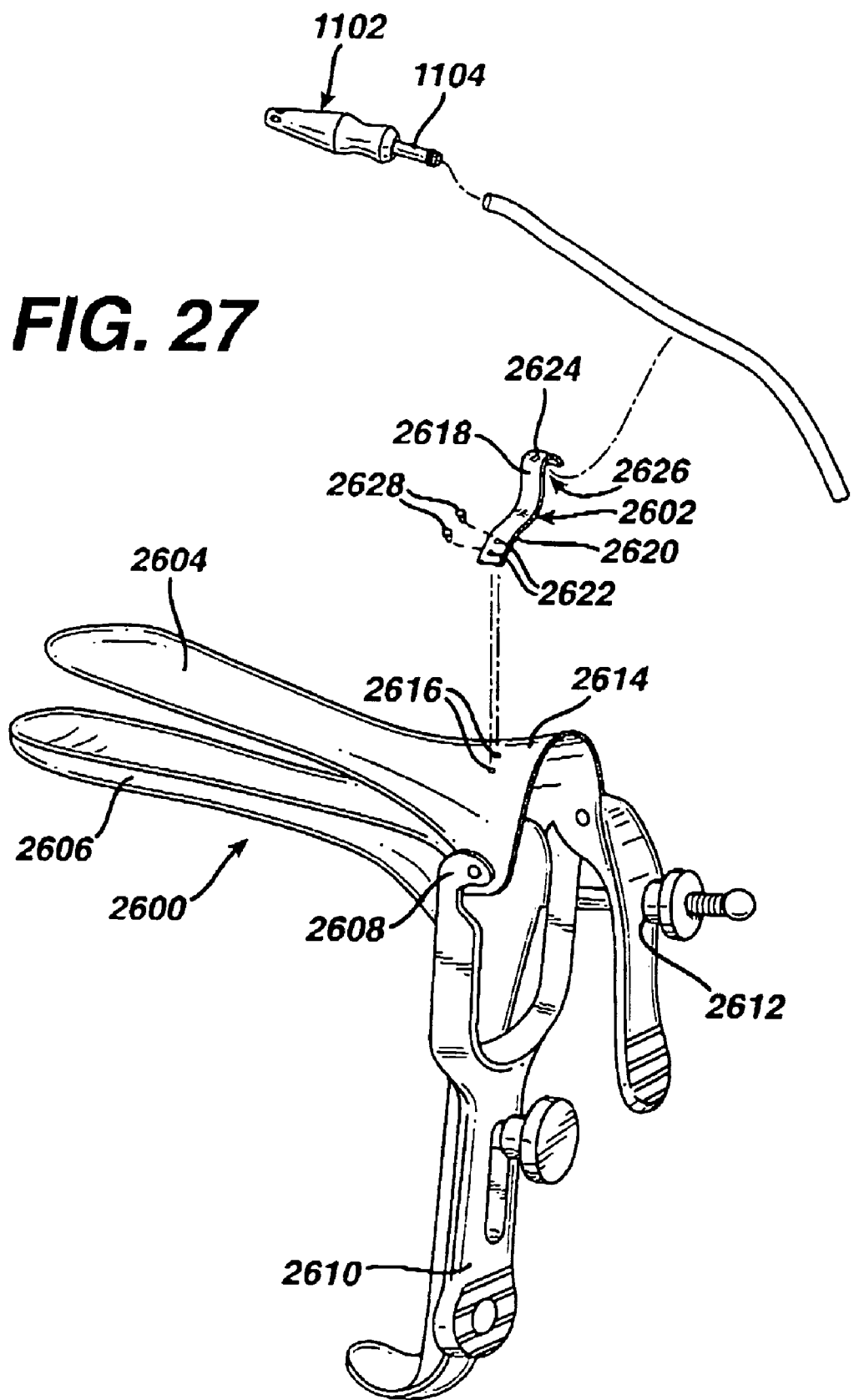
FIG. 27 is an exploded perspective view of the vaginal speculum assembly of FIG. 26.
Figure 28:
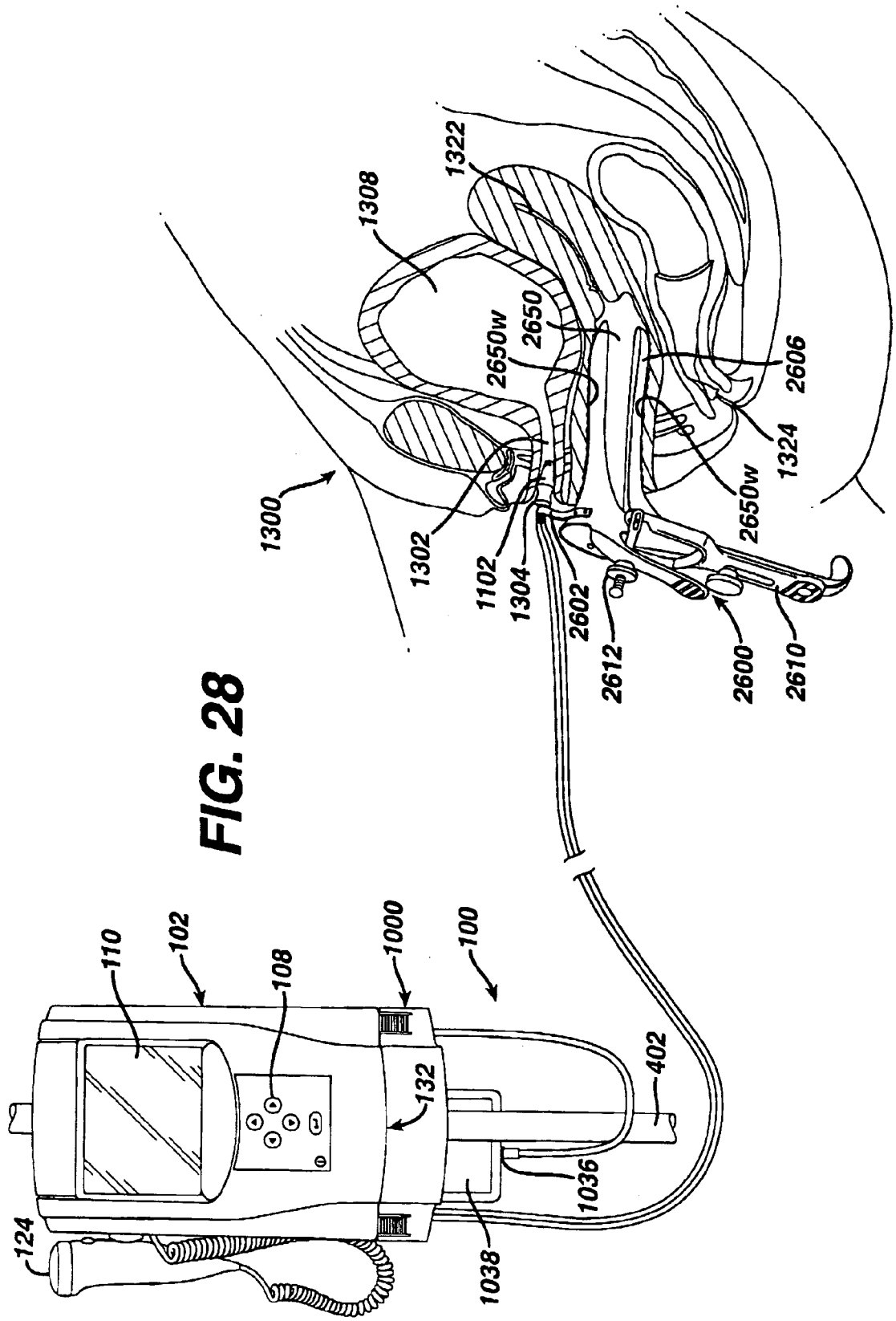
FIG. 28 is a schematic view of one embodiment of a urodynamic system and speculum assembly in relation to the female urinary/reproductive system.
Figure 29:
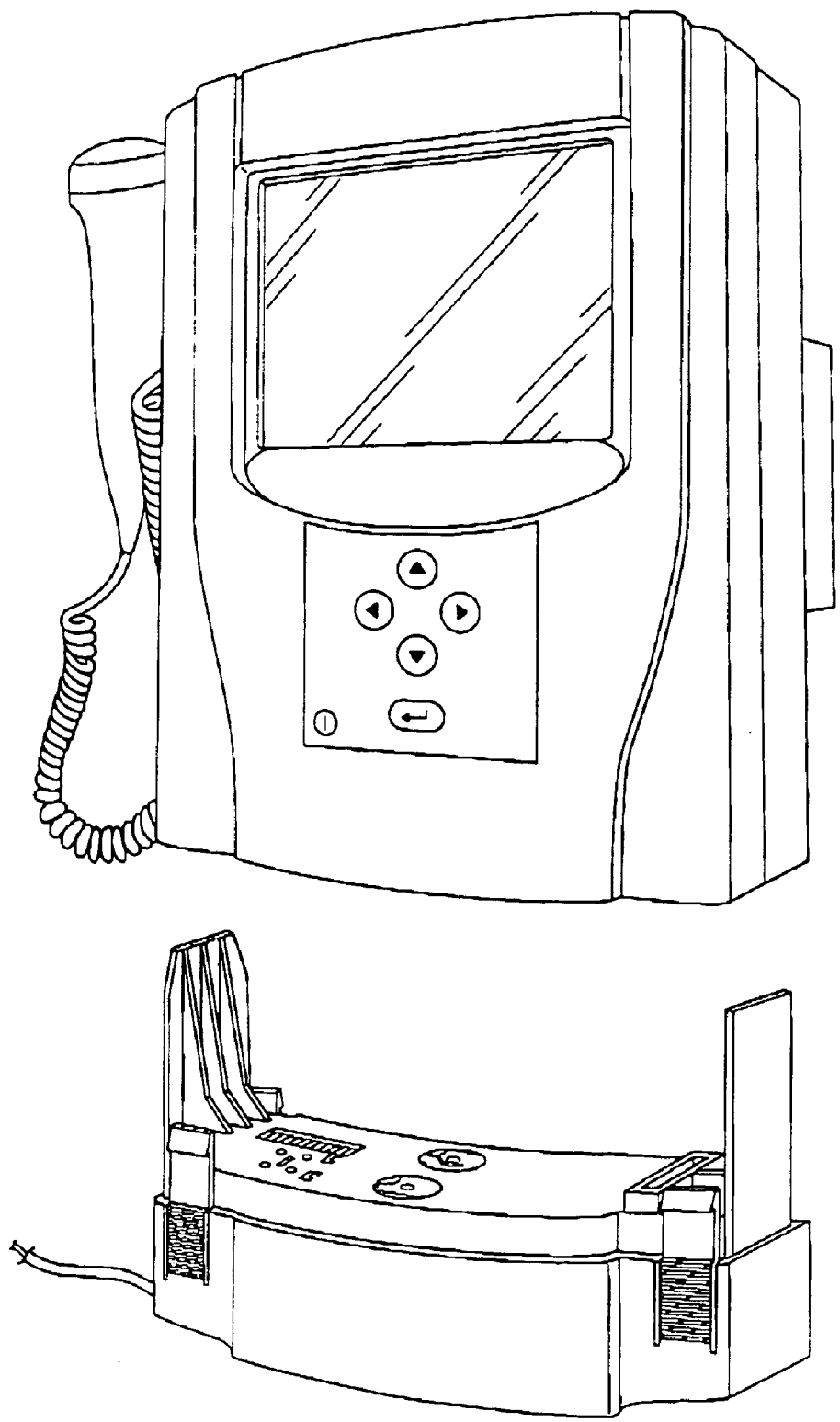
FIG. 29 is an exploded perspective view of a battery charger module that can be used in conjunction with the control device.

FIGS. 26–28 illustrate a vaginal speculum assembly 2600 for use in the reduction of vaginal prolapse when performing female urodynamic testing, as previously discussed. Uterine or vaginal prolapse occurs when the uterus or pelvic organs drop or become displaced because of weakened pelvic muscles. Prolapse must be reduced to effectively perform urodynamic tests to ensure that no underlying stress urinary incontinence symptoms are masked by the pressure of the vaginal prolapse, which may cause distortion or kinking of the urethral canal. The vaginal speculum assembly 2600 will permit the clinician or physician to perform a urodynamic test procedure with one hand while still reducing vaginal prolapse, as well as properly position the meatus plug device or other catheter within the urethral canal. This prolapse maneuver using the vaginal speculum assembly 2600 during urodynamic testing is especially important prior to surgical repair of the vaginal prolapse, as an undiagnosed case of stress urinary incontinence may surface following prolapse surgery. The urodynamic testing being performed using the vaginal speculum assembly in this manner allows the surgeon to determine if additional stress urinary incontinence (SUI) surgery should be performed at the time of prolapse repair.

Current medical practice calls for the use of a vaginal speculum secured in place in order to reduce the prolapse. For example, U.S. Pat. Nos. 5,997,474 and 6,048,308 describe specula specifically designed for vaginal examination and treatment. U.S. Pat. No. 6,120,438 discloses a vaginal retractor device designed to hold back the vaginal wall during an exam or surgical procedure. Often, surgical tape is necessary to hold the speculum in place, as the physician's hands cannot hold the speculum in place while performing a particular urodynamic procedure. None of the prior art speculum devices integrate the use of urodynamic equipment.

With reference to FIGS. 26 and 27, the vaginal speculum assembly 2600 includes a connector member 2602 for coupling an insertion device assembly, such as a meatus plug device 1102, or catheter 1422 and related elements to the vaginal speculum. The vaginal speculum can be of any type well known in the art. In the illustrated embodiment, the vaginal speculum includes an upper arm 2604, a lower arm 2606, and a hinge member 2608 for joining the upper and lower arms together. The vaginal speculum also includes a handled member 2610 being integrally attached, and preferably substantially perpendicular aligned to the lower arm. The vaginal speculum 2600 further includes a locking bar device 2612 connected to the upper arm 2606 for locking the upper and lower arms in an open position, as shown in FIG. 28. The upper arm 2604 includes a posterior end 2614 with a pair of arm mounting openings 2616 therein. The connector member 2602 includes a flexible band 2618. The flexible band at one end 2620 includes a pair of mounting openings 2622 and at the other end 2624 a connector element 2626. The mounting openings 2622 of the flexible band 2618 are aligned with the arm mounting openings 2616 of the upper arm for receiving a pair of mounting screws 2628 therein in order to attach the connector member 2602 to the vaginal speculum 2600. During use, the connector element can be coupled to the meatus plug device or catheter as shown in FIG. 26.

Although a particular embodiment of the connector member 2602 is illustrated and described herein, those skilled in the art will recognize that various other embodiments are also possible to provide a means by which to removably couple a device that is inserted into the urethral canal to the speculum so as to hold it in place within the patient.

In operation, the vaginal speculum assembly 2600 can be cooperatively used in conjunction with the urodynamic system disclosed herein. For example, it may be used in conjunction with a urodynamic system including a SUI testing module 1000 in the performance of the urodynamic testing procedure for stress urinary incontinence (SUI), such as the measuring of urethral resistance pressure (URP) as previously described. In reference to FIG. 28, the physician positions the vaginal speculum assembly 2600, such that it is fully inserted within vaginal canal 2650 wherein the upper and lower arms 2604, 2606 are fully opened and pressed against the vaginal walls 2650w for reducing the patient's vaginal prolapse. The physical then locks the upper and lower arms of the vaginal speculum in the fully opened configuration (see FIG. 28) via the locking bar device 2612, and adjusts the connector member 2602 so that the insert member will be aligned with the urethral canal. The remaining operational steps are exactly the same as the operational steps described above in connection with individual testing modules.

Although the portable medical system disclosed herein has been described in conjunction with diagnostic testing, it is to be understood that the system can also be used in conjunction with therapies and/or surgical procedures for treating urinary incontinence, such as placement of a sling, placement of bulking agents, shrinkage of tissue etc. In this regard, the testing described herein can be used before, during and/or after these procedures to ensure success of the procedures, for example, to ensure correct placement and/or tensioning of a sling.

Although exemplary embodiments and methods for use have been described in detail above, those skilled in the art will understand that many variations are possible without departing from the spirit and scope of the invention, which is limited only by the appended claims.

What is claimed is:

1. A portable, self-contained medical diagnostic system for assessing urinary function comprising:
    a control device having a substantially rigid outer casing, and including a microprocessor, a pump device, memory storing therein at least one software routine, and a pressure sensor are positioned within the outer casing;
    a test module having a substantially rigid outer casing, the test module being removably coupled to the control device, and further comprising a pressure interface positioned within the test module outer casing and a tubing assembly positioned partially within the test module housing and defining a first fluid conduit between a first fluid inlet and a first fluid outlet, wherein the pump device is coupled with the first fluid conduit for pumping fluid therethrough; and
    an insert member having a first channel therethrough and coupled to the first fluid outlet so that fluid flowing through the first fluid conduit may flow through the first channel, the insert member being dimensioned for insertion into a patient's bladder through the patient's urethral canal,
    wherein, when the insert member is inserted into the patient's bladder, the pressure interface is in fluid communication with the bladder such that a pressure at the pressure interface substantially corresponds to a pressure within the bladder, the pressure interface further being positioned relative to the pressure sensor so as to transmit bladder pressure information thereto, and wherein the microprocessor, via execution of the at least one software routine, controls operation of the pump and obtains bladder pressure information.

2. The diagnostic system according to claim 1, wherein the pump device is electrically coupled to and controlled by the processor, and wherein the pressure sensor is electrically coupled to and provides bladder pressure information to the processor.

3. The diagnostic system according to claim 1, wherein the test module further comprises a module identification device coupled with a module detection device in the control device, wherein the module detection device is electrically coupled to the control device processor.

4. The diagnostic system according to claim 1, wherein the insert member is a catheter.

5. The diagnostic system according to claim 4, wherein the catheter is a dual lumen catheter further comprising a second channel therethrough, wherein the pressure interface is in fluid communication with the second channel.

6. The diagnostic system according to claim 1, wherein the test module further comprises a test module housing having at least one tab element projecting therefrom for engaging the control device, and a first port therein dimensioned to receive the control device pressure sensor, wherein the pressure interface is positioned within the first port.

7. The diagnostic system according to claim 1, wherein the test module further comprises a second tubing conduit having an opening at one end thereof, and a second pressure interface in fluid communication with the second tubing conduit.

8. The diagnostic system according to claim 7, further comprising a second insert member coupled to the second tubing conduit opening, and dimensioned for insertion into the patient's body at a second location other than the urethral canal from which abdominal pressure can be sensed, the second insert member having a channel therethrough and being coupled to the second tubing conduit such that a pressure at the second interface substantially correlates to a pressure at the second location.

9. A medical diagnostic system comprising:
    a control device including a microprocessor and pump device electrically coupled to and controlled by the processor;
    a test module removably coupled to the control device and including a tubing assembly having a first fluid inlet, a first fluid outlet, and a first fluid conduit extending therebetween;
    an insert member coupled to the tubing assembly fluid outlet and having a channel therethrough in fluid communication with the first fluid conduit, the insert member being dimensioned for insertion into a patient's bladder through the patient's urethral canal;
    a pressure detection system for detecting pressure correlating to a pressure within the bladder;
    wherein the pump device is coupled to the first fluid conduit to, under control of the microprocessor, pump fluid through the first fluid conduit and insert member channel and into the bladder, and wherein the pressure detection system detects pressure within the bladder as fluid is pumped therein and provides data correlating to the detected pressure to the microprocessor.

10. The diagnostic system according to claim 9, wherein the insert member is a dual lumen catheter further comprising a second channel therethrough having an open distal end in proximity with an open distal end of the first channel, and wherein the pressure detection system further comprises a pressure interface within the test module in fluid communication with the second fluid conduit.

11. The diagnostic system according to claim 9, wherein the test module further comprises a module identification device coupled with a module detection device in the control device, wherein the module detection device is electrically coupled with the control device processor.

12. The diagnostic system according to claim 9, wherein the test module further comprises a pressure interface in fluid communication with the bladder when the insert member is inserted into the patient's bladder, and a test module housing having at least one tab element projecting therefrom for engaging the control device, and a first port therein dimensioned to receive the control device pressure sensor, wherein the pressure interface being positioned within the first port.

13. The diagnostic system according to claim 9, wherein the test module further comprises a second tubing conduit having an opening at one end thereof, and a second pressure interface in fluid communication with the second tubing conduit.

14. The diagnostic system according to claim 13, further comprising a second insert member coupled to the second tubing conduit opening, and dimensioned for insertion into the patient's body at a second location other than the urethral canal from which abdominal pressure can be sensed, the second insert member having a channel therethrough and being coupled to the second tubing conduit such that, when the second insert member is inserted into the patient's body, a pressure at the second interface substantially correlates to a pressure at the second location.

15. A method for assessing urinary function comprising the steps of:
removably coupling a test module to a control device to form a portable, self-contained diagnostic system, the control device including a microprocessor, a pump device and a pressure sensor, wherein operation of the pump device is controlled by the microprocessor and data correlating to pressure sensed by the pressure sensor is provided to the microprocessor, and the testing module including a fluid tubing assembly having a first fluid inlet, a first fluid outlet and a first fluid conduit extending therebetween;
coupling to the first fluid outlet an insert member having a channel therethrough in fluid communication with the first fluid conduit;
coupling the first fluid inlet to a fluid source;
inserting the insert member into a patient's bladder through the patient's urethral canal;
causing the microprocessor to execute the at least one software routine to thereby cause activation of the pump device to thereby infuse fluid from the fluid source through the first fluid conduit and insert member channel and into the bladder; and
measuring pressure within the bladder as fluid is infused therein.

16. The method according to claim 15, wherein the step of removably coupling the test module to the control device further comprises coupling a pressure interface in the test module with a pressure sensor in the control device that is electrically coupled to the processor.

17. The method according to claim 16, wherein the step of removably coupling the test module to the control device further comprises coupling the pump device with the first fluid conduit.

18. The method according to claim 15, wherein the test module further comprises a second fluid conduit having a distal open end and a second pressure interface in fluid communication with the second fluid conduit, the method further comprising coupling a second insert member to the distal open end and inserting the second insert member into the patient's body at a second location other than the urethral canal from which abdominal pressure can be sensed, the second insert member having a channel therethrough and being coupled to the second tubing conduit such that, when the second insert member is inserted into the patient's body, a pressure at the second interface substantially correlates to a pressure at the second location.

19. A self-contained medical diagnostic system for assessing urinary function comprising:
a control device including a microprocessor, a pump device electrically coupled to and controlled by the processor, and a first pressure sensor;
a testing module removably coupled to the control device, the testing module further comprising a first fluid conduit extending between a first fluid inlet and a first fluid outlet, and a second conduit having a first open end and a first pressure interface in fluid communication therewith; and
a first insert member having first and second channels therethrough, the first channel being in fluid communication with the first fluid conduit and the second channel being in communication with the second conduit, the insert member being dimensioned for insertion into a patient's bladder through the patient's urethral canal,
wherein the pump device is coupled to the first fluid conduit for infusing fluid through the first fluid conduit, the first insert member channel and into the bladder, and wherein the first pressure interface and first pressure sensor are positioned relative to one another so that the first pressure interface transmits pressure information to the first pressure sensor.

20. The diagnostic system according to claim 19, wherein the control device further comprises a second pressure sensor, and the test module further comprises a third tubing conduit having a first open end and a second pressure interface in communication therewith.

21. The diagnostic system according to claim 20, further comprising a second insert member coupled to the first open end of the third tubing conduit and being dimensioned for insertion into the patient's body at a second location other than the urethral canal at which abdominal pressure can be sensed.

22. The diagnostic system according to claim 21, wherein the second location is the rectum.

23. The diagnostic system according to claim 21, wherein the second location is the vaginal canal.

* * * * *